US012310631B2

(12) United States Patent
Mickiewicz et al.

(10) Patent No.: US 12,310,631 B2
(45) Date of Patent: May 27, 2025

(54) MULTI-FEATURE POLYAXIAL SCREW

(71) Applicant: Medos International Sarl, Le Locle (CH)

(72) Inventors: Christopher Mickiewicz, Bridgewater, MA (US); Ellen Roberts, Mendon, MA (US); Alec Manson, Boston, MA (US); Eric Biester, Barrington, RI (US); Paul S. Maguire, Hope Valley, RI (US)

(73) Assignee: Medos International Sárl, Le Locle (CH)

( * ) Notice: Subject to any disclaimer, the term of this patent is extended or adjusted under 35 U.S.C. 154(b) by 484 days.

(21) Appl. No.: 17/685,359

(22) Filed: Mar. 2, 2022

(65) Prior Publication Data

US 2022/0280200 A1    Sep. 8, 2022

Related U.S. Application Data

(60) Provisional application No. 63/221,359, filed on Jul. 13, 2021, provisional application No. 63/157,362, filed on Mar. 5, 2021.

(51) Int. Cl.
*A61B 17/70*  (2006.01)
*A61B 17/86*  (2006.01)

(52) U.S. Cl.
CPC ...... *A61B 17/7034* (2013.01); *A61B 17/7032* (2013.01); *A61B 17/7037* (2013.01);
(Continued)

(58) Field of Classification Search
CPC .................. A61B 17/7034; A61B 17/7037
See application file for complete search history.

(56) References Cited

U.S. PATENT DOCUMENTS

| 4,946,458 A | 8/1990 | Harms et al. |
| 5,443,467 A | 8/1995 | Biedermann et al. |

(Continued)

FOREIGN PATENT DOCUMENTS

| CN | 103565504 B | 7/2017 |
| DE | 10005386 A1 | 8/2001 |

(Continued)

OTHER PUBLICATIONS

International Search Report and Written Opinion for Application No. PCT/EP2022/055328, issued Aug. 25, 2022 (15 pages).

(Continued)

*Primary Examiner* — Olivia C Chang
(74) *Attorney, Agent, or Firm* — Barnes & Thornburg LLP

(57) ABSTRACT

Bone anchor assemblies are disclosed herein that provide for a single bone anchor assembly that can be utilized across a range of spinal surgical procedures, reduce manufacturing burden and cost, and provide for greater flexibility during a surgical procedure. The bone anchor assemblies disclosed herein include an implantable shank and a receiver member having two spaced apart arms which form a U-shaped seat to receive a rod, among other components. The bone anchor assemblies disclosed herein also provide a number of features to enhance capability and usability. Examples include features to facilitate better implantation of the shank, better coupling of instrumentation to the anchor, better performance in reducing a spinal fixation element, such as a rod, into the receiver member seat, and others.

33 Claims, 34 Drawing Sheets

(52) U.S. Cl.
CPC .......... *A61B 17/862* (2013.01); *A61B 17/864* (2013.01); *A61B 17/8685* (2013.01)

(56) References Cited

U.S. PATENT DOCUMENTS

| | | |
|---|---|---|
| 5,536,268 A | 7/1996 | Griss |
| 5,672,176 A | 9/1997 | Biedermann et al. |
| 5,733,285 A | 3/1998 | Errico et al. |
| 5,733,286 A | 3/1998 | Errico et al. |
| 5,782,833 A | 7/1998 | Haider |
| 5,879,350 A | 3/1999 | Sherman et al. |
| 5,885,286 A | 3/1999 | Sherman et al. |
| 5,891,145 A | 4/1999 | Morrison et al. |
| 5,961,517 A | 10/1999 | Biedermann et al. |
| 6,063,090 A | 5/2000 | Schlapfer |
| 6,090,111 A | 7/2000 | Nichols |
| 6,113,601 A | 9/2000 | Tatar |
| 6,248,105 B1 | 6/2001 | Schläpfer et al. |
| 6,254,602 B1 | 7/2001 | Justis |
| 6,280,442 B1 | 8/2001 | Barker et al. |
| 6,287,311 B1 | 9/2001 | Sherman et al. |
| 6,355,040 B1 | 3/2002 | Richelsoph et al. |
| 6,371,957 B1 | 4/2002 | Amrein et al. |
| 6,402,752 B2 | 6/2002 | Schäffler-Wachter et al. |
| 6,471,705 B1 | 10/2002 | Biedermann et al. |
| 6,485,491 B1 | 11/2002 | Farris et al. |
| 6,540,748 B2 | 4/2003 | Lombardo |
| 6,582,436 B2 | 6/2003 | Schlapfer et al. |
| 6,585,737 B1 | 7/2003 | Baccelli et al. |
| 6,660,004 B2 | 12/2003 | Barker et al. |
| 6,736,820 B2 | 5/2004 | Biedermann et al. |
| 6,755,829 B1 | 6/2004 | Bono et al. |
| 6,835,196 B2 | 12/2004 | Biedermann et al. |
| 6,837,889 B2 | 1/2005 | Shluzas |
| 6,869,433 B2 | 3/2005 | Glascott |
| 6,905,500 B2 | 6/2005 | Jeon et al. |
| 6,974,460 B2 | 12/2005 | Carbone et al. |
| 7,066,937 B2 | 6/2006 | Shluzas |
| 7,081,116 B1 | 7/2006 | Carly |
| 7,087,057 B2 | 8/2006 | Konieczynski et al. |
| 7,090,679 B2 | 8/2006 | Saint-Martin et al. |
| 7,125,426 B2 | 10/2006 | Moumene et al. |
| 7,144,396 B2 | 12/2006 | Shluzas |
| 7,179,261 B2 | 2/2007 | Sicvol et al. |
| 7,186,255 B2 | 3/2007 | Baynham et al. |
| 7,316,684 B1 | 1/2008 | Baccelli et al. |
| 7,479,156 B2 | 1/2009 | Lourdel et al. |
| 7,604,656 B2 | 10/2009 | Shluzas |
| 7,682,377 B2 | 3/2010 | Konieczynski et al. |
| 7,699,876 B2 | 4/2010 | Barry et al. |
| 7,717,939 B2 | 5/2010 | Ludwig et al. |
| 7,727,261 B2 | 6/2010 | Barker et al. |
| 7,766,945 B2 | 8/2010 | Nilsson et al. |
| 7,789,900 B2 | 9/2010 | Levy et al. |
| 7,857,834 B2 | 12/2010 | Boschert |
| 7,879,075 B2 | 2/2011 | Shluzas |
| 7,922,748 B2 | 4/2011 | Hoffman |
| 7,942,910 B2 | 5/2011 | Doubler et al. |
| 7,951,173 B2 | 5/2011 | Hammill, Sr. et al. |
| 8,021,397 B2 | 9/2011 | Farris et al. |
| 8,038,701 B2 | 10/2011 | Rock et al. |
| 8,062,339 B2 | 11/2011 | Hammer et al. |
| 8,100,916 B2 | 1/2012 | Kumar et al. |
| 8,133,262 B2 | 3/2012 | Whipple |
| 8,157,846 B2 | 4/2012 | Randol et al. |
| 8,162,991 B2 | 4/2012 | Strauss et al. |
| 8,167,914 B1 | 5/2012 | Hunt et al. |
| 8,197,517 B1 | 6/2012 | Lab et al. |
| 8,257,399 B2 | 9/2012 | Biedermann et al. |
| 8,298,274 B2 | 10/2012 | Barker, Jr. et al. |
| 8,303,602 B2 | 11/2012 | Biedermann et al. |
| 8,313,516 B2 | 11/2012 | Konieczynski et al. |
| 8,337,530 B2 | 12/2012 | Hestad et al. |
| 8,377,101 B2 | 2/2013 | Barrus et al. |
| 8,444,681 B2 | 5/2013 | Jackson et al. |
| 8,460,308 B2 | 6/2013 | Marino et al. |
| 8,529,604 B2 | 9/2013 | Barker, Jr. et al. |
| 8,556,938 B2 | 10/2013 | Jackson et al. |
| 8,603,145 B2 | 12/2013 | Forton et al. |
| 8,632,571 B2 | 1/2014 | Kraus |
| 8,663,288 B2 | 3/2014 | Konieczynski et al. |
| 8,663,290 B2 | 3/2014 | Doubler et al. |
| 8,696,717 B2 | 4/2014 | Rock et al. |
| 8,709,050 B2 | 4/2014 | Shluzas |
| 8,709,051 B2 | 4/2014 | Hammer et al. |
| 8,828,060 B2 | 9/2014 | Biedermann et al. |
| 8,852,239 B2 | 10/2014 | Jackson et al. |
| 8,870,919 B2 | 10/2014 | Miller et al. |
| 8,876,869 B1 | 11/2014 | Schafer et al. |
| 8,900,240 B2 | 12/2014 | White et al. |
| 8,906,068 B1 | 12/2014 | Bedor |
| 8,936,624 B2 | 1/2015 | Shluzas |
| 8,945,189 B2 | 2/2015 | Barrus et al. |
| 8,951,290 B2 | 2/2015 | Hammer et al. |
| 8,986,349 B1 | 3/2015 | German et al. |
| 8,998,959 B2 | 4/2015 | Jackson et al. |
| 9,005,260 B2 | 4/2015 | Dauster et al. |
| 9,023,086 B2 | 5/2015 | Biedermann et al. |
| 9,034,021 B2 | 5/2015 | Matthis et al. |
| 9,066,761 B2 | 6/2015 | McBride et al. |
| 9,078,715 B2 | 7/2015 | Biedermann et al. |
| 9,084,634 B1 | 7/2015 | Lab et al. |
| 9,144,444 B2 | 9/2015 | Jackson |
| 9,149,300 B2 | 10/2015 | Biedermann et al. |
| 9,155,567 B2 | 10/2015 | Auerbach et al. |
| 9,168,069 B2 | 10/2015 | Jackson et al. |
| 9,186,191 B2 | 11/2015 | Berrevoets et al. |
| 9,232,969 B2 | 1/2016 | Farris |
| 9,241,737 B2 | 1/2016 | Biedermann et al. |
| 9,254,151 B2 | 2/2016 | Walker et al. |
| 9,271,761 B2 | 3/2016 | Legallois et al. |
| 9,277,938 B2 | 3/2016 | Biedermann et al. |
| 9,314,280 B2 | 4/2016 | Corin |
| 9,393,048 B2 | 7/2016 | Carbone et al. |
| 9,451,992 B2 | 9/2016 | Jensen et al. |
| 9,504,497 B2 | 11/2016 | Ark et al. |
| 9,510,862 B2 | 12/2016 | Montello et al. |
| 9,526,529 B2 | 12/2016 | Charvet |
| 9,554,829 B2 | 1/2017 | Cahill et al. |
| 9,603,632 B1 | 3/2017 | Gunn et al. |
| 9,642,654 B2 | 5/2017 | Reimels et al. |
| 9,649,134 B2 | 5/2017 | Hannen |
| 9,649,135 B2 | 5/2017 | Doubler et al. |
| 9,649,142 B2 | 5/2017 | Doubler et al. |
| 9,655,657 B2 | 5/2017 | Konieczynski et al. |
| 9,700,355 B2 | 7/2017 | Longtain et al. |
| 9,763,700 B1 | 9/2017 | Gregory |
| 9,788,865 B2 | 10/2017 | Matthis et al. |
| 9,844,400 B2 | 12/2017 | Stevenson et al. |
| 9,943,338 B2 | 4/2018 | Biedermann et al. |
| 9,993,270 B2 | 6/2018 | Butler |
| 10,016,223 B2 | 7/2018 | Mishra |
| 10,039,572 B2 | 8/2018 | Harris et al. |
| 10,052,137 B2 | 8/2018 | Landry et al. |
| 10,064,657 B2 | 9/2018 | Spitler |
| 10,172,649 B2 | 1/2019 | Jackson et al. |
| 10,251,677 B2 | 4/2019 | Heuer et al. |
| 10,258,390 B2 | 4/2019 | Biedermann et al. |
| 10,271,877 B2 | 4/2019 | Biedermann et al. |
| 10,299,836 B2 | 5/2019 | Daniels |
| 10,335,202 B2 | 7/2019 | Ziolo et al. |
| 10,357,289 B2 | 7/2019 | Biedermann et al. |
| 10,368,916 B2 | 8/2019 | May |
| 10,368,917 B2 | 8/2019 | Mishra et al. |
| 10,383,659 B2 | 8/2019 | Pham et al. |
| 10,426,520 B2 | 10/2019 | Biedermann et al. |
| 10,426,538 B2 | 10/2019 | Jones et al. |
| 10,441,328 B2 | 10/2019 | Petit |
| 10,456,173 B1 | 10/2019 | Casey et al. |
| 10,478,227 B2 | 11/2019 | Leff et al. |
| 10,478,228 B2 | 11/2019 | Kim et al. |
| 10,499,955 B2 | 12/2019 | Faulhaber |
| 10,499,957 B2 | 12/2019 | Jones et al. |
| 10,507,043 B1 | 12/2019 | Gladieux |

(56) References Cited

U.S. PATENT DOCUMENTS

| | | | |
|---|---|---|---|
| 10,517,645 B2 | 12/2019 | van der Pol |
| 10,524,839 B2 | 1/2020 | Ahn |
| 10,555,759 B2 | 2/2020 | Krüger |
| 10,555,760 B2 | 2/2020 | Buttermann |
| 10,588,666 B2 | 3/2020 | Samuel et al. |
| 10,595,903 B2 | 3/2020 | Heuer |
| 10,603,081 B2 | 3/2020 | Harper et al. |
| 10,603,082 B2 | 3/2020 | Lish |
| 10,603,083 B1 | 3/2020 | Gladieux et al. |
| 10,610,260 B2 | 4/2020 | Biedermann et al. |
| 10,610,265 B1 | 4/2020 | Ark et al. |
| 10,631,901 B2 | 4/2020 | Fiechter et al. |
| 10,639,077 B2 | 5/2020 | Nichols et al. |
| 10,639,080 B2 | 5/2020 | Sharifi-Mehr et al. |
| 10,702,310 B2 | 7/2020 | Leff et al. |
| 10,716,609 B2 | 7/2020 | Biedermann et al. |
| 10,722,276 B2 | 7/2020 | Barrus et al. |
| 2003/0187433 A1 | 10/2003 | Lin |
| 2004/0249378 A1 | 12/2004 | Saint Martin et al. |
| 2004/0267264 A1 | 12/2004 | Konieczynski et al. |
| 2006/0089644 A1 | 4/2006 | Felix |
| 2006/0129149 A1 | 6/2006 | Iott et al. |
| 2007/0055240 A1 | 3/2007 | Matthis et al. |
| 2007/0093826 A1 | 4/2007 | Hawkes et al. |
| 2007/0118123 A1 | 5/2007 | Strausbaugh et al. |
| 2007/0161998 A1 | 7/2007 | Whipple |
| 2007/0270806 A1 | 11/2007 | Foley et al. |
| 2008/0015579 A1 | 1/2008 | Whipple |
| 2008/0015597 A1 | 1/2008 | Whipple |
| 2008/0132957 A1 | 6/2008 | Matthis et al. |
| 2008/0161859 A1 | 7/2008 | Nilsson |
| 2008/0200956 A1 | 8/2008 | Beckwith et al. |
| 2008/0249570 A1 | 10/2008 | Carson et al. |
| 2008/0262556 A1 | 10/2008 | Jacofsky et al. |
| 2009/0118772 A1 | 5/2009 | Diederich et al. |
| 2009/0318970 A1 | 12/2009 | Butler et al. |
| 2010/0010540 A1 | 1/2010 | Park |
| 2010/0114174 A1 | 5/2010 | Jones et al. |
| 2010/0152785 A1 | 6/2010 | Forton et al. |
| 2010/0249846 A1 | 9/2010 | Simonson |
| 2011/0040338 A1 | 2/2011 | Jackson |
| 2011/0087288 A1 | 4/2011 | Stevenson et al. |
| 2011/0098755 A1 | 4/2011 | Jackson et al. |
| 2011/0257690 A1 | 10/2011 | Rezach |
| 2011/0282399 A1 | 11/2011 | Jackson |
| 2011/0288599 A1 | 11/2011 | Michielli et al. |
| 2012/0089150 A1 | 4/2012 | Smith |
| 2012/0136395 A1 | 5/2012 | Biedermann et al. |
| 2012/0143260 A1 | 6/2012 | Gunn et al. |
| 2012/0143265 A1 | 6/2012 | Biedermann et al. |
| 2012/0165881 A1 | 6/2012 | Biedermann et al. |
| 2012/0215264 A1 | 8/2012 | Lee |
| 2012/0253408 A1 | 10/2012 | Timm |
| 2012/0303072 A1 | 11/2012 | Eisermann |
| 2012/0310284 A1 | 12/2012 | Gerchow |
| 2012/0316605 A1 | 12/2012 | Palagi |
| 2013/0053901 A1 | 2/2013 | Cormier et al. |
| 2013/0060294 A1 | 3/2013 | Donahue |
| 2013/0066376 A1 | 3/2013 | Biedermann et al. |
| 2013/0096620 A1 | 4/2013 | Biedermann et al. |
| 2013/0123858 A1 | 5/2013 | Attia |
| 2013/0144349 A1 | 6/2013 | Corin |
| 2013/0165977 A1 | 6/2013 | Biedermann et al. |
| 2013/0197586 A1 | 8/2013 | Matthis et al. |
| 2013/0211467 A1 | 8/2013 | Dickinson |
| 2013/0218213 A1 | 8/2013 | Lemoine |
| 2013/0238030 A1 | 9/2013 | Steib |
| 2013/0338716 A1 | 12/2013 | Biedermann et al. |
| 2014/0012337 A1 | 1/2014 | Biedermann et al. |
| 2014/0018867 A1 | 1/2014 | Freudiger et al. |
| 2014/0094849 A1 | 4/2014 | Spratt et al. |
| 2014/0121703 A1 | 5/2014 | Jackson et al. |
| 2014/0142632 A1* | 5/2014 | Keyer ............... A61B 17/8841 606/265 |
| 2014/0142634 A1 | 5/2014 | Schlaepfer et al. |
| 2014/0163618 A1 | 6/2014 | Legallois et al. |
| 2014/0188173 A1 | 7/2014 | Mishra et al. |
| 2014/0257409 A1 | 9/2014 | Reed |
| 2014/0277159 A1 | 9/2014 | Spratt et al. |
| 2014/0277161 A1 | 9/2014 | Spratt et al. |
| 2014/0277189 A1 | 9/2014 | Spratt et al. |
| 2014/0343617 A1* | 11/2014 | Hannen ............... A61B 17/8605 606/306 |
| 2014/0358182 A1 | 12/2014 | Puekert |
| 2015/0032162 A1 | 1/2015 | Biedermann et al. |
| 2015/0173816 A1 | 6/2015 | Biedermann et al. |
| 2015/0196337 A1 | 7/2015 | Biedermann et al. |
| 2015/0282844 A1 | 10/2015 | Vedula et al. |
| 2016/0000470 A1 | 1/2016 | Matthis et al. |
| 2016/0015429 A1 | 1/2016 | Butler |
| 2016/0030086 A1 | 2/2016 | Mishra |
| 2016/0038204 A1 | 2/2016 | Biedermann et al. |
| 2016/0045228 A1 | 2/2016 | Biedermann et al. |
| 2016/0192966 A1 | 7/2016 | Biedermann et al. |
| 2016/0296256 A1 | 10/2016 | Chandanson et al. |
| 2016/0317206 A1 | 11/2016 | Rezach et al. |
| 2017/0049482 A1 | 2/2017 | Campbell et al. |
| 2017/0112543 A1 | 4/2017 | Jackson |
| 2017/0209185 A1 | 7/2017 | Trautwein et al. |
| 2017/0360491 A1 | 12/2017 | Spratt et al. |
| 2018/0092666 A1 | 4/2018 | Wu et al. |
| 2018/0193063 A1 | 7/2018 | May |
| 2018/0325569 A1 | 11/2018 | Ramsay et al. |
| 2019/0021769 A1 | 1/2019 | Lish |
| 2019/0029731 A1 | 1/2019 | Shoshtaev |
| 2019/0038319 A1 | 2/2019 | Biedermann et al. |
| 2019/0150989 A1 | 5/2019 | Biester et al. |
| 2019/0150990 A1 | 5/2019 | Jackson et al. |
| 2019/0223917 A1 | 7/2019 | Gray et al. |
| 2019/0247093 A1 | 8/2019 | Jackson et al. |
| 2019/0262044 A1 | 8/2019 | Roth et al. |
| 2019/0274738 A1 | 9/2019 | Heuer |
| 2020/0038075 A1 | 2/2020 | Barrus et al. |
| 2020/0197052 A1 | 6/2020 | Heuer et al. |
| 2020/0367939 A1 | 11/2020 | Loftis et al. |
| 2021/0113246 A1 | 4/2021 | Biester et al. |
| 2021/0275232 A1 | 9/2021 | Keyer et al. |
| 2021/0282819 A1* | 9/2021 | Biedermann ...... A61B 17/7038 |
| 2022/0280201 A1 | 9/2022 | Mickiewicz et al. |

FOREIGN PATENT DOCUMENTS

| | | |
|---|---|---|
| EP | 1210914 B1 | 5/2005 |
| EP | 2208472 A1 | 7/2010 |
| EP | 2208472 B1 | 4/2011 |
| EP | 2687171 A1 | 1/2014 |
| EP | 2687172 A1 | 1/2014 |
| EP | 2687172 B1 | 3/2015 |
| EP | 2687171 B1 | 4/2015 |
| JP | 2005516721 A | 6/2005 |
| JP | 2009544414 A | 12/2009 |
| JP | 2016064290 A | 4/2016 |
| WO | 2001006940 A1 | 2/2001 |
| WO | 2001010317 A1 | 2/2001 |
| WO | 2003037199 A1 | 5/2003 |
| WO | 2008016892 A2 | 2/2008 |
| WO | 2009015100 A2 | 1/2009 |
| WO | 2012064360 A1 | 5/2012 |
| WO | 2013063477 A1 | 5/2013 |
| WO | 2016020158 A1 | 2/2016 |
| WO | 2016065033 A1 | 4/2016 |

OTHER PUBLICATIONS

International Search Report and Written Opinion for Application No. PCT/EP2022/0553525, issued Jun. 23, 2022 (10 pages).
[No Author Listed] Expedium Verse® Spinal System, System Guide, 2015, 52 pages.
[No Author Listed] Synapse System Surgical Technique, DePuy Synthes, 2016, 68 pages.
[No Author Listed] Synapse System Technique Guide, Synthes Spine, 2007, 51 pages.

(56) References Cited

OTHER PUBLICATIONS

International Search Report and Written Opinion for Application No. PCT/US2018/031296, mailed Oct. 10, 2018 (20 Pages).
U.S. Appl. No. 15/591,608, filed May 10, 2017, Bone Anchors With Drag Features and Related Methods.
International Search Report and Written Opinion for Application No. PCT/EP2022/055325, mailed Jun. 23, 2022 (11 pages).
International Search Report and Written Opinion for Application No. PCT/EP2022/055328, mailed Aug. 25, 2022 (16 pages).
Japanese Office Action (Notice of Reasons for Refusal) for Application No. 2019-561721, dated Aug. 1, 2023 (6 pages).
European Office Action (Search Report) for Application No. 187266762, dated Aug. 11, 2023 (10 pages).

\* cited by examiner

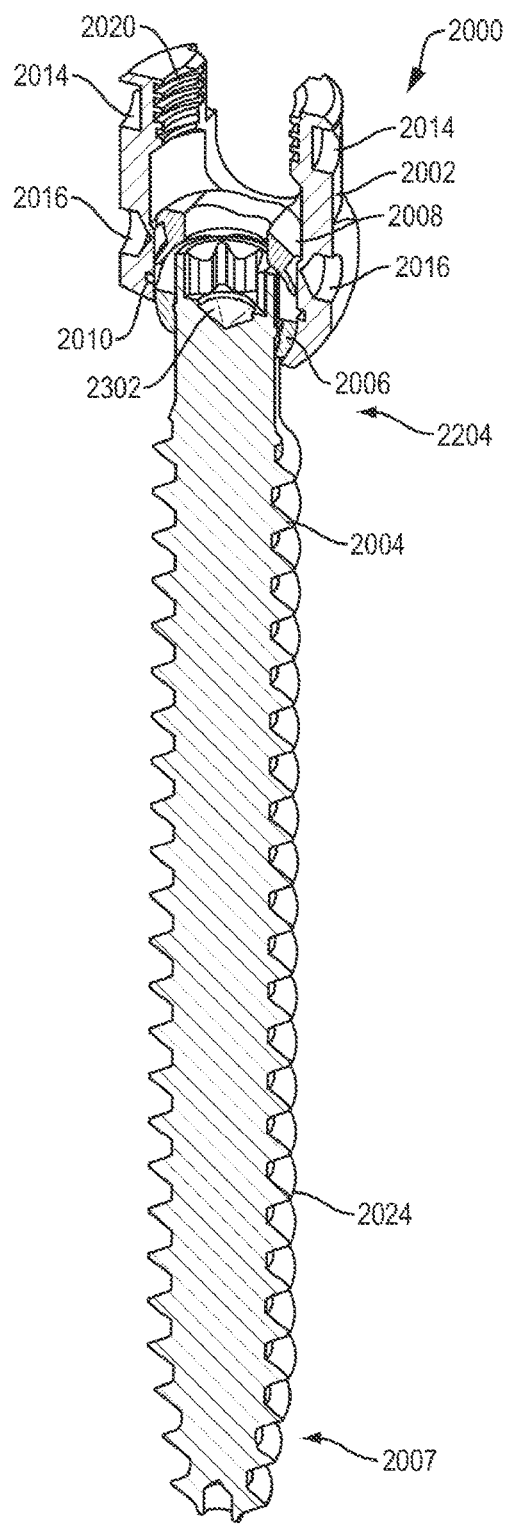
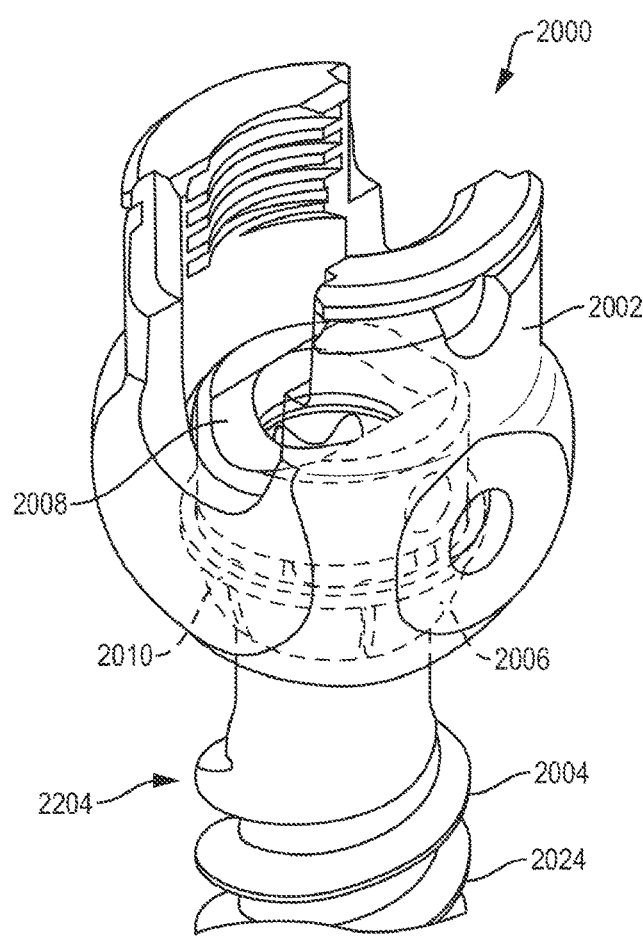
FIG. 23
FIG. 24

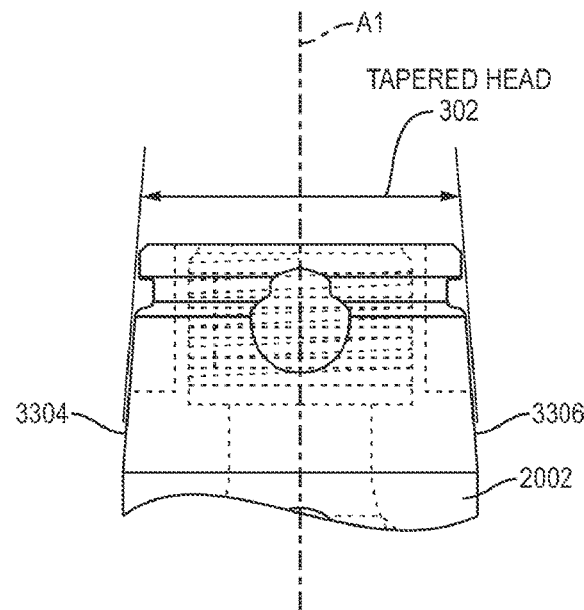
FIG. 33
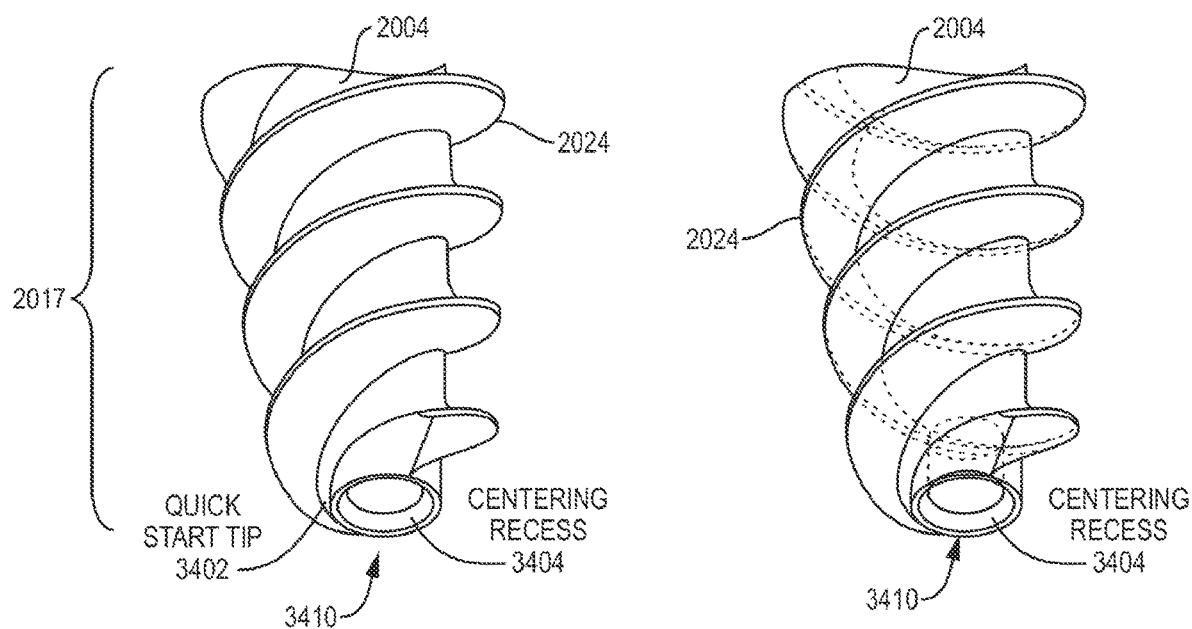
FIG. 34A
FIG. 34B

MULTI-FEATURE POLYAXIAL SCREW

CROSS-REFERENCE TO RELATED APPLICATIONS

This application claims the benefit of U.S. Provisional Application No. 63/157,362, filed on Mar. 5, 2021. This application also claims the benefit of U.S. Provisional Application No. 63/221,359, filed on Jul. 13, 2021. The entire contents of these applications are hereby incorporated by reference in their entirety.

FIELD

This disclosure relates generally to improved polyaxial bone anchor assemblies, which can include a plurality of features, e.g., for optimized or improved engagement with surgical instruments, surgical instrumentation, and/or bone, applicable for use in at least thoracolumbar spinal applications.

BACKGROUND

Bone anchor assemblies can be used in orthopedic surgery to fix bone during healing, fusion, or other processes. In spinal surgery, for example, bone anchor assemblies can be used to secure a rod or other spinal fixation element to one or more vertebrae to rigidly or dynamically stabilize the spine. Bone anchor assemblies typically include a bone screw with a threaded shank that is adapted to be threaded into a vertebra, and a rod-receiving element, usually in the form of a U-shaped slot formed in the head. The shank and rod-receiving assembly can be provided as a monoaxial screw, whereby the rod-receiving element is fixed with respect to the shank, or a polyaxial screw, whereby the rod-receiving element has free angular movement with respect to the shank. In use, the shank portion of each screw is threaded into a vertebra, and once properly positioned, a fixation rod is seated into the rod-receiving element of each screw. The rod is then locked in place by tightening a set-screw, plug, or similar type of fastening mechanism into the rod-receiving element.

With prior bone anchor assemblies, there are a large variety of anchors suited for specific uses and this can make it difficult for a user to select the proper anchor, and for suppliers to manufacture and maintain inventories. Further, with prior anchors there are many ways in which use can be challenging, such as when implanting an anchor, when coupling instrumentation to an anchor, when reducing a spinal fixation element toward an anchor, etc.

Accordingly, there is a need for improved bone anchor assemblies, particularly assemblies that can be used across a wide variety of situations and provide solutions to various usability challenges.

SUMMARY

The bone anchor assemblies disclosed herein, and methods related to the same, provide for a single bone anchor assembly that can be utilized across a range of spinal surgical procedures, reduce manufacturing burden and cost, and provide for greater flexibility during a surgical procedure. The bone anchor assemblies disclosed herein include an implantable shank and a receiver member having two spaced apart arms which form a U-shaped seat to receive a rod, among other components. The bone anchor assemblies disclosed herein also provide a number of features to enhance capability and usability. These include, for example, features to facilitate better implantation of the shank, better coupling of instrumentation to the anchor, better performance in reducing a spinal fixation element, such as a rod, into the receiver member seat, and others.

In one aspect, a bone anchor assembly is disclosed that includes a bone anchor having a proximal head portion and a distal threaded bone-engaging portion. The bone anchor further includes a receiver member having a proximal end defined by a pair of spaced apart arms forming a U-shaped recess therebetween, a distal end having a polyaxial seat formed therein for polyaxially seating the head portion of the bone anchor, a groove formed in an outer surface of each of the spaced apart arms at a proximal end thereof, a first recess formed in the outer surface of each arm with at least a portion of the first recess intersecting the groove, and a second recess formed in an outer surface of the receiver member at a position distal to the first recesses. Moreover, the first recesses and the second recesses are configured to couple to a surgical instrument.

Any of a variety of alternative or additional features can be included and are considered within the scope of the present disclosure. For example, in some embodiments, at least a portion of the first recess in each arm can extend proximally beyond the groove. In certain embodiments, each of the second recesses can be longitudinally aligned with one of the first recesses. In some embodiments, the first recesses can be configured to pivotably couple to a surgical instrument. In certain embodiments, the pair of second recesses can be configured to pivotably couple to a surgical instrument.

In some embodiments, the U-shaped recess can be configured to receive a spinal fixation element of various sizes.

In certain embodiments, each spaced apart arm can have a laterally-facing recessed portion formed on opposite lateral edges of the arm, each of the lateral-facing recessed portions facing away from a central proximal-distal axis of the receiver member, wherein the lateral-facing recessed portions can be configured to engage with a surgical instrument such that the U-shaped recess remains unobstructed. In some embodiments, each of the lateral-facing recessed portions can extend distally from the proximal end of the spaced apart arms. In certain embodiments, each lateral-facing recessed portion can have a concave distal surface. In some embodiments, each lateral-facing recessed portion can have a first planar surface, a second planar surface substantially perpendicular to the first planar surface, and a curved surface therebetween.

In some embodiments, the proximal ends of the spaced apart arms can lie along a common circular circumferential path.

In certain embodiments, opposing laterally-facing sides of the receiver member can taper inward towards the proximal end of the receiver member. In some embodiments, a first pair of opposed sides of the receiver member can have a first taper with respect to a first plane that contains a proximal-distal axis of the receiver member. A second pair of opposed sides of the receiver member can have a second taper with respect to a second plane that contains the proximal-distal axis and is offset from the first plane. The first plane can be perpendicular to the second plane.

In some embodiments, the assembly can include a drag ring disposed within the receiver member, the drag ring can be configured to exert a friction force on the head portion of the bone anchor.

In certain embodiments, the assembly can include a compression member disposed within the receiver member, wherein a proximal portion of the compression member includes opposing planar surfaces that are angularly offset from one another forming a seat for receiving a spinal fixation element. Material displaced in the formation of the second recesses can be configured to restrict movement of the compression member relative to the receiver member. The displaced material can be received within corresponding recesses formed in the compression member.

In some embodiments, the assembly can include a pair of reduction tabs extending proximally from the pair of spaced apart arms.

In certain embodiments, the assembly can include a fixation element with external square threads configured to be received between the spaced apart arms of the receiver member.

In some embodiments, the bone anchor can includes a bore extending proximally from a distal tip of the bone engaging portion. The bore can extend through an entire length of the bone anchor. The bore can be a blind bore.

In some embodiments, the distal bone-engaging portion can include external threads that extend distally along the bone-engaging portion to a distal tip thereof.

In another aspect, a bone anchor assembly is disclosed that includes a bone anchor having a proximal head portion and a distal threaded bone-engaging portion. The assembly further includes a receiver member having a proximal end defined by a pair of spaced apart arms forming a U-shaped recess configured to receive a spinal fixation element therebetween and a distal end having a polyaxial seat formed therein for polyaxially seating the head portion of the bone anchor. Moreover, opposing laterally-facing sides of the receiver member taper inward towards the proximal end of the receiver member.

As with the assemblies described above, there are a variety of additional or alternative features that are considered within the scope of the present disclosure. For example, in some embodiments a first pair of the opposing laterally-facing sides of the receiver member can have a first taper with respect to a first plane that contains a proximal-distal axis of the receiver member. A second pair of the opposing laterally-facing sides of the receiver member can have a second taper with respect to a second plane that contains the proximal-distal axis and is offset from the first plane. The first plane can be perpendicular to the second plane.

In some embodiments, the receiver member can include a groove formed in an outer surface of each of the spaced apart arms at a proximal end thereof, a first recess formed in the outer surface of each arm with at least a portion of the first recess intersecting the groove, and a second recess formed in an outer surface of the receiver member at a position distal to the first recesses. The first recesses and the second recesses can be configured to couple to a surgical instrument. At least a portion of the first recess in each arm can extend proximally beyond the groove. Each of the second recesses can be longitudinally aligned with one of the first recesses. The first recesses can be configured to pivotably couple to a surgical instrument. The pair of second recesses can be configured to pivotably couple to a surgical instrument.

In some embodiments, the U-shaped recess can be configured to receive a spinal fixation element of various sizes.

In certain embodiments, each spaced apart arm can have a laterally-facing recessed portion formed on opposite lateral edges of the arm, each of the lateral-facing recessed portions facing away from a central proximal-distal axis of the receiver member, wherein the lateral-facing recessed portions are configured to engage with a surgical instrument such that the U-shaped recess remains unobstructed. Each of the lateral-facing recessed portions can extend distally from the proximal end of the spaced apart arms. Each lateral-facing recessed portion can have a concave distal surface. Each lateral-facing recessed portion can have a first planar surface, a second planar surface substantially perpendicular to the first planar surface, and a curved surface therebetween.

In some embodiments, the proximal ends of the spaced apart arms can lie along a common circular circumferential path.

In certain embodiments, the assembly can include a drag ring disposed within the receiver member, the drag ring configured to exert a friction force on the head portion of the bone anchor.

In some embodiments, the assembly can include a compression member disposed within the receiver member, wherein a proximal portion of the compression member includes opposing planar surfaces that are angularly offset from one another forming a seat for receiving a spinal fixation element. Material displaced in the formation of the second recesses can be configured to restrict movement of the compression member relative to the receiver member. The displaced material can be received within corresponding recesses formed in the compression member.

In certain embodiments, the assembly can include a pair of reduction tabs extending proximally from the pair of spaced apart arms.

In some embodiments, the assembly can include a fixation element with external square threads configured to be received between the spaced apart arms of the receiver member.

In certain embodiments, the bone anchor can include a bore extending proximally from a distal tip of the bone engaging portion. The bore can extend through an entire length of the bone anchor. The bore can be a blind bore.

In some embodiments, the distal bone-engaging portion can include external threads that extend distally along the bone-engaging portion to a distal tip thereof.

In another aspect, a bone anchor assembly is disclosed that includes a bone anchor having a proximal head portion and a distal threaded bone-engaging portion. The assembly further includes a receiver member having a proximal end defined by a pair of spaced apart arms forming a U-shaped recess configured to receive a spinal fixation element therebetween and a distal end having a polyaxial seat formed therein for polyaxially seating the head portion of the bone anchor. Moreover, proximal ends of the spaced apart arms lie along a common circular circumferential path.

Any of a variety of alternative or additional features can be included and are considered within the scope of the present disclosure. For example, in some embodiments, the receiver member can include a groove formed in an outer surface of each of the spaced apart arms at a proximal end thereof, a first recess formed in the outer surface of each arm with at least a portion of the first recess intersecting the groove, and a second recess formed in an outer surface of the receiver member at a position distal to the first recesses. The first recesses and the second recesses can be configured to couple to a surgical instrument. At least a portion of the first recess in each arm can extend proximally beyond the groove. Each of the second recesses can be longitudinally aligned with one of the first recesses. The first recesses can be configured to pivotably couple to a surgical instrument. The pair of second recesses can be configured to pivotably couple to a surgical instrument.

In some embodiments, the U-shaped recess can be configured to receive a spinal fixation element of various sizes.

In certain embodiments, each spaced apart arm can have a laterally-facing recessed portion formed on opposite lateral edges of the arm, each of the lateral-facing recessed portions facing away from a central proximal-distal axis of the receiver member, wherein the lateral-facing recessed portions are configured to engage with a surgical instrument such that the U-shaped recess remains unobstructed. Each of the lateral-facing recessed portions can extend distally from the proximal end of the spaced apart arms. Each lateral-facing recessed portion can have a concave distal surface. Each lateral-facing recessed portion can have a first planar surface, a second planar surface substantially perpendicular to the first planar surface, and a curved surface therebetween.

In some embodiments, opposing laterally-facing sides of the receiver member can taper inward towards the proximal end of the receiver member. A first pair of opposed sides of the receiver member can have a first taper with respect to a first plane that contains a proximal-distal axis of the receiver member. A second pair of opposed sides of the receiver member can have a second taper with respect to a second plane that contains the proximal-distal axis and is offset from the first plane. The first plane can be perpendicular to the second plane.

In certain embodiments, the assembly can include a drag ring disposed within the receiver member, the drag ring configured to exert a friction force on the head portion of the bone anchor.

In some embodiments, the assembly can include a compression member disposed within the receiver member, wherein a proximal portion of the compression member includes opposing planar surfaces that are angularly offset from one another forming a seat for receiving a spinal fixation element. Material displaced in the formation of the second recesses can be configured to restrict movement of the compression member relative to the receiver member. The displaced material can be received within corresponding recesses formed in the compression member.

In certain embodiments, the assembly can include a pair of reduction tabs extending proximally from the pair of spaced apart arms.

In some embodiments, the assembly can include a fixation element with external square threads configured to be received between the spaced apart arms of the receiver member.

In certain embodiments, the bone anchor can include a bore extending proximally from a distal tip of the bone engaging portion. The bore can extend through an entire length of the bone anchor. The bore can be a blind bore.

In some embodiments, the distal bone-engaging portion can include external threads that extend distally along the bone-engaging portion to a distal tip thereof.

In another aspect, a bone anchor assembly is disclosed that includes a bone anchor having a proximal head portion, a distal bone-engaging portion with external threads that extend to a distal tip of the bone anchor, and a bore centered within the distal bone-engaging portion extending proximally from the distal tip of the bone anchor. The assembly further includes a receiver member having a proximal end defined by a pair of spaced apart arms forming a U-shaped recess configured to receive a spinal fixation element therebetween and a distal end having a polyaxial seat formed therein for polyaxially seating the head portion of the bone anchor.

Any of a variety of alternative or additional features can be included and are considered within the scope of the present disclosure. For example, in some embodiments, the receiver member can include a groove formed in an outer surface of each of the spaced apart arms at a proximal end thereof, a first recess formed in the outer surface of each arm with at least a portion of the first recess intersecting the groove, and a second recess formed in an outer surface of the receiver member at a position distal to the first recesses. The first recesses and the second recesses can be configured to couple to a surgical instrument. At least a portion of the first recess in each arm can extend proximally beyond the groove. Each of the second recesses can be longitudinally aligned with one of the first recesses. The first recesses can be configured to pivotably couple to a surgical instrument. The pair of second recesses can be configured to pivotably couple to a surgical instrument.

In some embodiments, the U-shaped recess can be configured to receive a spinal fixation element of various sizes.

In certain embodiments, each spaced apart arm can have a laterally-facing recessed portion formed on opposite lateral edges of the arm, each of the lateral-facing recessed portions facing away from a central proximal-distal axis of the receiver member, wherein the lateral-facing recessed portions are configured to engage with a surgical instrument such that the U-shaped recess remains unobstructed. Each of the lateral-facing recessed portions can extend distally from the proximal end of the spaced apart arms. Each lateral-facing recessed portion can have a concave distal surface.

In some embodiments, the proximal ends of the spaced apart arms can lie along a common circular circumferential path.

In some embodiments, opposing laterally-facing sides of the receiver member can taper inward towards the proximal end of the receiver member. A first pair of opposed sides of the receiver member can have a first taper with respect to a first plane that contains a proximal-distal axis of the receiver member. A second pair of opposed sides of the receiver member can have a second taper with respect to a second plane that contains the proximal-distal axis and is offset from the first plane. The first plane can be perpendicular to the second plane.

In certain embodiments, the assembly can include a drag ring disposed within the receiver member, the drag ring configured to exert a friction force on the head portion of the bone anchor.

In some embodiments, the assembly can include a compression member disposed within the receiver member, wherein a proximal portion of the compression member includes opposing planar surfaces that are angularly offset from one another forming a seat for receiving a spinal fixation element. Material displaced in the formation of the second recesses can be configured to restrict movement of the compression member relative to the receiver member. The displaced material can be received within corresponding recesses formed in the compression member.

In certain embodiments, the assembly can include a pair of reduction tabs extending proximally from the pair of spaced apart arms.

In another aspect, a bone anchor assembly is disclosed that includes a bone anchor having a proximal head portion, a distal bone-engaging portion with external threads that extend to a distal tip of bone anchor, and a bore centered within the distal bone-engaging portion extending proximally from the distal tip of the bone anchor. The assembly also includes a receiver member having a proximal end defined by a pair of spaced apart arms forming a U-shaped recess therebetween, a distal end having a polyaxial seat formed therein for polyaxially seating the head portion of the bone anchor, a groove formed in an outer surface of each of the spaced apart arms at a proximal end thereof, a first recess formed in the outer surface of each arm with at least a portion of the first recess intersecting the groove, and a second recess formed in an outer surface of the receiver member at a position distal to the first recesses. The assembly further includes a drag ring disposed within the receiver member, the drag ring configured to exert a friction force on the head portion of the bone anchor. The assembly further includes a compression member disposed within the receiver member, wherein a proximal portion of the compression member includes opposing planar surfaces that are angularly offset from one another forming a seat for receiving a spinal fixation element. Moreover, the first recesses and the second recesses of the receiver member are configured to couple to a surgical instrument. Further, each spaced apart arm has a laterally-facing recessed portion formed on opposite lateral edges of the arm, each of the lateral-facing recessed portions facing away from a central proximal-distal axis of the receiver member, wherein the lateral-facing recessed portions are configured to engage with a surgical instrument such that the U-shaped recess remains unobstructed. Still further, opposing laterally-facing sides of the receiver member taper inward towards the proximal end of the receiver member.

Any of a variety of alternative or additional features can be included and are considered within the scope of the present disclosure. For example, in some embodiments, the proximal ends of the spaced apart arms can lie along a common circular circumferential path. And in certain embodiments, the compression member can be locked against removal from an interior of the receiver member.

In another aspect, a bone anchor assembly is disclosed that includes a bone anchor having a proximal portion and a distal threaded bone-engaging portion, as well as a locking sphere configured to couple to the proximal portion of the bone anchor. The assembly further includes a receiver member having a proximal end defined by a pair of spaced apart arms forming a U-shaped recess therebetween, and a distal end having a polyaxial seat formed therein for polyaxially seating the locking sphere, as well as a drag ring disposed within the receiver member and configured to exert a friction force on the locking sphere, and a compression member disposed within the receiver member. Moreover, a distal facing surface of the receiver member is obliquely angled relative to a central proximal-distal axis of the receiver member to provide a greater degree of angulation of the bone anchor relative to the receiver member in a first direction relative to a second, opposite direction.

Any of a variety of alternative or additional features can be included and are considered within the scope of the present disclosure. For example, in some embodiments, the receiver member can include a groove formed in an outer surface of each of the spaced apart arms at a proximal end thereof. Further, the receiver member can include a first recess formed in the outer surface of each arm with at least a portion of the first recess intersecting the groove, and a second recess formed in an outer surface of the receiver member at a position distal to the first recesses. Moreover, the first and second recesses can be configured to couple to a surgical instrument. In some embodiments, At least a portion of the first recess in each arm extends proximally beyond the groove. The second recess can be longitudinally aligned with one of the first recesses. The first recesses can be configured to pivotably couple to a surgical instrument. The second recess can be configured to pivotably couple to a surgical instrument as well.

In certain embodiments, the U-shaped recess can be configured to receive a spinal fixation element of various sizes.

In some embodiments, each spaced apart arm can have a laterally-facing recessed portion formed on opposite lateral edges of the arm, each of the lateral-facing recessed portions facing away from the central proximal-distal axis of the receiver member, wherein the lateral-facing recessed portions are configured to engage with a surgical instrument such that the U-shaped recess remains unobstructed. Each of the lateral-facing recessed portions can extend distally from the proximal end of the spaced apart arms. Each lateral-facing recessed portion can have a concave distal surface. Each lateral-facing recessed portion can have a first planar surface, a second planar surface substantially perpendicular to the first planar surface, and a curved surface therebetween.

In certain embodiments, the proximal ends of the spaced apart arms can lie along a common circular circumferential path.

In some embodiments, opposing laterally-facing sides of the receiver member can taper inward towards the proximal end of the receiver member. A first pair of opposed sides of the receiver member can have a first taper with respect to a first plane that contains a proximal-distal axis of the receiver member. A second pair of opposed sides of the receiver member can have a second taper with respect to a second plane that contains the proximal-distal axis and is offset from the first plane. The first plane can be perpendicular to the second plane.

In certain embodiments, a proximal portion of the compression member can include opposing planar surfaces that are angularly offset from one another forming a seat for receiving a spinal fixation element. Material displaced in the formation of the second recess can be configured to restrict movement of the compression member relative to the receiver member. The displaced material can be received within a corresponding recess formed in the compression member.

In some embodiments, the assembly can include a pair of reduction tabs extending proximally from the pair of spaced apart arms.

In certain embodiments, the assembly can include a fixation element with external square threads configured to be received between the spaced apart arms of the receiver member.

In some embodiments, the bone anchor can include a bore extending proximally from a distal tip of the bone engaging portion. The bore can extend through an entire length of the bone anchor. The bone anchor can include at least one outlet formed in a lateral surface thereof that intersects with the bore. The bore can be a blind bore.

In certain embodiments, the distal bone-engaging portion can include external threads that extend distally along the bone-engaging portion to a distal tip thereof.

In some embodiments, the compression member can be configured to exert a force on the locking sphere upon distal advancement of the compression member relative to the receiver member.

In certain embodiments, the bone anchor can include threads of a first pitch formed along a first bone-engaging portion thereof and threads of a second pitch formed along a second bone-engaging portion that is proximal of the first bone engaging portion. The first pitch can be greater than the second pitch.

In some embodiments, the bone anchor can include threads formed on a first, distal portion thereof and a second portion without threads that is disposed between the first portion and the proximal portion of the bone anchor. Moreover, a length of the second portion without threads can be at least about 30% of a length of the first portion having threads formed thereon. The length of the second portion can also be between about 30% and about 90% of the length of the first portion.

Any of the features or variations described herein can be applied to any particular aspect or embodiment of the present disclosure in a number of different combinations. The absence of explicit recitation of any particular combination is due solely to avoiding unnecessary length or repetition.

BRIEF DESCRIPTION OF THE DRAWINGS

The aspects and embodiments of the present disclosure can be more fully understood from the following detailed description taken in conjunction with the accompanying drawings, in which:

FIG. 23 is a perspective longitudinal cross-sectional view of the bone anchor assembly of FIG. 20;

FIG. 24 is an enlarged partially transparent perspective view of the proximal portion of the bone anchor assembly of FIG. 20;

FIG. 33 is a partially transparent side view of the proximal portion of the receiver member of the bone anchor assembly of FIG. 20;

FIG. 34A is a perspective view of a bone shank of the bone anchor assembly of FIG. 20;

FIG. 34B is a partially transparent view of FIG. 34A;

DETAILED DESCRIPTION

Certain example embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure. Additionally, to the extent that linear, circular, or other dimensions are used in the description of the disclosed devices and methods, such dimensions are not intended to limit the types of shapes that can be used in conjunction with such devices and methods. Equivalents to such dimensions can be determined for different geometric shapes, etc. Further, like-numbered components of the embodiments can generally have similar features. Still further, sizes and shapes of the devices, and the components thereof, can depend at least on the anatomy of the subject in which the devices will be used, the size and shape of objects with which the devices will be used, and the methods and procedures in which the devices will be used.

The bone anchor assemblies disclosed herein, and methods related to the same, provide for a single bone anchor assembly that can be utilized across a range of spinal surgical procedures, reduce manufacturing burden and cost, and provide for greater flexibility during a surgical procedure. The bone anchor assemblies disclosed herein include an implantable shank and a receiver member having two spaced apart arms which form a U-shaped seat to receive a rod, among other components. The bone anchor assemblies disclosed herein also provide a number of features to enhance capability and usability. These include, for example, features to facilitate better implantation of the shank, better coupling of instrumentation to the anchor, better performance in reducing a spinal fixation element, such as a rod, into the receiver member seat, and others.

Figure 1:
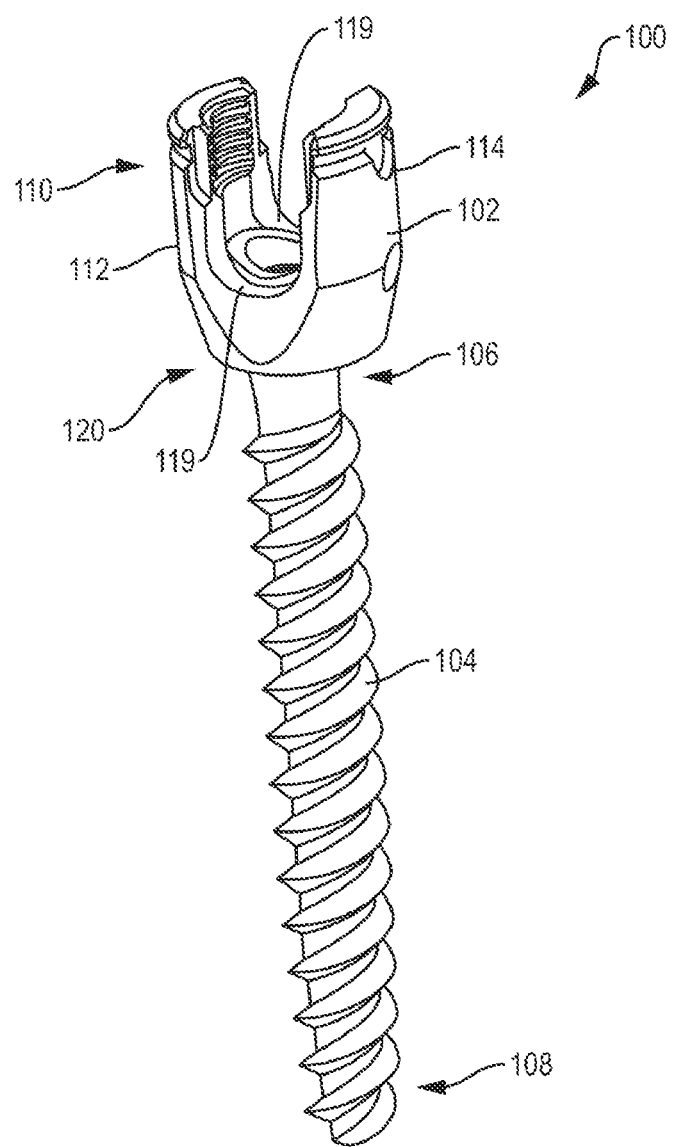
FIG. 1 is a perspective view of a bone anchor assembly, according to one embodiment.

FIG. 1 illustrates a perspective view of one embodiment of a bone anchor assembly 100 of the present disclosure. The bone anchor assembly can include a receiver member 102 and a bone shank 104 having a proximal head portion 106 and a distal bone-engaging portion 108. The receiver member 102 can have a proximal portion 110 defined by a pair of spaced apart arms 112 and 114 forming a U-shaped recess 119 (also referred to as a rod-receiving recess or slot) therebetween to receive a spinal fixation element (not shown), such as a spinal rod. A polyaxial seat 608 (see FIG. 6) is formed in a distal end 120 of the receiver member 102 for polyaxially seating the head portion 302 (shown in FIG. 2 and FIG. 3) of the bone shank 104. As discussed in detail below, the receiver member 102 can have multiple distinct engagement or attachment features to facilitate coupling of the receiver member 102 to surgical instruments during use.

Figure 2:
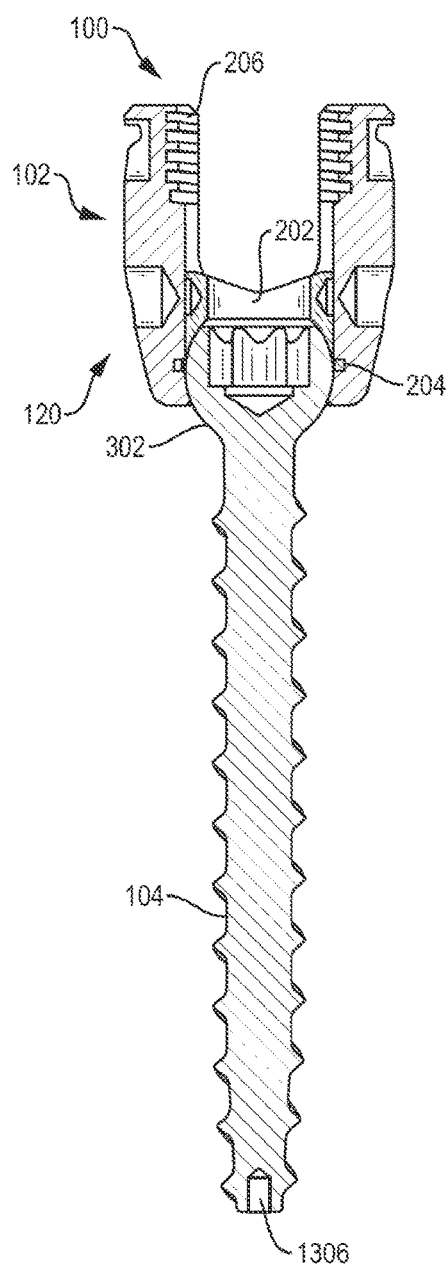
FIG. 2 is a cross-sectional view of the bone anchor assembly of FIG. 1.
Figure 3:
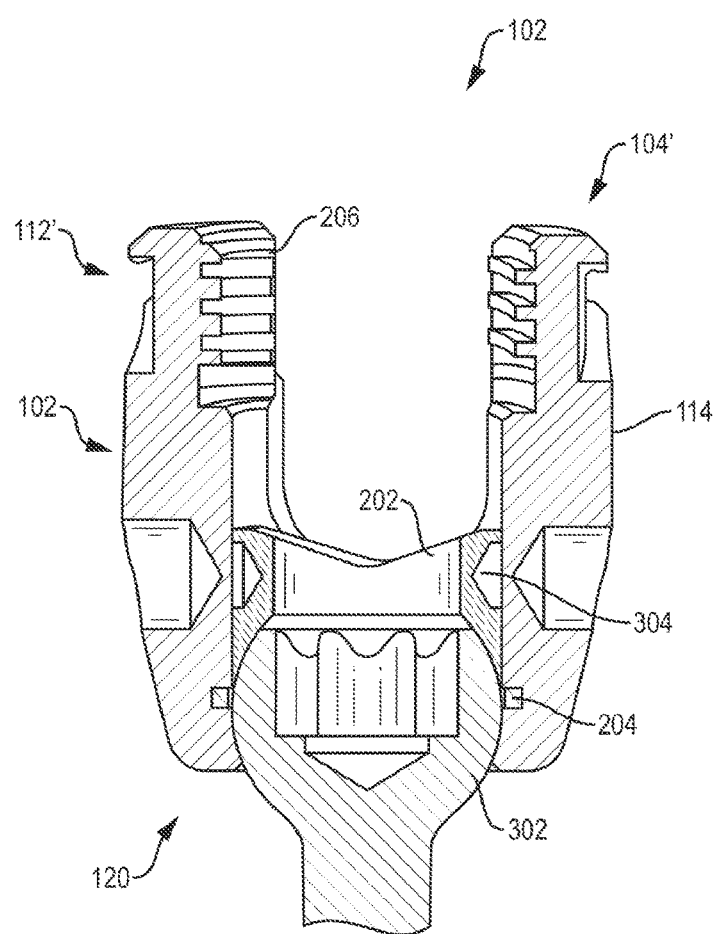
FIG. 3 is an enlarged cross-sectional view of a proximal portion of the bone anchor assembly of FIG. 1.

FIG. 2 is a cross-sectional view of the bone anchor assembly 100 of FIG. 1, and FIG. 3 is an enlarged cross-sectional view of the receiver member 102. As shown in FIG. 2, the bone anchor assembly 100 can further include a compression cap 202 and a drag ring 204 disposed within the distal end 120 of the receiver member 102. The compression cap 202 and drag ring 204 can contact the proximal head 302 of the shank 104. FIG. 3 illustrates that the proximal head 302 of the shank 104 seated in the distal end 120 of the receiver member 102.

Figure 4:
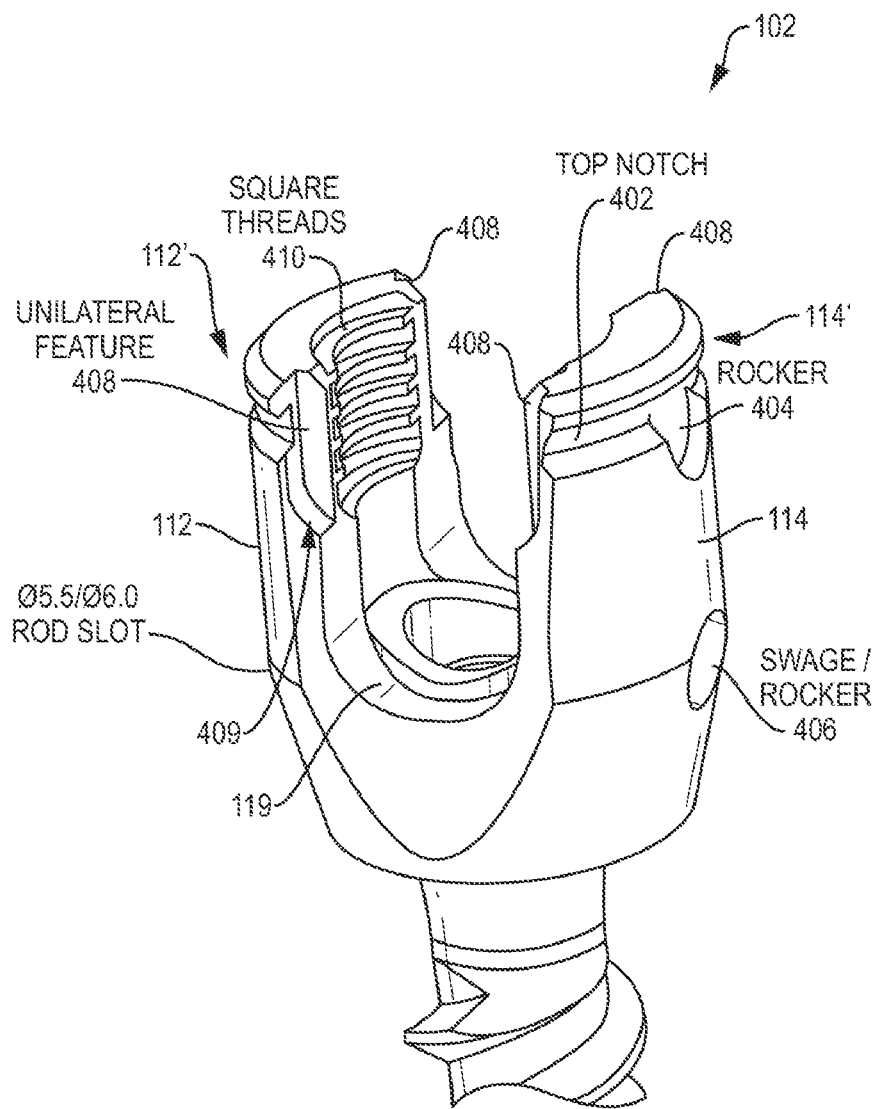
FIG. 4 is an enlarged prospective view of the proximal portion of the bone anchor assembly of FIG. 1.

FIG. 4 is an enlarged perspective partial view of the bone anchor assembly 100 of FIG. 1, highlighting particular elements or features of the receiver member 102 that are discussed in detail below. Receiver members of the present disclosure can include any of the features discussed herein, taken alone or in combination with one another. For example, the receiver member 102 can include one or more features to facilitate engagement of a surgical instrument with the bone anchor assembly 100. A groove or a channel 402 can be formed in an outer surface at the proximal end 112', 114' of each of the spaced apart arms 112, 114. The groove or channel 402 can define a "top-notch" feature that can be engaged with a corresponding portion of an instrument, such as a projection, to facilitate coupling of the instrument to the receiver member 102. Additional details regarding such a feature can be found in U.S. Pat. Nos. 10,039,578 and 10,299,839, the entire contents of which are incorporated by reference herein.

FIG. 4 also shows a proximal rocker feature (also referred to as a first recess) 404 formed in the proximal portion 110 of the receiver member 102 that can be used to facilitate reducing a rod (not shown) distally into the U-shaped recess 119 of the receiver member 102. The proximal rocker reducer feature 404 can allow a rocker instrument to pivotably couple to the receiver member 102 for reduction of a spinal fixation element in the receiver member 102 using a levering or rocking motion. The proximal rocker feature 404 can be a bilateral circular detail or recess that intersects the top-notch feature 402, described above. In other words, each of the spaced apart arms 112, 114 can include a proximal rocker feature 404 that intersects with the groove or channel 402 formed at a proximal end 112', 114' of the arm 112, 114. A portion of the proximal rocker feature 404 can extend proximally of the groove 402, intersecting material of the spaced apart arms 112, 114 above the groove 402 (see FIG. 9). This can provide stronger contact between the receiver member 102 and a surgical instrument, and reduce variability in manufacturing of the receiver members.

Additionally or alternatively, the receiver member 102 can include a distal rocker feature (also referred to as a second recess) 406. The distal rocker feature 406 can be formed in the receiver member 102 at a position distal to the proximal rocker feature 404. The second rocker feature 406 can provide an alternative coupling position for a rocker instrument, such as a reducer rocker fork, to the proximal/first rocker feature 404. The second rocker feature 406 can also be a swage feature used to retain a compression cap 202 within the receiver member 102. During assembly, for example, a swaging process can form the second rocker feature 406 and displace receiver member 102 material into a recess 304 formed in the compression cap (also referred to as a compression member) (see FIG. 3) to constrain the compression cap 202 within the receiver member 102 and prevent, e.g., its removal out the proximal end 110 of the receiver member 102. The second rocker feature 406 can be formed on opposing sides of the receiver member 102 and material in each arm 112, 114 of the receiver member 102 can be displaced by swaging into the recesses 304 formed on opposing sides of the compression cap 202. This material displacement into the compression cap 202 can assist in holding the bone anchor assembly 100 together and prevent disassembly of the compression cap 202, bone anchor shank 104, and receiver member 102.

Figure 17:
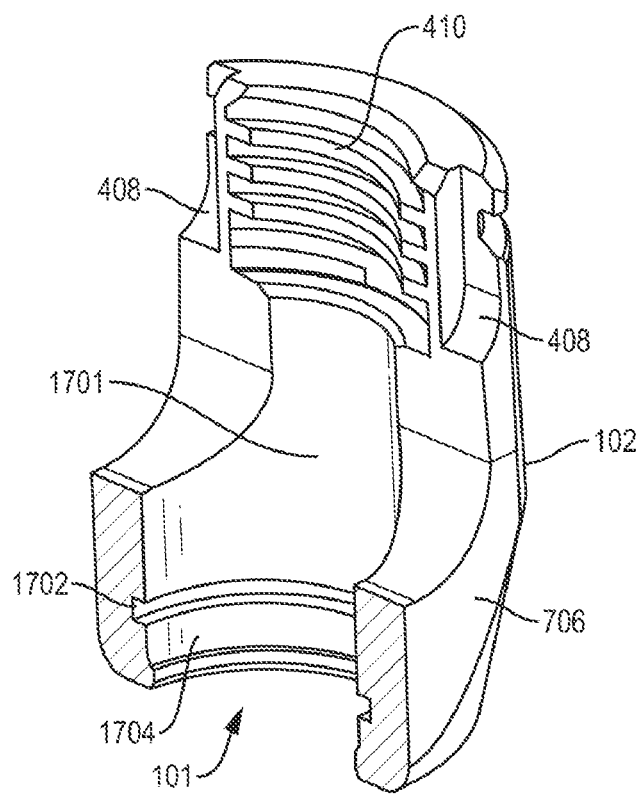
FIG. 17 is a perspective cross-sectional view bisecting the receiver member of the bone anchor assembly of FIG. 1.

As shown in FIG. 4, the receiver member 102 can include at least one unilateral attachment feature 408 that can enable a surgical instrument to couple to or engage with the receiver member 102 in a manner that leaves the rod-receiving slot 119 unobstructed, e.g., by allowing attachment of an instrument to the receiver member 102 by engaging only one arm 112, 114 of the receiver member 102. In one embodiment, the receiver member 102 can include a unilateral attachment feature 408 on four proximal quadrants of the receiver member 102. For example, a unilateral attachment feature can be formed on opposing laterally-facing edges of each of the spaced apart arms 112, 114. A surgical instrument can attach to two adjacent unilateral features 408 on one side of the receiver member 102, leaving the rod-receiving slot 119 open to receive a spinal fixation rod and/or set screw introduced distally from the proximal end 110 of the receiver member 102. This can allow for manipulation of the receiver member 102, attachment of a reduction instrument, and/or insertion of a spinal fixation element or locking element into the rod-receiving slot 119. As shown in FIGS. 4 and 17, each lateral-facing recessed portion 408 can have a concave distal surface 409. In some embodiments, such as that shown in FIG. 59, each unilateral attachment feature 408 can have a planar distal surface 5711 having approximately a 90 degree angle with a sidewall surface 5713, with a concave surface therebetween having a smaller radius than the surface 409. Such a configuration can provide additional planar bracing surfaces for use when coupling with an instrument Additional details pertaining to unilateral attachment feature(s) can be found in U.S. Patent Application Publication No. 2019/0183541, entitled "Unilateral Implant Holders and Related Methods," the entire contents of which are incorporated by reference herein.

As indicated in FIG. 4 and discussed in detail below with respect to FIGS. 10-12, the receiver member 102 can receive spinal fixation elements of multiple sizes. For example, spinal rods having a diameter of about 5.5 mm or a diameter of about 6.0 mm can be received within the rod-receiving recess 119. A proximal portion of the spaced apart arms 112, 114 of the receiver member 102 can include a threaded inner surface 410 that can engage with a set screw or other locking element received therebetween to lock a spinal rod within the receiver member 102. In some embodiments, the inner threaded portion 410 can have square threads e.g., to engage with counterpart external square threads of a set screw (see FIG. 14).

Figure 5:
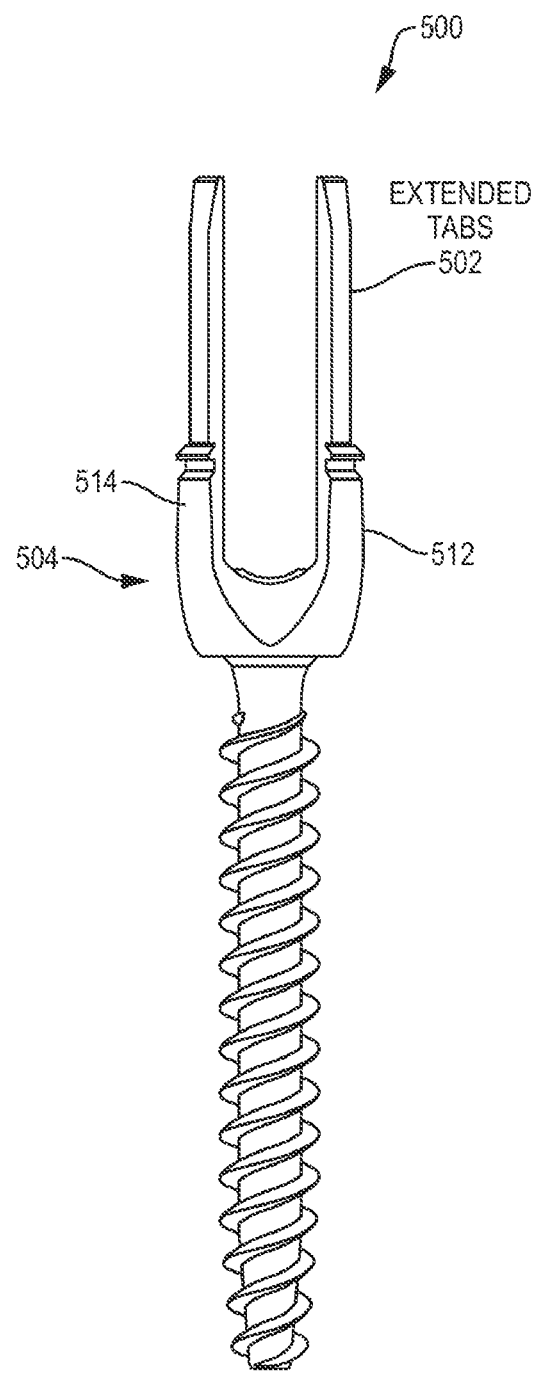
FIG. 5 is a side view of one embodiment of a bone anchor assembly.

FIG. 5 is a front view of another embodiment of a bone anchor assembly 500 of the present disclosure with reduction tabs 502 extending proximally from the spaced apart arms 512, 514 of the receiver member 504. The bone anchor assembly 500 of FIG. 5 can include any of the features described herein.

Figure 6:
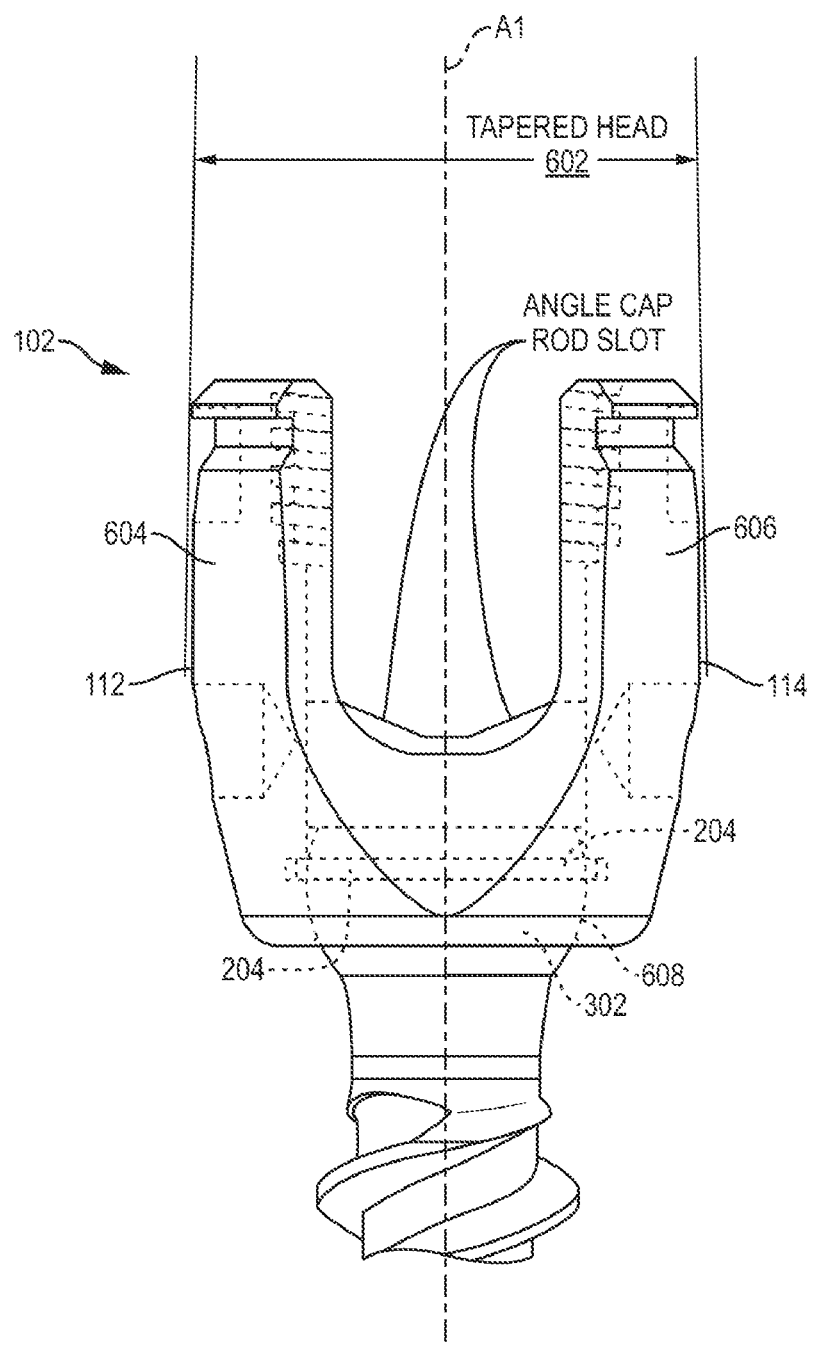
FIG. 6 is a partially transparent front view of the proximal portion of the bone anchor assembly of FIG. 1.
Figure 60:
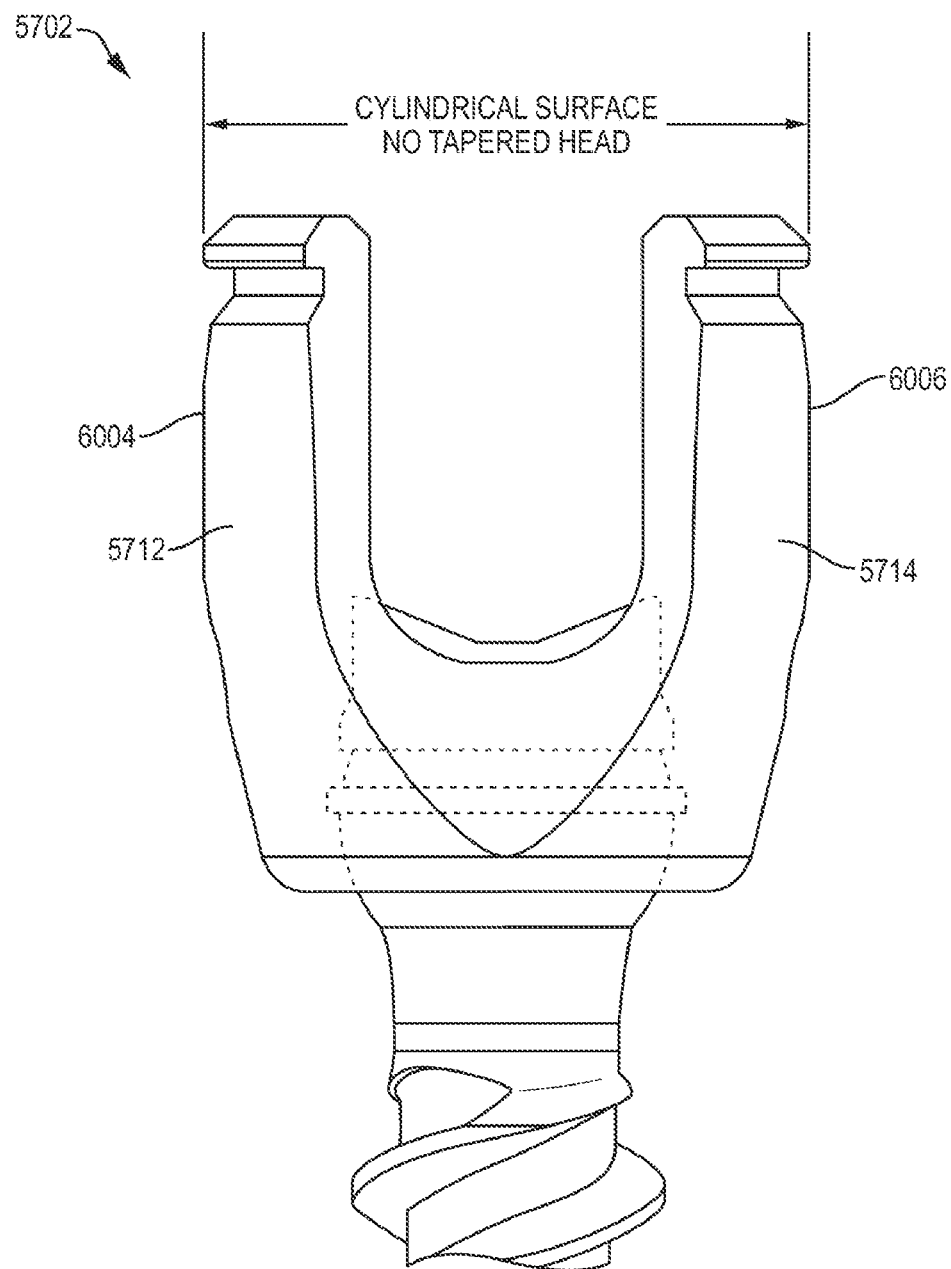
FIG. 60 is a partially-transparent front view of the bone anchor assembly of FIG. 60.

Bone anchor assemblies 100, 500 of the present disclosure can include a receiver member 102, 504 having a taper in one or more directions. FIG. 6 is a partially transparent view of the bone anchor assembly 100 of FIG. 1 that shows, among other things, a taper 602 of the outer surface of the receiver member 102 in a first direction. More particularly, a first pair of opposed sides 604, 606, shown in FIG. 6 as exterior walls of the spaced-apart arms 112, 114, can have a first taper with respect to a first plane that contains a proximal-distal axis A1 of the receiver member 102 (i.e., the plane of the page of FIG. 6). Alternatively, FIG. 60 shows an embodiment of a receiver member 5702 in which a first pair of opposed sides 6004, 6006, do not have a taper with respect to the first plane that contains a proximal-distal axis A1 of the receiver member. That is, the opposed sides 6004, 6006 of exterior walls of the spaced-apart arms 5712, 5714 have a substantially straight cylindrical shape.

Figure 7:
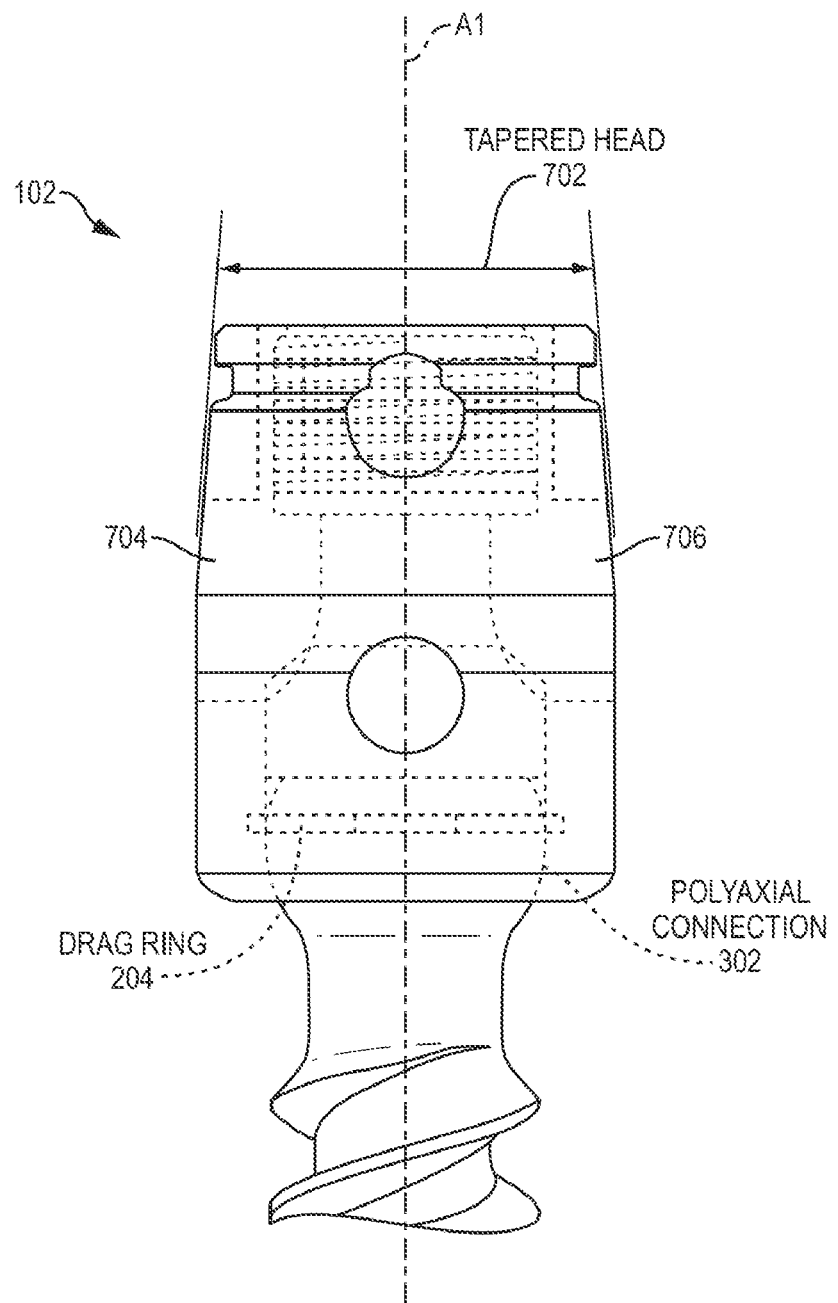
FIG. 7 is a partially transparent side view of the proximal portion of the bone anchor assembly of FIG. 1 in an orientation that is 90 degrees offset from the orientation shown in FIG. 6.
Figure 8:
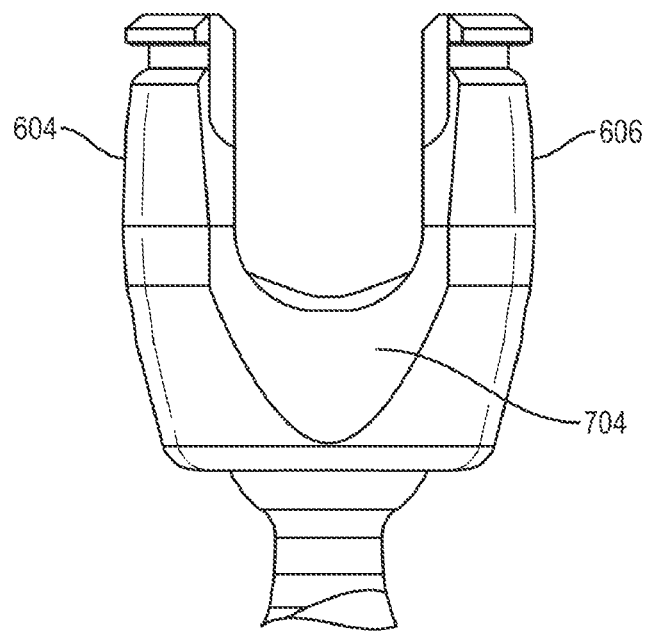
FIG. 8 is a front view of the proximal portion of the bone anchor assembly of FIG. 1 in the orientation shown in FIG. 6.
Figure 9:
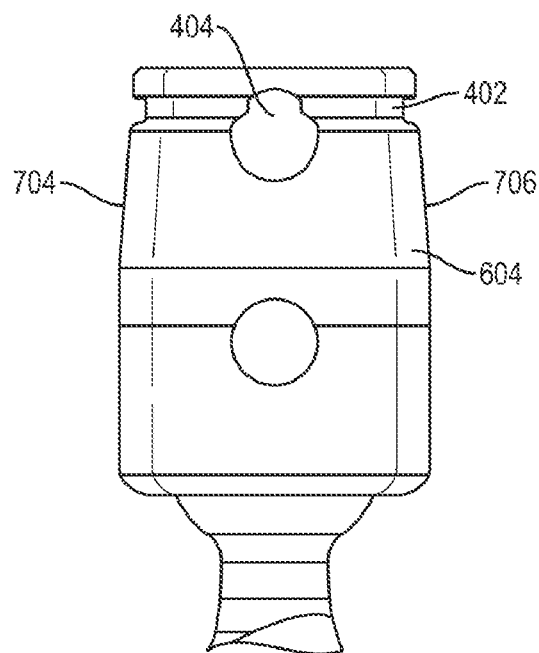
FIG. 9 is a side view of the bone anchor assembly of FIG. 1 in the orientations shown in FIG. 7.

FIG. 7 is a partially transparent side view of the bone anchor assembly 100 of FIG. 1 in an orientation that is 90 degrees offset from the orientation shown in FIG. 6. FIG. 7 illustrates, among other things, a taper 702 of the outer surface of the receiver member 102 in a second direction. More particularly, a second pair of opposed sides 704, 706, shown in FIG. 7 as exterior walls of the receiver member 120 that are 90 degrees offset from the first pair of opposed sides 604, 606, can have a second taper with respect to a second plane (i.e., the plane of the page of FIG. 7). The second plane contains the proximal-distal axis A1 of the receiver member and is offset from the first plane described above. The first plane and the second plane can be perpendicular to one another in some embodiments, though other offset angles are also possible. Accordingly, when implanted into a patient's spine, the receiver member 102 can have walls that taper in both the cephalad-caudal direction and the medial-lateral direction, for example. Taper of the receiver member 102 with respect to two offset planes can aid in instrument attachment to the receiver member 102 as the angled characteristic of the receiver member 102, i.e., the tapering of exterior walls 604, 606, 704, 706 or an outer surface of the receiver member 102 in two directions, can guide surgical instruments to self-center during attachment to the receiver member. In some embodiments, such as the embodiment shown in FIGS. 57-62, the receiver member may only taper in a single direction. Such a configuration can still provide self-centering guidance during attachment of an instrument to the receiver member. FIGS. 8 and 9 are non-transparent front and side views of the bone anchor assembly 100 of FIG. 1 in the orientations shown in FIGS.

6 and 7, respectively. The inwards taper 604, 606, 704, 706 of the receiver member 102 towards the proximal end of the receiver member 102 can likewise be seen in these figures. FIGS. 8 and 9 illustrate that, in some embodiments, the tapering in multiple planes can be achieved using different surface geometries. For example, in the front view of FIG. 8 the surfaces 604, 606 can have a curved shape that creates a conical first taper. The surfaces 704, 706, however, can be planar surfaces angled toward one another to create a second taper. As noted above, in some embodiments only one of these tapers may be utilized. For example, in the embodiment shown in FIGS. 57-62, cylindrical surfaces 6004, 6006 do not taper while planar surfaces 7004, 7006 include a similar taper as surfaces 704, 706 in FIGS. 7 and 9.

Returning to FIGS. 6 and 7, the bone anchor assembly 100 can include a drag ring 204 disposed within a recess or groove 1702 (see FIG. 17) formed in a distal portion 120 of the receiver member 102. The drag ring 204 can create a friction fit between an interior surface 204' of the drag ring 204 and an exterior surface of the shank head 302, such that the receiver member 102 of the bone anchor assembly 100 can provisionally maintain a position relative to the bone shank 104 prior to a full locking of the bone anchor assembly 100, e.g., with a set screw or other locking element. In some embodiments, the drag ring 204 can be disposed within the distal portion 120 of the receiver member 102 prior to insertion of the shank head 302. Further details on drag rings can be found in U.S. Pat. No. 7,087, 057, the entire contents of which are incorporated by reference herein. As noted above, the distal end 120 of the receiver member 102 can include a polyaxial seat 608 for polyaxially seating the head 302 of the bone shank 104. This polyaxial connection can allow full range of motion of the bone shank 104 relative to the receiver member 102. For example, a spherical recess in the distal end 120 of the receiver member 102 (see polyaxial seat 1704 in FIG. 17) can receive a spherical portion of the shank head 302.

Figure 10:
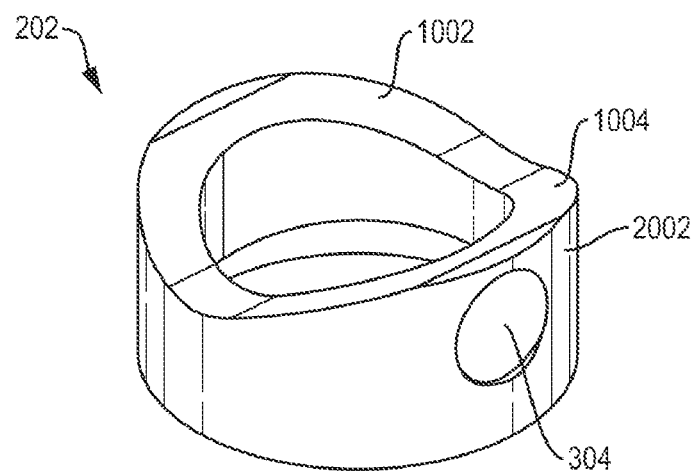
FIG. 10 is a perspective view of a compression cap, according to one embodiment.
Figure 11:
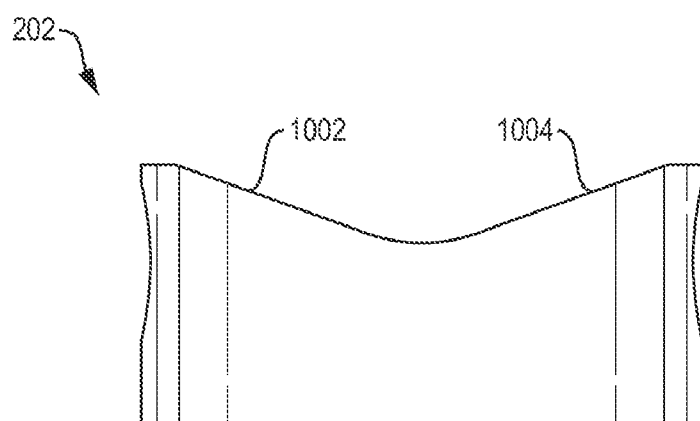
FIG. 11 is a front view of the compression cap of FIG. 10.
Figure 12:
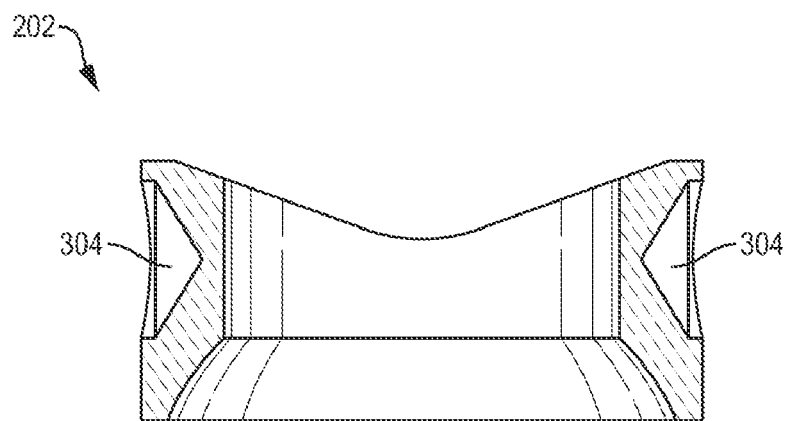
FIG. 12 is a front cross-sectional view of the compression cap as shown in FIG. 11.

FIGS. 10-12 illustrate one embodiment of a compression cap 202 of the present disclosure. FIG. 10 is a perspective view of one embodiment of a compression cap 202, FIG. 11 is a front view of the compression cap 202 of FIG. 10, and FIG. 12 is a cross-sectional view of the compression cap 202 as shown in FIG. 11. As noted above, the outer surface of the compression cap 202 can include depressions or recesses 304 that can receive material from the receiver member 102 that is displaced during a swage that can form the second rocker feature 406. A proximal portion of the compression cap can form a seat for receiving a spinal rod. More particularly, two planar surfaces 1002, 1004 of the compression cap can be angularly offset from one another to form a substantially "V" shaped groove that can seat a spinal rod of varying diameters. This is in comparison to conventional compression caps that often include a curved proximal surface with a radius matching a single spinal rod diameter.

Figure 13D:
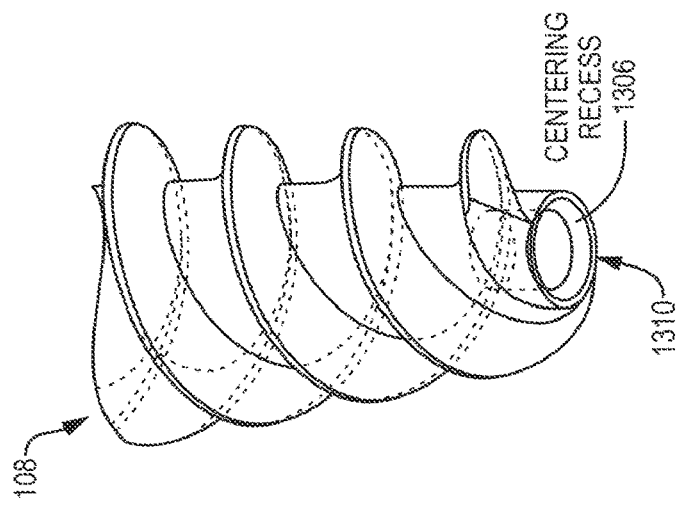
FIG. 13D is a partially-transparent view of FIG. 13C.
Figure 13C:
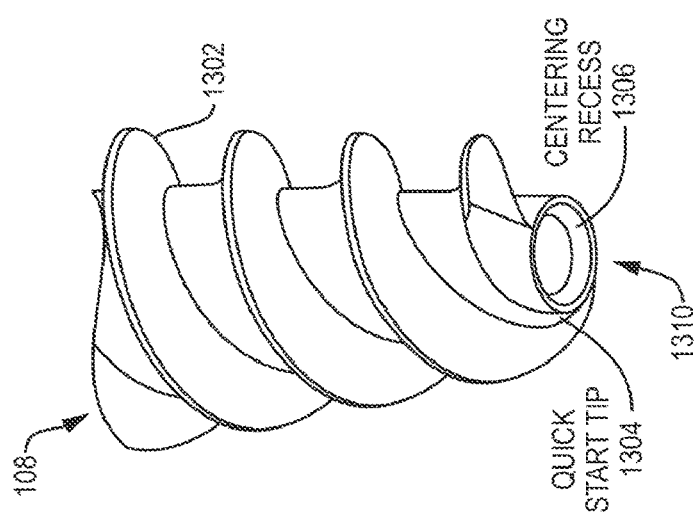
FIG. 13C is a detail perspective view of the distal end of the shank of the bone anchor assembly of FIG. 1.
Figure 13B:
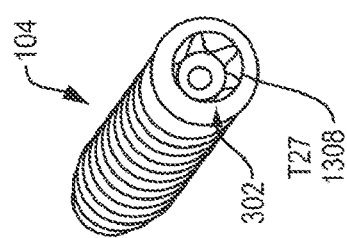
FIG. 13B is a proximal end perspective view of the shank of the bone anchor assembly of FIG. 1.
Figure 13A:
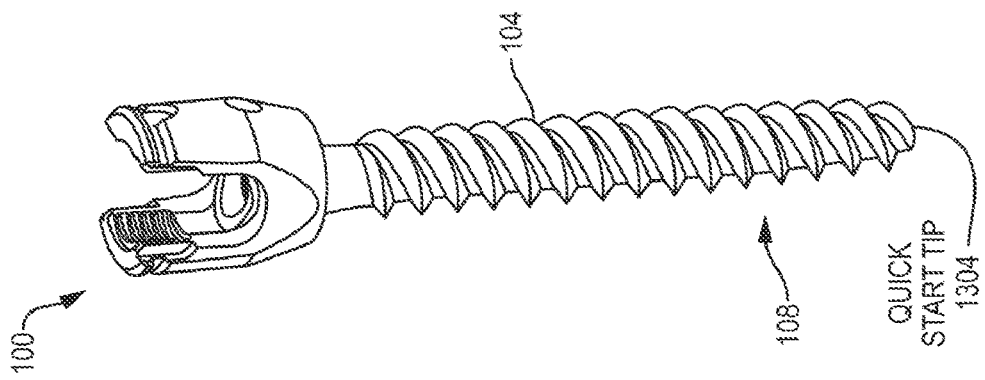
FIG. 13A is a perspective view of the bone anchor assembly of FIG. 1.

FIGS. 13A-13D illustrate various aspects of one embodiment of a bone shank 104 of the present disclosure. FIG. 13A shows the bone anchor assembly 100 of FIG. 1. FIG. 13B shows a top perspective view of the bone shank 104 in isolation. FIG. 13C shows an enlarged view of a distal end of the bone-engaging portion 108 of the bone shank 104. FIG. 13D shows a partially transparent enlarged view of the distal end of the bone-engaging portion 108 of the bone shank 104. External threads 1302 can extend along the bone-engaging portion 108 of the shank 104. Various thread forms can be utilized for shanks of the present disclosure, including solid dual lead, solid cortical fix, cannulated dual lead, cannulated cortical fix, and cannulated cortical fix fenestrated threads. The bone shank 104 can have a quick-start tip 1304, with threads that extend distally to a distal tip 3410 of the bone engaging portion 1310. In this manner, the threads 1302 can extend to the contact surface between the bone shank 104 and the bone (not shown), which can provide immediate purchase of the thread into bone. In many conventional screws, a rounded tip is often used distal to the threads, which can require driving the screw into the bone axially some distance before threads can grip the bone.

A recess 1306 can be centered and formed in the distal tip 1310 of the bone shank 104. This recess 1306, which can be referred to as a centering recess, can be used to support the distal bone-engaging portion 108 of the shank 104 in a centered manner during the manufacturing process. In some embodiments, the centering recess can be a blind bore that extends proximally from the distal tip 1310 of the bone-engaging portion 108 (e.g., as shown in the partially transparent view of FIG. 13D). In other embodiments, the centering recess can be a full cannulated recess that extends from the proximal end to the distal end of the bone shank 104. Such a recess can allow, for example, for introduction of the shank 104 over a guidewire, delivery of cement or other flowable material through the shank 104 into bone, etc. A drive feature 1308 can be formed in the proximal head 302 of the bone shank 104 to allow a driver to control rotation of the anchor during implantation, etc. Any of a variety of drive feature designs can be utilized, including square drive, hex drive, lobed drives, etc. The illustrated embodiment includes a T27 drive feature.

Figure 14:
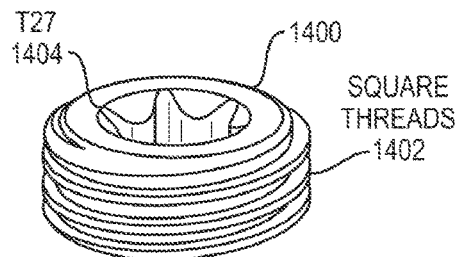
FIG. 14 is a perspective view of a set screw, according to one embodiment.
Figure 15A:
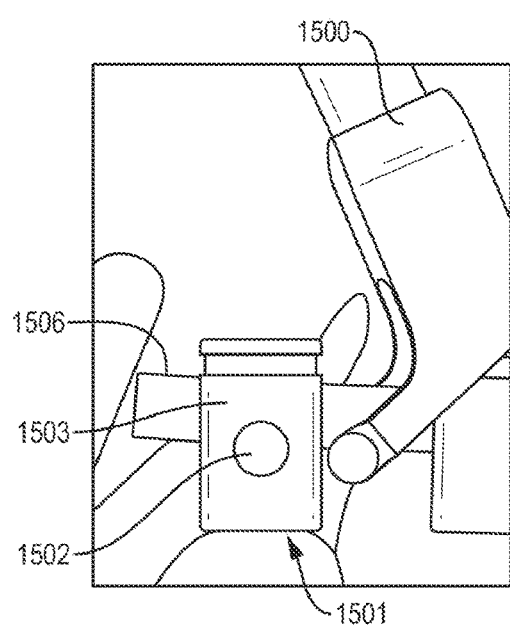
FIG. 15A is an illustration of reducer instrument being introduced to a bone anchor assembly.
Figure 15B:
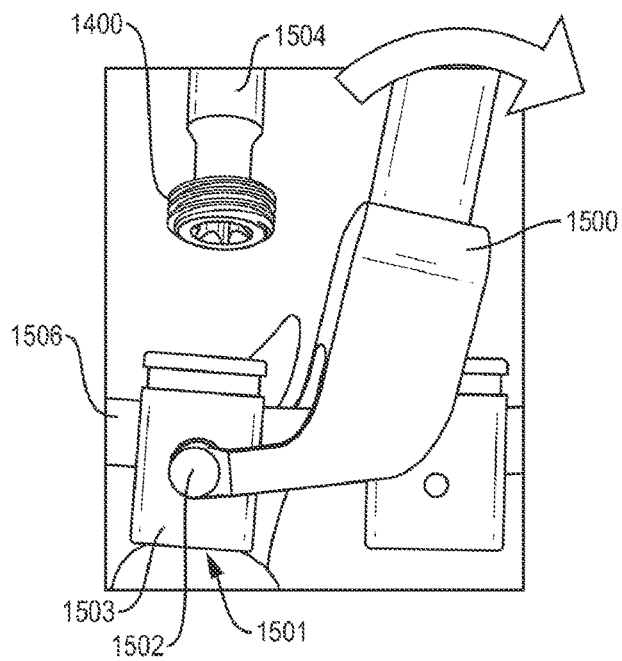
FIG. 15B is an illustration of a reducer instrument holding a rod in a bone anchor assembly and introducing a set screw to lock a position of the rod.

FIG. 14 illustrates one embodiment of a set screw 1400 of the present disclosure. The set screw 1400 and proximal portion of the receiver member 102 inner surface 206 (see FIG. 2) can each have complementary square threads 1402 (or other thread forms) formed thereon. As noted above, the set screw 1400 can have a drive feature 1404 formed therein, such as the above-noted T27 drive feature 1404. FIGS. 15A and 15B illustrate one embodiment of a reducer instrument 1500, in the form of a reducer fork, engaging with a distal rocker feature 1502 of a bone anchor assembly 1501. The reducer instrument 1500 can couple with the receiver member 1503 when the bone anchor assembly 1501 is implanted into bone by engaging the distal rocker features 1502 on either side of the receiver member 1503, e.g., with counterpart projections formed on the arms of the reducer instrument 1500. The reducer instrument 1500 can be pivoted or rocked to move a spinal rod 1506 distally into the recess of the receiver member 1503. Further, the offset of the instrument 1500 from the receiver member 1503 created by the fork arm shape and pivoting motion can leave a proximal end of the receiver member 1503 unobstructed such that a set screw 1400 or other locking element can be inserted using a driver 1504 to lock the spinal rod 1506 to the receiver member 1503.

Figure 16:
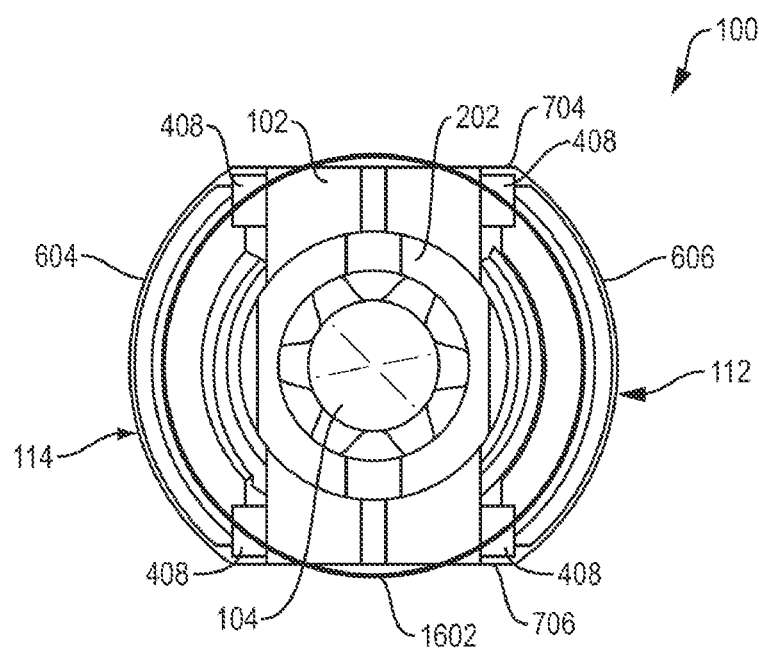
FIG. 16 is a top view of the bone anchor assembly of FIG. 1.

FIGS. 16-19 provide additional detail views of the bone anchor assembly 100. For example, FIG. 16 shows a top or proximal end view of the assembly 100. This figure illustrates that the spaced apart arms 112, 114 of the receiver member 102 generally lie along a circle 1602. For example, each of the unilateral attachment features 408 found at the lateral ends of the spaced apart arms 112, 114 can be positioned an equal distance from the centerline of the assembly, i.e., at a distance equal to the radius of the circle 1602.

FIG. 17 shows a cross-sectional view bisecting the receiver member 102 through the middle of the U-shaped recess 119 formed between the spaced apart arms 112, 114 at the proximal end 110 of the receiver member 102. The figure affords a better view of the interior of the receiver member 102, including two of the unilateral attachment features 408 formed at either lateral end of the receiver member arm 112, threads 410 formed at a proximal end of the interior surface of the arm 112 to receive a set screw, an intermediate unthreaded portion 1701, a groove 1702 that receives the spring clip or drag ring 204, and a polyaxial seat 1704 formed at a distal end 120 of the receiver member 104 that can seat the spherical head 302 of the shank 104.

Figure 18:
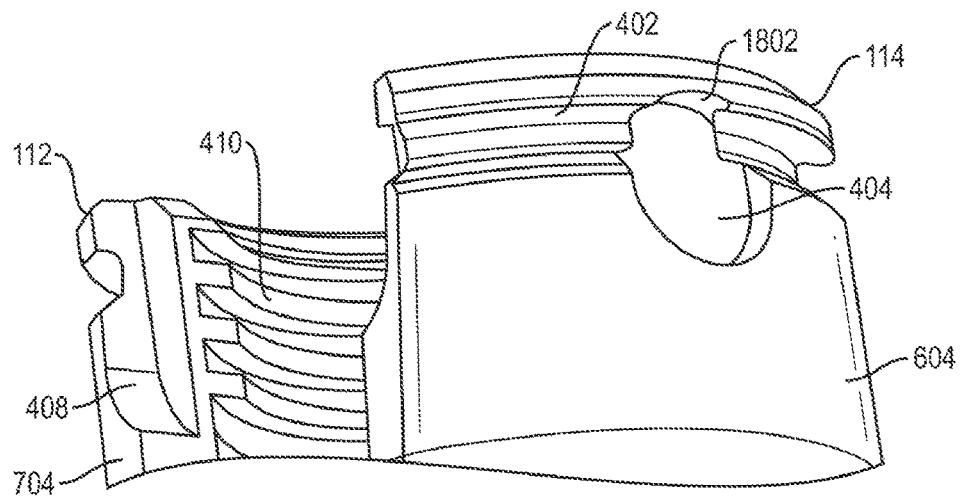
FIG. 18 is a detail perspective view of a proximal portion of the receiver member of the bone anchor assembly of FIG. 1.

FIG. 18 shows a detail view of an exterior proximal portion 110 of the receiver member 102, including the notch or groove 402 formed in an outer sidewall of the spaced apart arms 112, 114 of the receiver member 102, as well as the first rocker feature 404 that intersects the groove 402. Like the groove 402, the first rocker feature 404 is recessed below an outer surface 604 of the arm. Further, the first rocker feature 404 extends proximally above the top or proximal surface of the groove 402, as shown by the arc 1802. The arc 1802 provides a greater surface area for force transfer when coupled to a rocker fork reduction instrument that typically includes cylindrical pins that seat within the first rocker feature recess 404. Without the arc 1802, the cylindrical pin of the rocker fork instrument would make a substantially point or line contact with the substantially planar upper or proximal surface of the groove 402.

Figure 19:
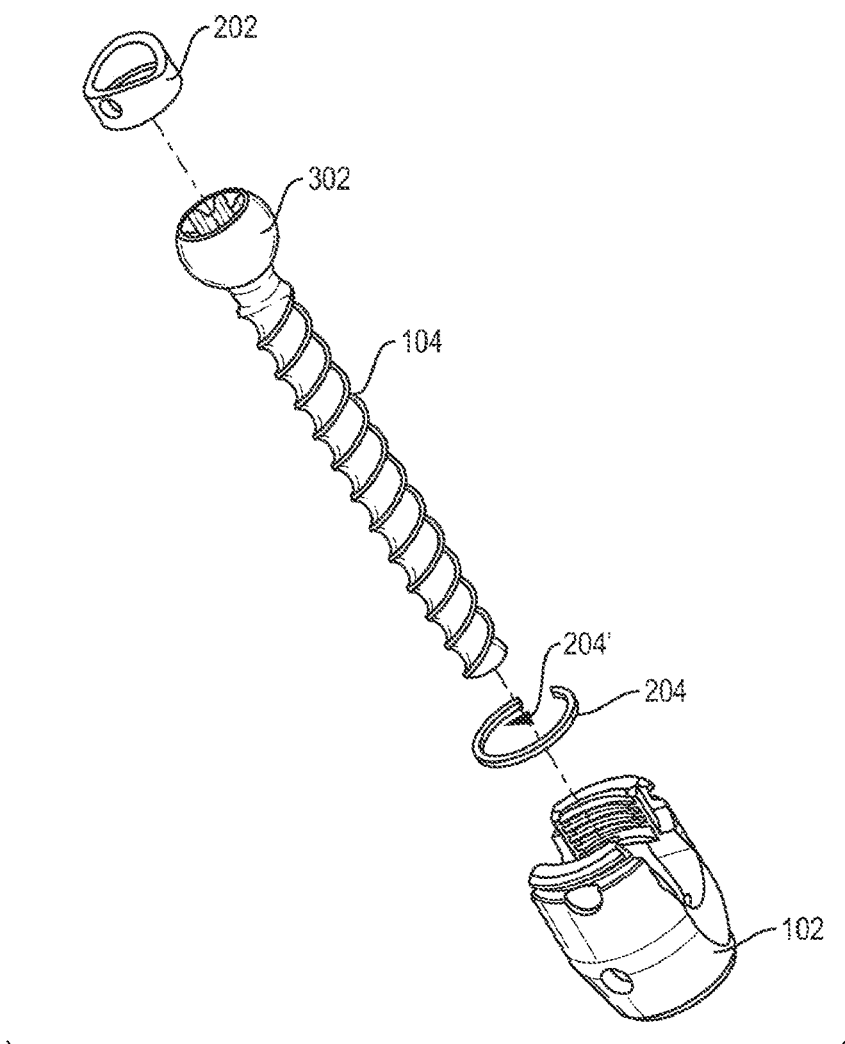
FIG. 19 is an exploded view of the bone anchor assembly of FIG. 1.

FIG. 19 illustrates an exploded view of the bone anchor assembly 100. As shown in the figure, in one embodiment the bone anchor 100 can be assembled by top loading or distally advancing the spring clip or ring 204 relative to the receiver member 102 and allowing the spring clip/ring 204 to expand into the groove 1702. The shank 104 can then be top loaded or advanced distally through the interior of the receiver member 102 such that the distal bone-engaging portion 108 of the shank 104 extends out the through-hole 101 (shown in FIG. 17) formed in the bottom of the receiver member 102, the spherical head 302 of the shank 104 rests in the polyaxial seat 1704 of the receiver member 102, and the drag clip/ring 204 frictionally engages the spherical head 302. The compression cap 202 can also be top loaded or distally advanced into the interior of the receiver member 102, and a swaging operation can be performed to lock the compression cap 202 against removal from the interior of the receiver member 102. Despite being locked against complete removal after swaging, the compression cap 202 can still translate through a range of motion relative to the receiver member 102 and shank 104, such polyaxial movement of the receiver member 102 relative to the shank 104 can be selectively controlled by varying distal force placed on the compression cap 202 that drives it into frictional contact with the proximal end of the bone shank spherical head 302.

FIGS. 20-56 illustrate additional embodiments of bone anchor assemblies according to the present disclosure. These embodiments utilize many of the above-described features but can be configured for use with larger diameter screw shanks. In addition, the receiver members shown in these embodiments can be configured to bias shank angulation to one side or in one direction using a "favored angle" distal portion that allows a greater degree of shank angulation in one direction versus the opposite direction.

The bone anchor assemblies of these embodiments can generally include a receiver member or head, a compression member or cap, a locking sphere, and a shank. The bone anchor assembly can be assembled by inserting the proximal portion of the screw shank up through a distal hole formed in the receiver member. A locking sphere can be dropped into the proximal end of the receiver member and pressed onto the screw shank. The sphere can be locked onto the shank with a rib that fits into a recess inside of the locking sphere. A compression component can be loaded into the receiver member from the proximal end and retained in place, e.g., by swaging, to hold the assembly together. In certain embodiments, a drag feature can also be incorporated, such as by including a drag ring, spring clip, etc., disposed within the receiver member and around the locking sphere to provide a drag force opposing polyaxial movement of the receiver member relative to the screw shank.

Figure 20:
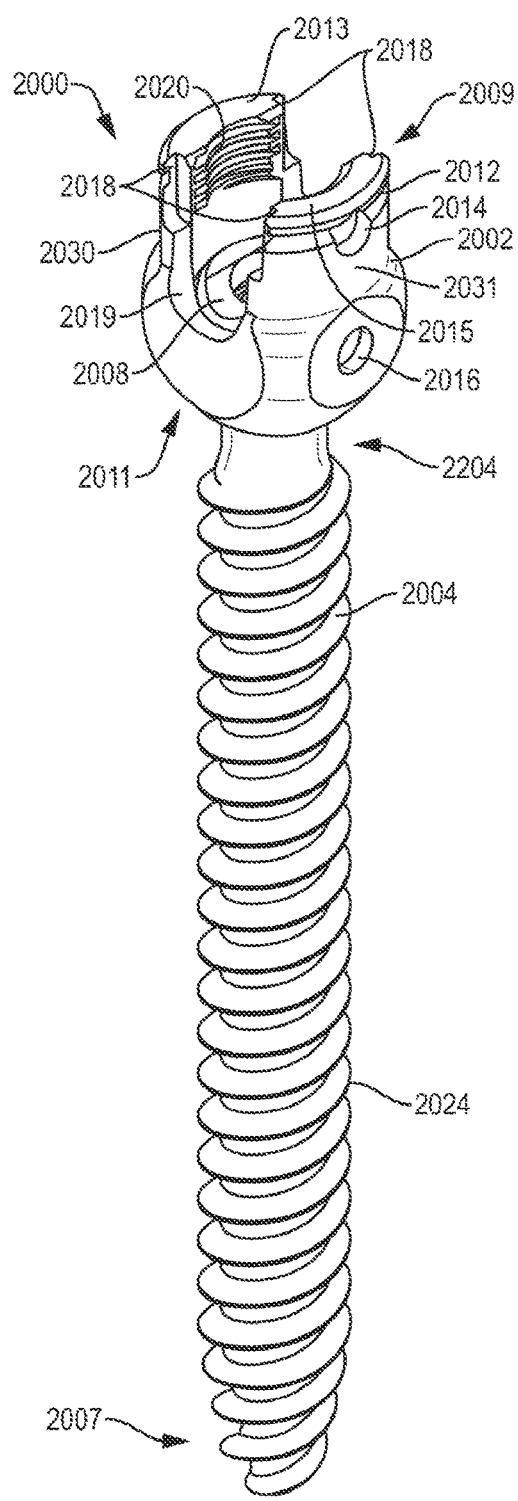
FIG. 20 is a perspective view of a bone anchor assembly, according to one embodiment.
Figure 21:
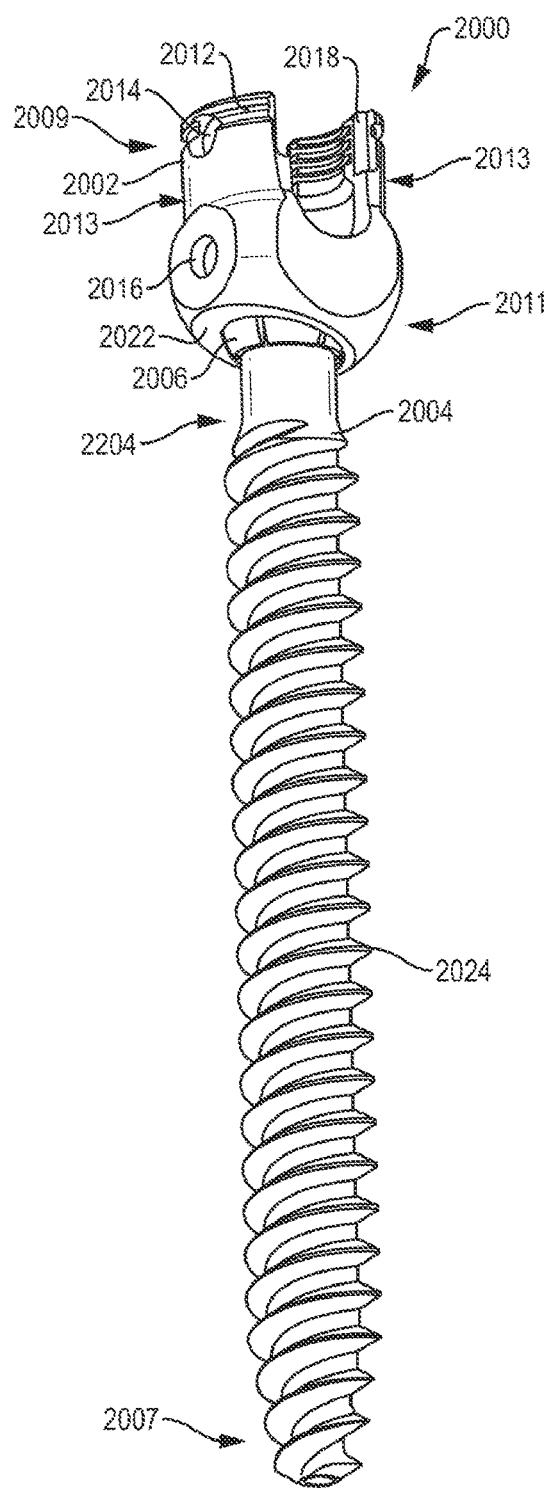
FIG. 21 is another perspective view of the bone anchor assembly of FIG. 20.
Figure 22:
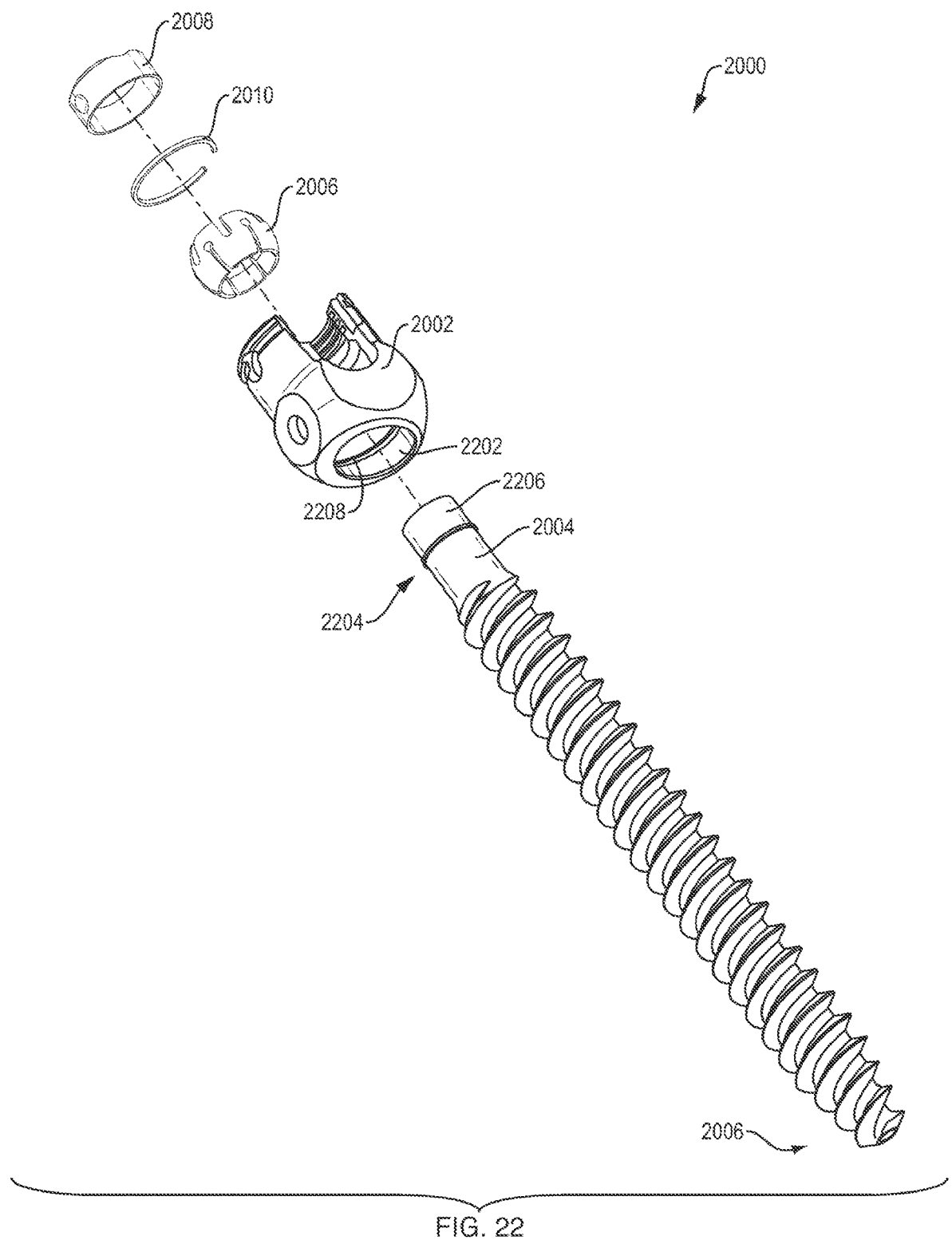
FIG. 22 is an exploded view of the bone anchor assembly of FIG. 20.
Figure 26:
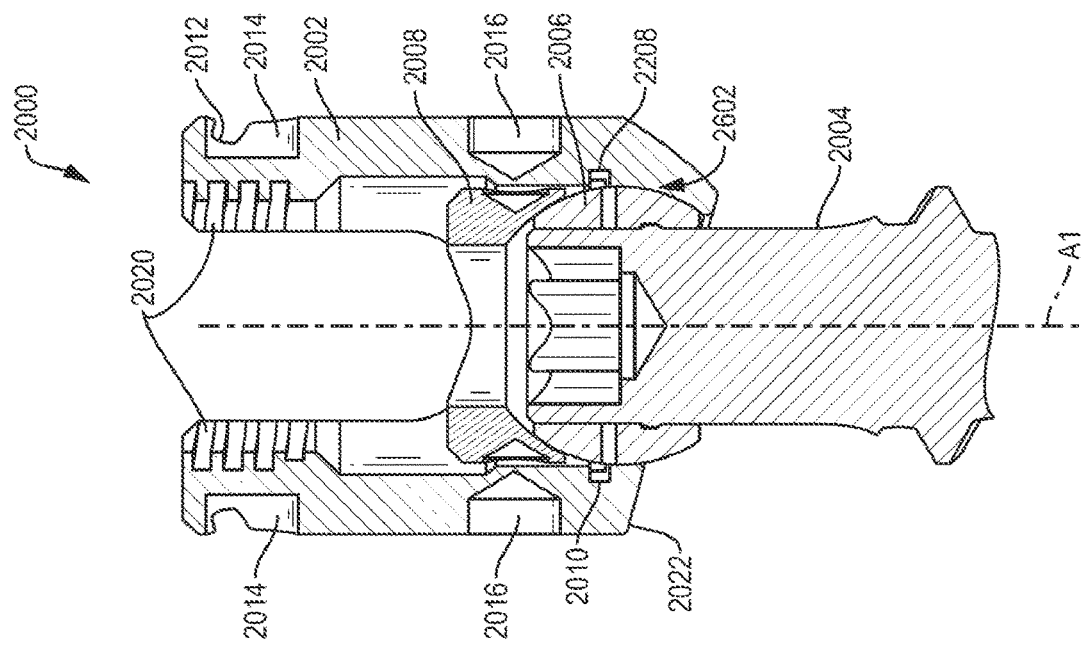
FIG. 26 is a front cross-sectional view of the proximal portion of the bone anchor assembly of FIG. 20.
Figure 25:
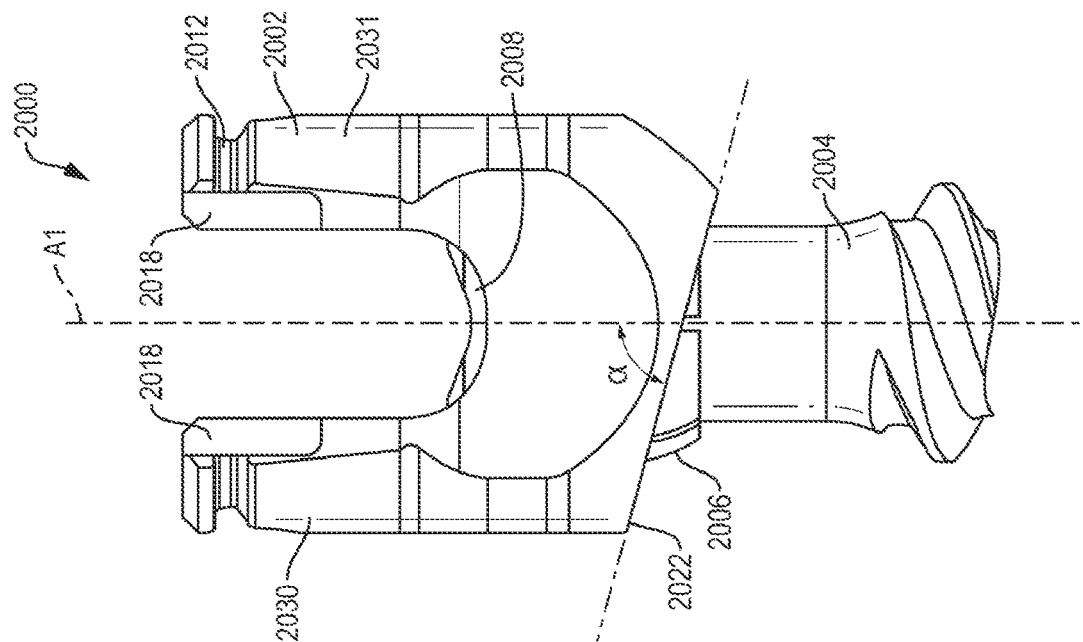
FIG. 25 is a front view of the proximal portion of the bone anchor assembly of FIG. 20.
Figure 27:
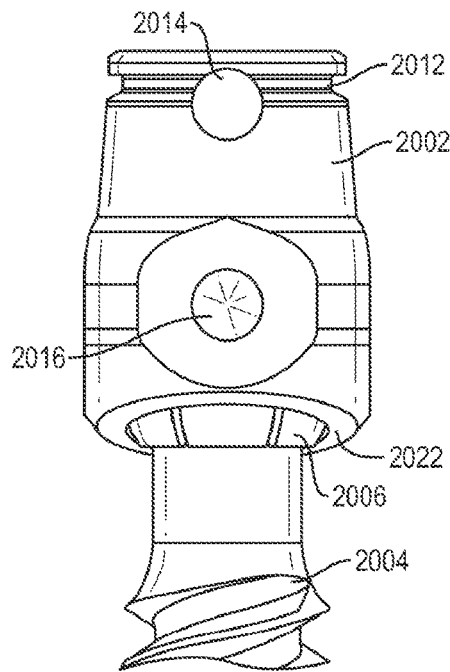
FIG. 27 is a side view of the proximal portion of the bone anchor assembly of FIG. 20.
Figure 28:
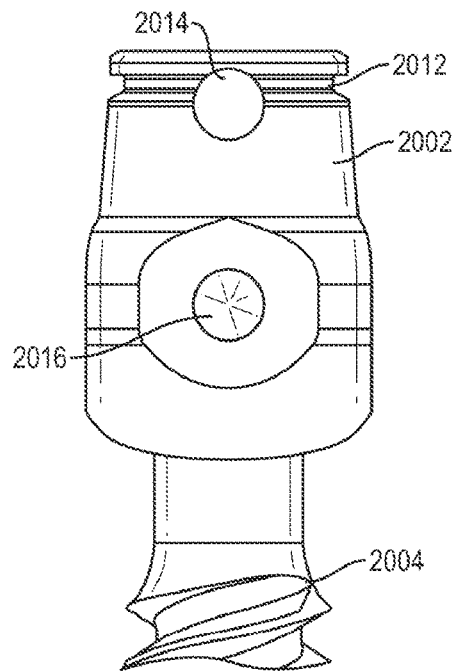
FIG. 28 is an opposing side view of FIG. 27.
Figure 29:
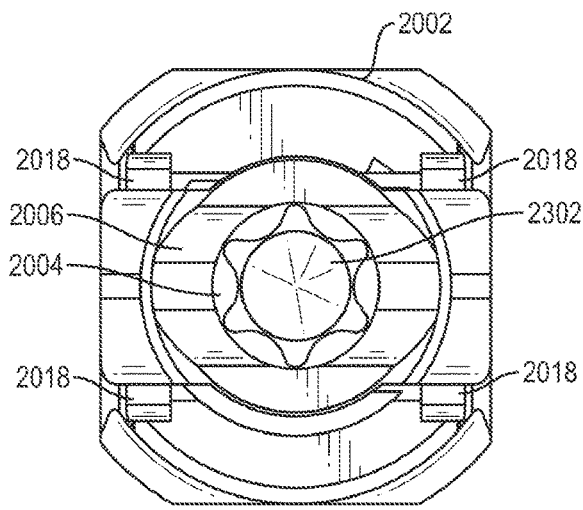
FIG. 29 is a top view of the bone anchor assembly of FIG. 20.
Figure 30:
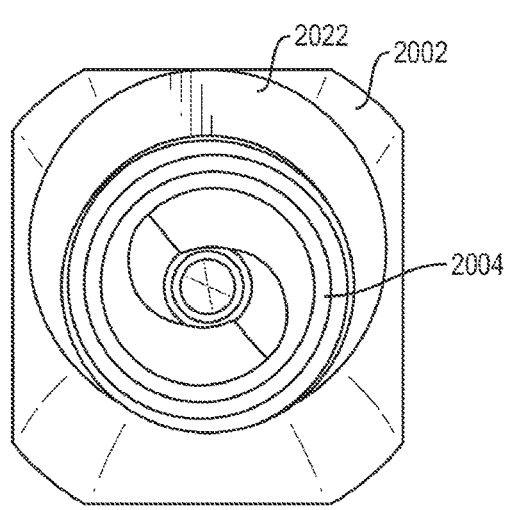
FIG. 30 is a bottom view of the bone anchor assembly of FIG. 20.
Figure 31:
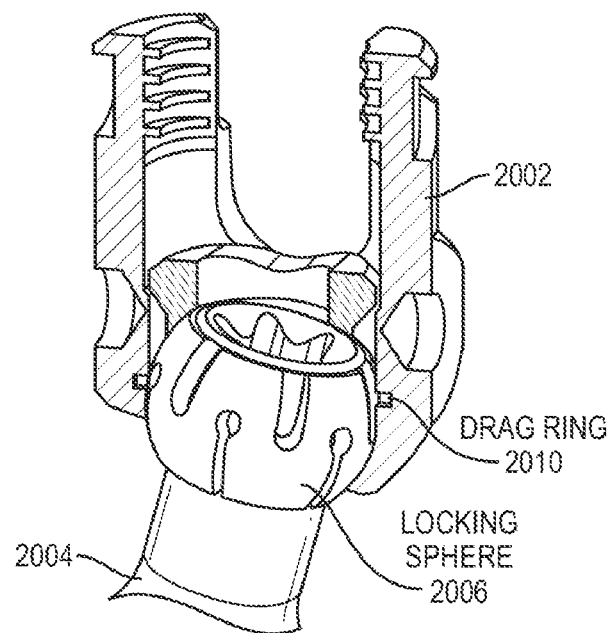
FIG. 31 is a perspective partial cross-sectional view bisecting the receiver member of the bone anchor assembly of FIG. 20.
Figure 32:
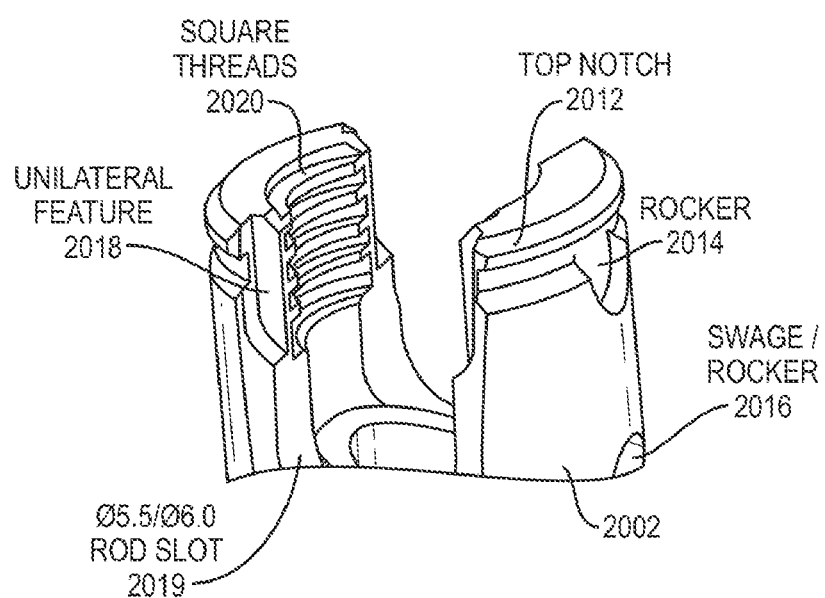
FIG. 32 is an enlarged perspective view of the proximal portion of the receiver member of the bone anchor assembly of FIG. 20.
Figure 35:
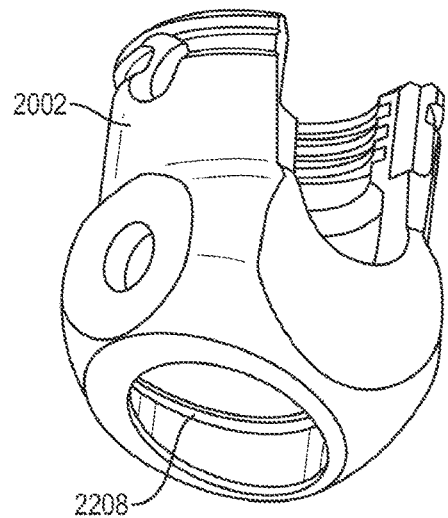
FIG. 35 is a perspective view of a receiver member of the bone anchor assembly of FIG. 20.
Figure 39:
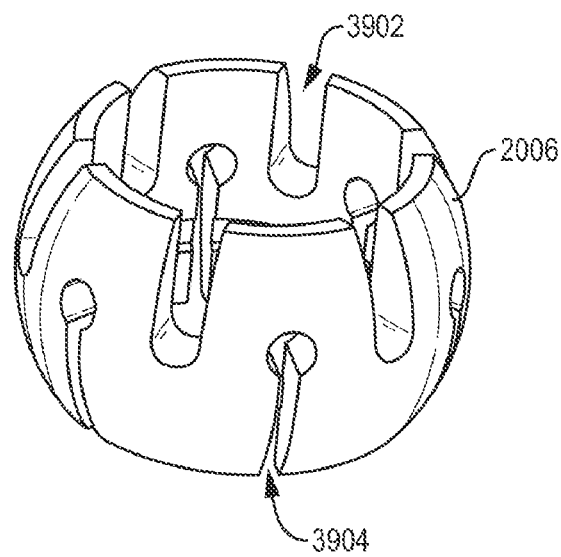
FIG. 39 is a perspective view of a locking sphere of the bone anchor assembly of FIG. 20.
Figure 40:
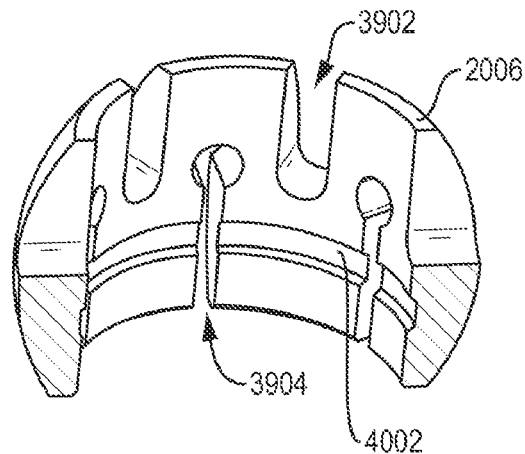
FIG. 40 is a perspective cross-sectional view of the locking sphere of FIG. 39.
Figure 41:
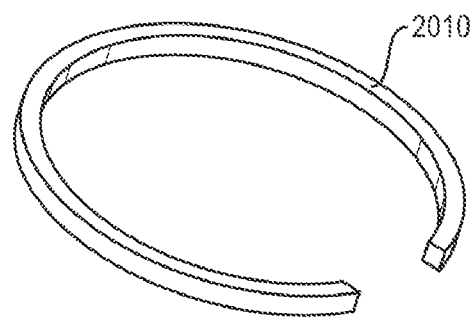
FIG. 41 is a perspective view of a drag ring of the bone anchor assembly of FIG. 20.

FIGS. 20-34 illustrate different views of one embodiment of a large diameter favored angle bone anchor assembly 2000 according to the present disclosure, and FIGS. 35-45 illustrate detail views of components of the assembly. More particularly, FIGS. 20 and 21 provide opposing perspective views of a bone anchor assembly 2000. FIG. 22 provides an exploded view of the bone anchor assembly 2000. FIG. 23 provides a cross-sectional view of the bone anchor assembly 2000. FIG. 24 provides a partially transparent perspective view of the proximal portion of the bone anchor assembly 2000. FIG. 25 provides a front view of the proximal portion of the bone anchor assembly 2000. FIG. 26 provides a front cross-sectional view of the proximal portion of the bone anchor assembly 2000. FIGS. 27 and 28 provide opposing side views of the proximal portion of the bone anchor assembly 2000. FIGS. 29 and 30 provide top and bottom views of the bone anchor assembly 2000. FIGS. 31-34 illustrate various features of the receiver member 2002 of the bone anchor assembly 2000. FIGS. 35-38 provide perspective, front, top, and bottom views of the receiver member 2002. FIGS. 39 and 40 provide perspective and cross-sectional views of the locking sphere 2006 of the bone anchor assembly 2000. FIG. 41 provides a perspective view of a drag ring 2010 of the bone anchor assembly 2000. Finally, FIGS. 42-45 provide perspective, front, and cross-sectional views of a compression member 2008 of the bone anchor assembly 2000.

As shown in FIGS. 20-34, one embodiment of a large diameter favored angle bone anchor assembly 2000 can include a receiver member 2002 and a bone anchor or shank 2004 having a proximal head portion 2204 and a distal bone-engaging portion 2007. The receiver member 2002 can have a proximal end 2009 defined by a pair of spaced apart arms 2013, 2015 forming a U-shaped recess 2019 (also referred to as a rod-receiving recess or slot) therebetween to receive a spinal fixation element (not shown), such as a spinal rod. A polyaxial seat 2602 (see FIG. 26) can be formed in a distal end 2011 of the receiver member 2002 for polyaxially seating a locking sphere 2006 coupled to the proximal portion 2204 of the bone anchor/shank 2004. The bone anchor assembly 2000 can further include a compression member or cap 2008 and a drag ring 2010 disposed within the receiver member 2002, each of which can contact the locking sphere 2006 to exert friction forces thereon that can selectively resist and/or prevent any relative movement of the receiver member 2002 relative to the bone anchor/shank 2004.

The bone anchor assembly 2000 can be similar in many respects to the bone anchor assemblies described above, and can include any of the various features described above in any combination. For example, the receiver member 2002 can include any of a variety of features to facilitate engagement of a surgical instrument with the bone anchor assembly. These can include a groove or channel 2012 formed in an outer surface at the proximal end of each spaced apart arm 2013, 2015 of the receiver member 2002 that can define a "top-notch" feature that can be engaged with a corresponding portion of an instrument, such as a projection, to facilitate coupling of the instrument to the receiver member.

In other embodiments, the receiver member 2002 can include a proximal rocker feature (or first recess) 2014 formed in a proximal portion 2009 of the receiver member 2002 that can be used to facilitate reducing a rod distally into the U-shaped recess 2019 of the receiver member 2002. The proximal rocker reducer feature 2014 can allow a rocker instrument to pivotably couple to the receiver member 2002 for reduction of a spinal fixation element into the receiver member 2002 using a levering or rocking motion. The proximal rocker feature 2014 can be a bilateral circular detail or recess that intersects the top-notch feature/groove 2012, as described above. In other embodiments, however, different shapes can be utilized for the proximal rocker feature recess.

In some embodiments, the receiver member 2002 can additionally or alternatively include a distal rocker feature (also referred to as a second recess) 2016. The distal rocker feature 2016 can be formed in the receiver member 2002 at a position distal to the proximal rocker feature 2014. The second or distal rocker feature 2016 can provide an alternative coupling position for a rocker instrument, such as a reducer rocker fork, to the proximal rocker feature 2014. The second rocker feature can also be a swage feature used to retain a compression member 2008 within the receiver member 2002. During assembly, for example, a swaging process can form the second rocker feature 2016 and displace receiver member material into a recess 4202 (see FIG. 42) formed in the compression member 2008 to constrain it within the receiver member 2002 and prevent, e.g., its removal out the proximal end 2009 of the receiver member 2002. The second rocker feature 2016 can be formed on opposing sides of the receiver member and material in each arm 2013, 2015 of the receiver member 2002 can be displaced by swaging into the recesses formed on opposing sides of the compression cap 2008.

The receiver member 2002 can include at least one unilateral attachment feature 2018 that can enable a surgical instrument to couple to or engage with the receiver member 2002 in a manner that leaves the rod-receiving slot 2019 unobstructed, e.g., by allowing attachment of an instrument to the receiver member 2002 by engaging only one arm 2013 or 2015 of the receiver member 2002. In one embodiment, the receiver member 2002 can include a unilateral attachment feature 2018 on four proximal quadrants of the receiver member 2002. For example, a unilateral attachment feature 2018 can be formed on opposing laterally-facing edges of each of the spaced apart arms 2013, 2015. A surgical instrument can attach to two adjacent unilateral features 2018 on one side of the receiver member 2002, leaving the rod-receiving slot 2019 open to receive a spinal fixation rod and/or set screw introduced distally from the proximal end 2009 of the receiver member 2002, as explained above.

As described above, the receiver member 2002 can receive spinal fixation elements of multiple sizes. For example, spinal rods having a diameter of about 5.5 mm or a diameter of about 6.0 mm can be received within the rod-receiving recess 2019. A proximal portion of the spaced apart arms 2013, 2015 of the receiver member 2002 can include a threaded inner surface 2020 that can engage with a set screw or other locking element received therebetween to lock a spinal rod within the receiver member 2002. In some embodiments, the inner threaded portion 2020 can have square threads e.g., to engage with counterpart external square threads of a set screw (e.g., see FIG. 14).

Figure 36:
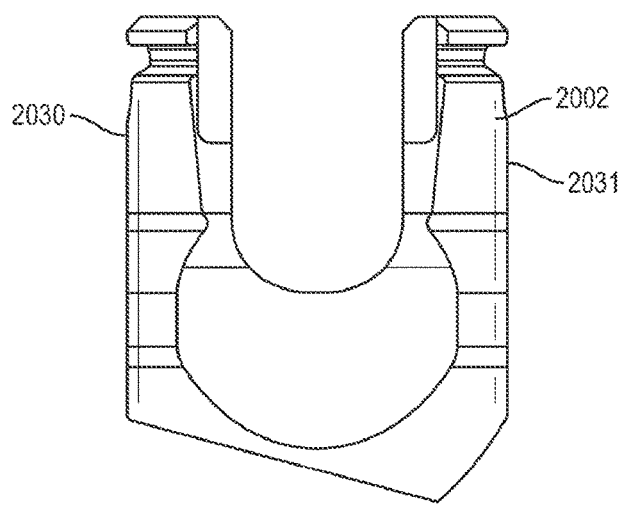
FIG. 36 is a front view of the receiver member of FIG. 35.
Figure 37:
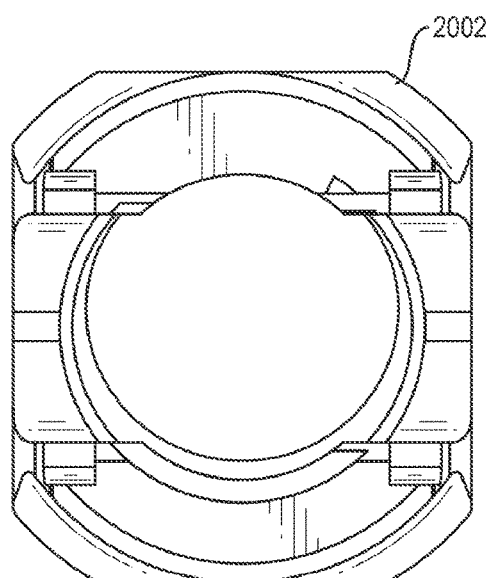
FIG. 37 is a top view of the receiver member of FIG. 35.
Figure 38:
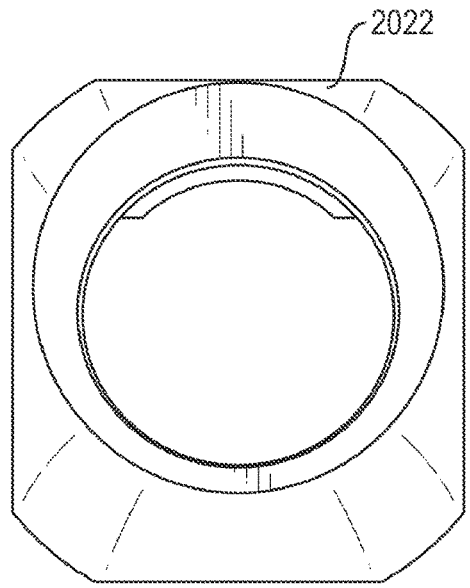
FIG. 38 is a bottom view of the receiver member of FIG. 35.

The receiver member 2002 can also include a taper in at least one direction. FIG. 33 is a partially transparent view of the bone anchor assembly 2000 of FIG. 20 that shows, among other things, a taper 3302 of the outer surface of the receiver member 2002 in a first direction. More particularly, a first pair of opposed sides 3304, 3306, shown in FIG. 33 as exterior walls of the spaced-apart arms 2013, 2015, can have a first taper with respect to a first plane that contains a proximal-distal axis A1 of the receiver member (i.e., the plane of the page of FIG. 33). As shown above in FIG. 7, a second taper can be included in an orientation that is 90 degrees offset from the orientation shown in FIG. 33, i.e., a second taper with respect to a second plane that contains the proximal-distal axis A1 of the receiver member and is offset from the first plane. This second taper is not required, however, and, as shown in FIGS. 20, 25, and 36, among others, the bone anchor assembly 2000 does not include a second taper. Instead, the surfaces 2030, 2031 adjacent planar tapered surfaces 3304, 3306, have a straight cylindrical profile. In embodiments where multiple tapers are included, the first plane and the second plane can be perpendicular to one another in some embodiments, though other offset angles are also possible. Accordingly, in some embodiments, when implanted into a patient's spine, the receiver member 2002 can have walls that taper in both the cephalad-caudal direction and the medial-lateral direction, for example. Taper of the receiver member 2002 with respect to one or two offset planes can aid in instrument attachment to the receiver member as the angled characteristic of the receiver member, i.e., the tapering of exterior walls or an outer surface of the receiver member in one or two directions, can guide surgical instruments to self-center during attachment to the receiver member.

In addition to the above-described features of the receiver member 2002, the receiver member can be configured to provide a greater degree of angulation in a first direction relative to a second direction that is opposite the first direction. For example, the receiver member 2002 can include a distal facing surface 2022 that is obliquely angled relative to a central proximal-distal axis A1 of the receiver member. This can effectively angle a hole 2202 (see FIG. 22) formed in the distal facing surface of the receiver member 2002 to one side, thereby allowing a greater degree of angulation of the bone anchor 2004 toward that side in comparison to an opposite side. This can bias the bone anchor assembly 2000 to favor angulation in one direction. FIG. 25 illustrates the angle α created between the central proximal-distal axis A1 and the plane of the distal facing surface 2022.

The bone anchor or shank 2004 can similarly include any of the various features described above. For example, the bone anchor 2004 can include external threads 2024 extending along the bone-engaging portion 2007 of the shank 2004. Various thread forms can be utilized for shanks of the present disclosure, including solid dual lead, solid cortical fix, cannulated dual lead, cannulated cortical fix, and cannulated cortical fix fenestrated threads. The bone shank 2004 can have a quick-start tip 3402, as shown in FIG. 34, with threads that extend distally to a distal tip 3410 of the bone engaging portion 2007. In this manner, the threads 2024 can extend to the contact surface between the bone shank 2004 and the bone, which can provide immediate purchase of the thread 2024 into bone.

In addition, a recess 3404, also shown in FIG. 34, can be centered and formed in the distal tip of the bone shank 2004. This recess 3404, which can be referred to as a centering recess, can be used to support the distal bone-engaging portion 2007 of the shank 2004 in a centered manner during the manufacturing process. In some embodiments, the centering recess 3404 can be a blind bore that extends proximally from the distal tip of the bone-engaging portion (e.g., as shown in the partially transparent view of FIG. 34). In other embodiments, the centering recess 3404 can be a full cannulated recess that extends from the proximal end to the distal end of the bone shank 2004. Such a recess can allow, for example, for introduction of the shank 2004 over a guidewire, delivery of cement or other flowable material through the shank 2004 into bone, etc. A drive feature 2302 (see FIGS. 23 and 29) can be formed in the proximal head 2204 of the bone shank 2004 to allow a driver to control rotation of the anchor during implantation, etc. Any of a variety of drive feature designs can be utilized, including square drive, hex drive, lobed drives, etc. The illustrated embodiment includes a T27 drive feature.

The bone anchor assembly 2000 can be configured for use with larger diameter bone anchors or shanks 2004. For example, in some embodiments the bone anchor assembly 100 described above can have a bone anchor 104 with a shank diameter of up to about 7 mm. Above about that size, the bone anchor can become too large for bottom loading through the hole formed in the distal surface of the receiver member, especially when the bone anchor includes a spherically-shaped proximal end. The bone anchor assembly 2000 can provide for larger size bone anchors by utilizing a bone anchor with a relatively uniform diameter or column-shaped proximal end that can be bottom loaded into the receiver member 2002 through the hole 2202 and coupled to a locking sphere 2006 that is top loaded into the receiver member. This modular configuration can allow, in some embodiments, the use of bone anchors with a diameter between about 7 mm and about 12 mm, though this configuration could also be used for any smaller diameter in place of a single-component bone anchor like that shown in the embodiment of FIG. 1.

As shown in FIG. 22, the bone anchor 2004 can include a proximal portion 2204 configured to couple with the locking sphere 2006. The proximal portion 2204 can include a rib, protrusion, or other feature 2206 formed on an outer surface thereof that can interface with a recess or other complementary feature 4002 (see FIG. 40) formed on an inner surface of the locking sphere 2006. This arrangement can secure the locking sphere 2006 relative to the bone anchor 2004 such that the bone anchor 2004 can move polyaxially relative to the receiver member 2002 when the locking sphere 2006 is disposed in the polyaxial seat 2019 of the receiver member 2002. Further, movement of the bone anchor 2004 relative to the receiver member 2002 can be controlled using friction forces exerted on the locking sphere 2006, as explained in more detail below.

As shown in FIGS. 39 and 40, the locking sphere 2006 can have a spherical outer surface and a columnar inner surface configured to receive the proximal end portion 2204 of the bone anchor 2004. The locking sphere 2006 can also include one or more relief slits 3902 formed therein to allow for deformation of the locking sphere 2006 when coupling with the bone anchor 2004. In the illustrated embodiment, two different shapes of relief slits 3902, 3904 are provided in an alternating pattern around the circumference of the locking sphere 2006. The inner surface of the locking sphere 2006 can include the recess 4002 that can receive the rib 2206 formed on the outer surface of the proximal portion 2204 of the bone anchor 2004 to help secure the two components relative to one another when coupled.

As shown in FIGS. 22-24, 26, and 41, the bone anchor assembly 2000 can include a drag ring 2010 disposed within a recess or groove 2208 (see FIGS. 22, 26, and 35) formed in a distal portion 2011 of the receiver member 2002. The drag ring 2010 can create a friction fit between an interior surface of the drag ring 2010 and an exterior surface of the locking sphere 2006, such that the receiver member 2002 of the bone anchor assembly can provisionally maintain a position relative to the bone shank 2004 prior to a full locking of the bone anchor assembly, e.g., with a set screw or other locking element. The drag ring 2010 can be positioned above an equator or widest diameter of the locking sphere 2006. This can mean, in some embodiments, that the drag ring 2010 can be disposed within the distal portion 2011 of the receiver member 2002 after the locking sphere 2006 is top loaded into the distal portion of the receiver member.

Figure 42:
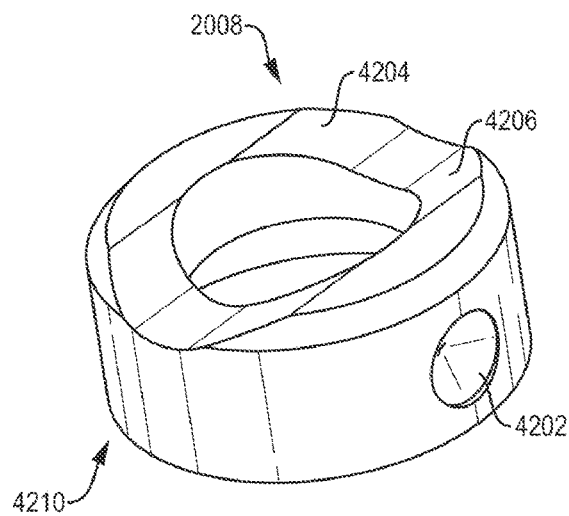
FIG. 42 is a perspective view of a compression member of the bone anchor assembly of FIG. 20.
Figure 43:
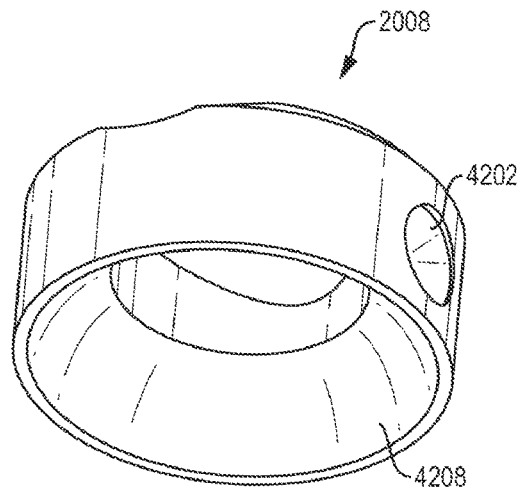
FIG. 43 is another perspective view of the compression member of FIG. 42.
Figure 44:
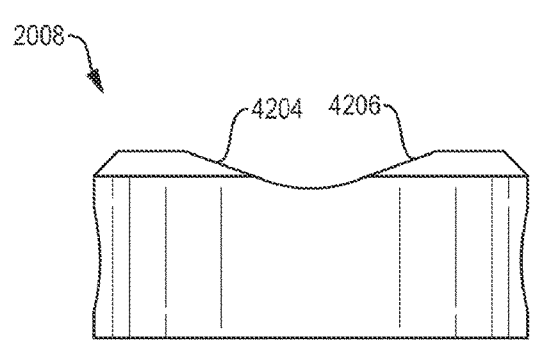
FIG. 44 is a front view of the compression member of FIG. 42.
Figure 45:
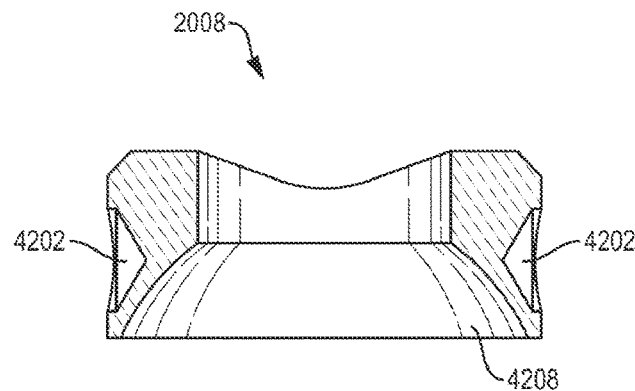
FIG. 45 is a front cross-sectional view of the compression member of FIG. 42.

FIGS. 42-45 illustrate one embodiment of a compression member or cap 2008 of the present disclosure. FIGS. 42 and 43 are perspective views of one embodiment of a compression member 2008, FIG. 44 is a front view of the compression member 2008, and FIG. 45 is a cross-sectional view of the compression member 2008. As noted above, the outer surface of the compression cap 2008 can include depressions or recesses 4202 that can receive material from the receiver member 2002 that is displaced during a swage that can form the second rocker feature. A proximal portion of the compression member 2008 can form a seat 4210 for receiving a spinal rod. More particularly, two planar surfaces 4204, 4206 of the compression member can be angularly offset from one another to form a substantially "V" shaped groove that can seat a spinal rod of varying diameters. A bottom surface 4208 of the compression member 2008 can include a substantially spherical surface configured to contact the locking sphere 2006 and exert a friction force thereon when the compression member 2008 is advanced distally relative to the receiver member 2002 (e.g., by a user tightening a set screw into the threads formed in the proximal portion of the receiver member).

Figure 46:
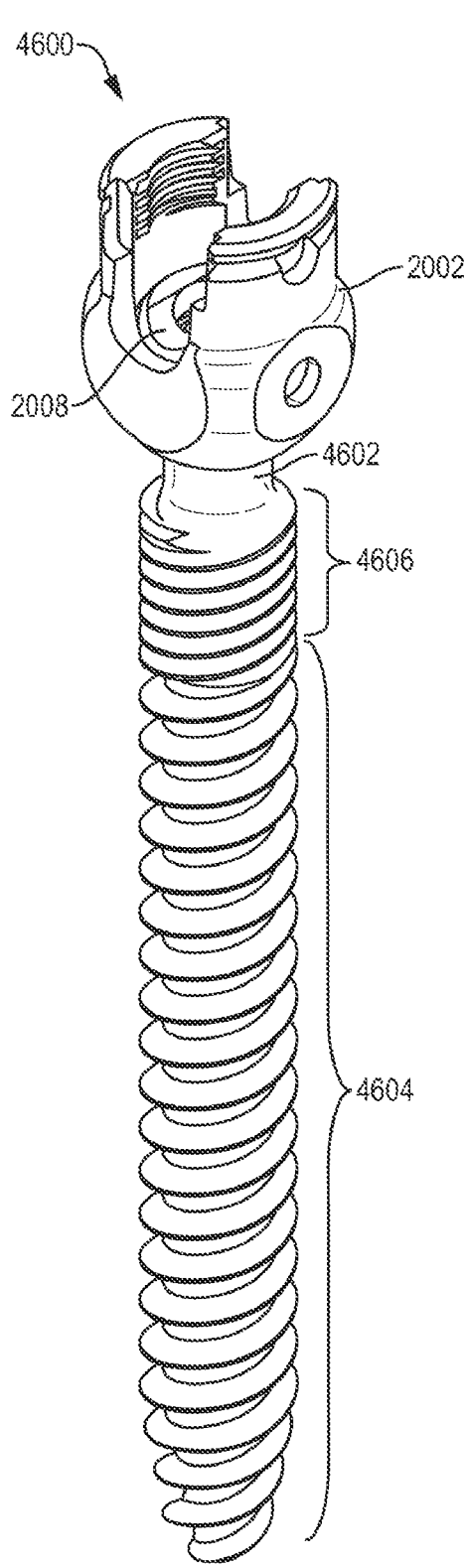
FIG. 46 is a perspective view of a bone anchor assembly, according to one embodiment.
Figure 47:
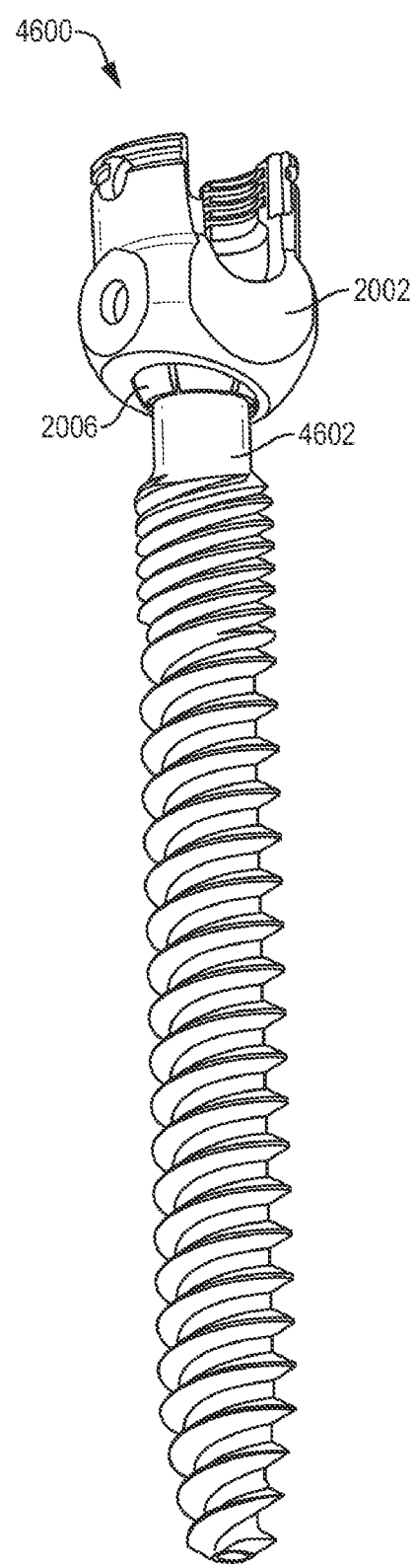
FIG. 47 is another perspective view of the bone anchor assembly of FIG. 46.
Figures 48, 49:
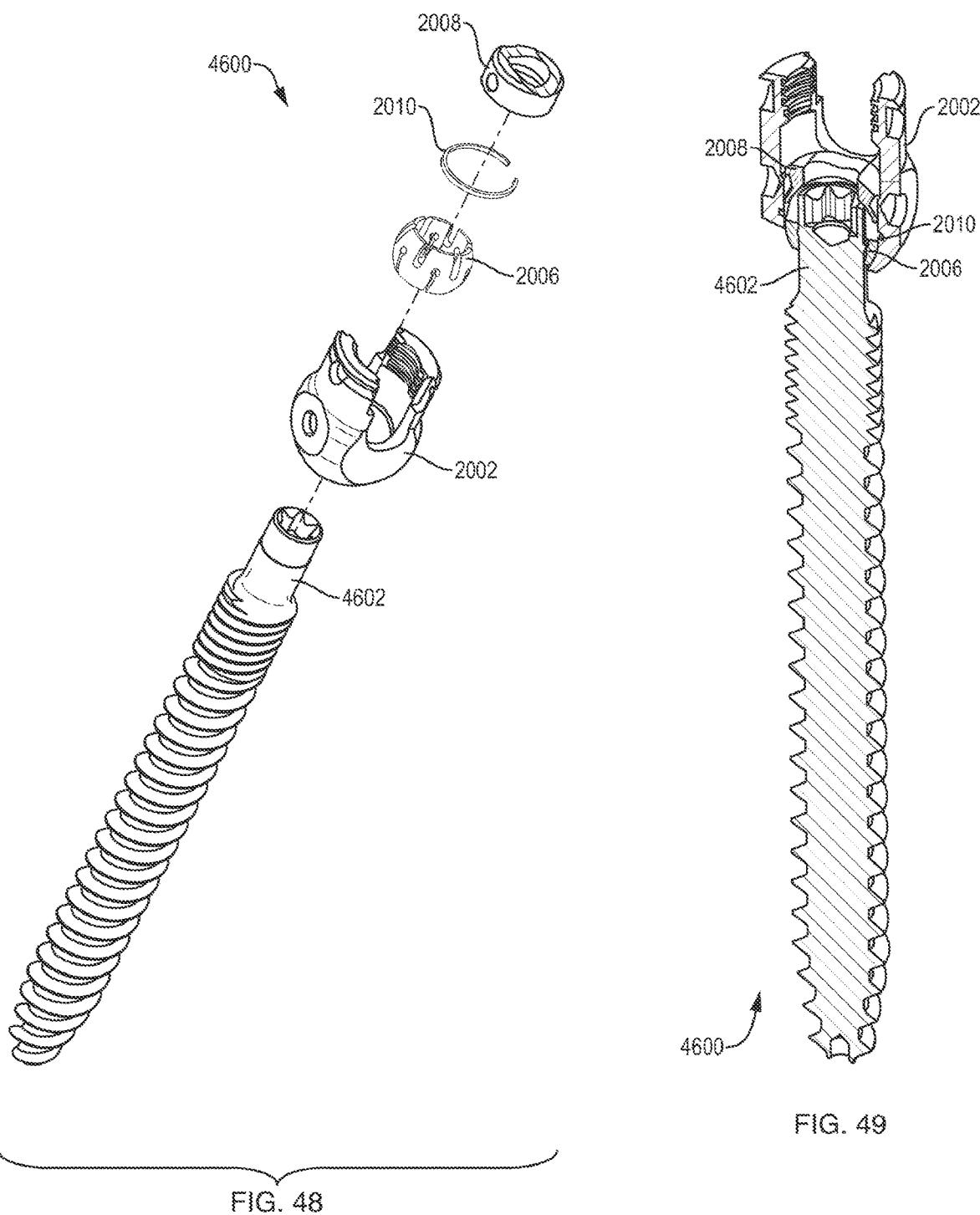
FIG. 48 is an exploded view of the bone anchor assembly of FIG. 46.
FIG. 49 is a perspective longitudinal cross-sectional view of the bone anchor assembly of FIG. 46.

FIGS. 46-49 illustrate different views of another embodiment of a large diameter favored angle bone anchor assembly 4600 according to the present disclosure. More particularly, FIGS. 46 and 47 provide opposing perspective views of a bone anchor assembly 4600. FIG. 48 provides an exploded view of the bone anchor assembly 4600. FIG. 49 provides a cross-sectional view of the bone anchor assembly 4600.

In the embodiment of FIGS. 46-49, the receiver head 2002, locking sphere 2006, compression member 2008, and drag ring 2010 can be the same as those described above in connection with the embodiment of FIG. 20, but a differently-configured bone anchor or shank 4602 can be provided. The bone anchor 4602 can include a plurality of threaded sections that can be configured to increase fixation of the bone anchor assembly 4600 in bone. For example, the bone anchor 4602 can include a first distal threaded section 4604 that has a first pitch and a first number of thread starts and a second proximal threaded section 4606 that has a second pitch less than the first pitch and a second number of thread starts greater than the first number of thread starts. The different threaded sections or portions 4604, 4606 can have a constant lead (equal to thread starts multiplied by thread pitch), i.e., can translate the bone anchor 4602 an equal distance in a direction parallel to a longitudinal axis of the bone anchor shaft when rotated one turn (360°).

For a bone anchor assembly designed to be implanted through the pedicle of a vertebra, for example, the threaded distal section 4604 can be configured to engage cancellous bone in the anterior vertebral body of the vertebra and the threaded proximal section 4606 can be configured to engage cortical bone of the pedicle of the vertebra. Use of threaded sections with a constant lead can facilitate insertion of the anchor 4602 into the vertebra and prevent stripping of the pedicle wall. Additional details regarding the bone anchor 4602 and its plurality of threaded sections can be found in U.S. Pat. No. 9,155,580, entitled "Multi-threaded Cannulated Bone Anchors," the entire contents of which are incorporated by reference herein.

Figure 50:
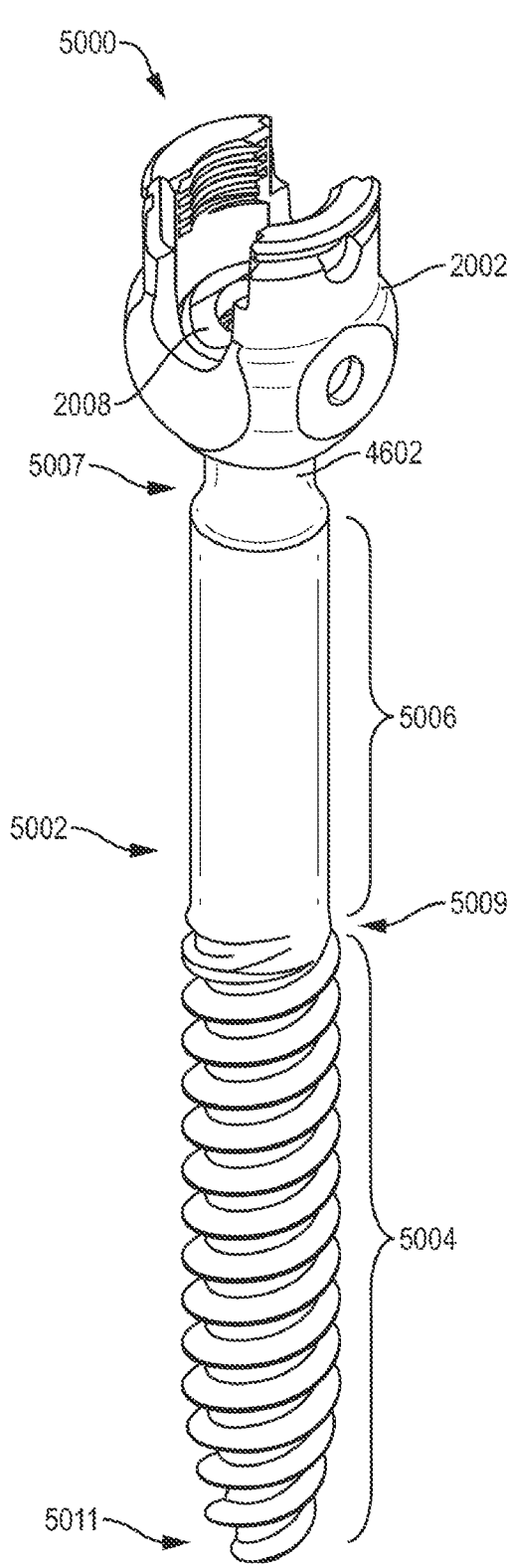
FIG. 50 is a perspective view of a bone anchor assembly, according to one embodiment.
Figure 51:
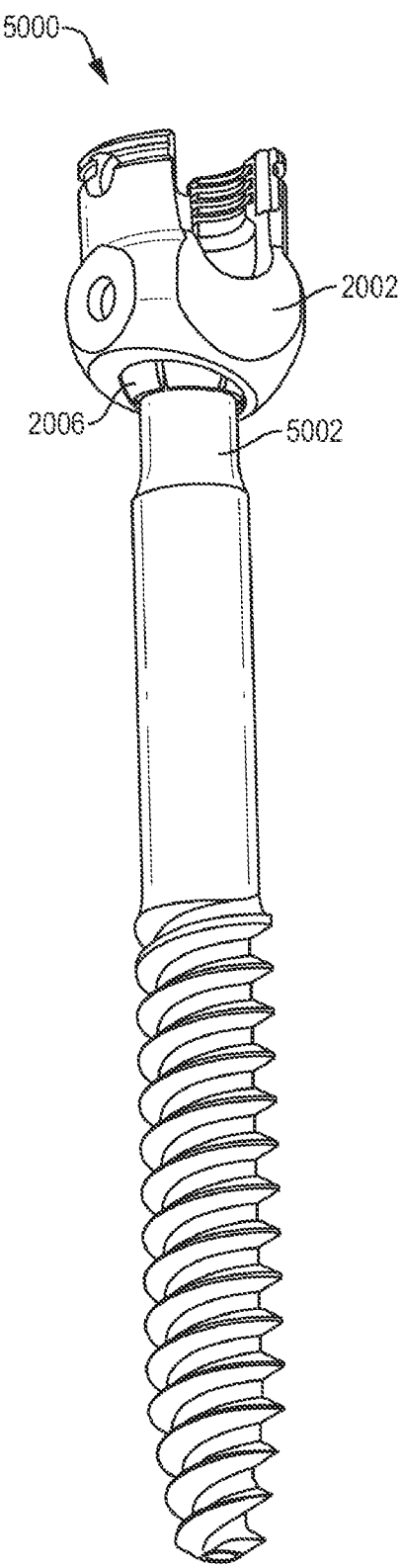
FIG. 51 is another perspective view of the bone anchor assembly of FIG. 50.
Figures 52, 53:
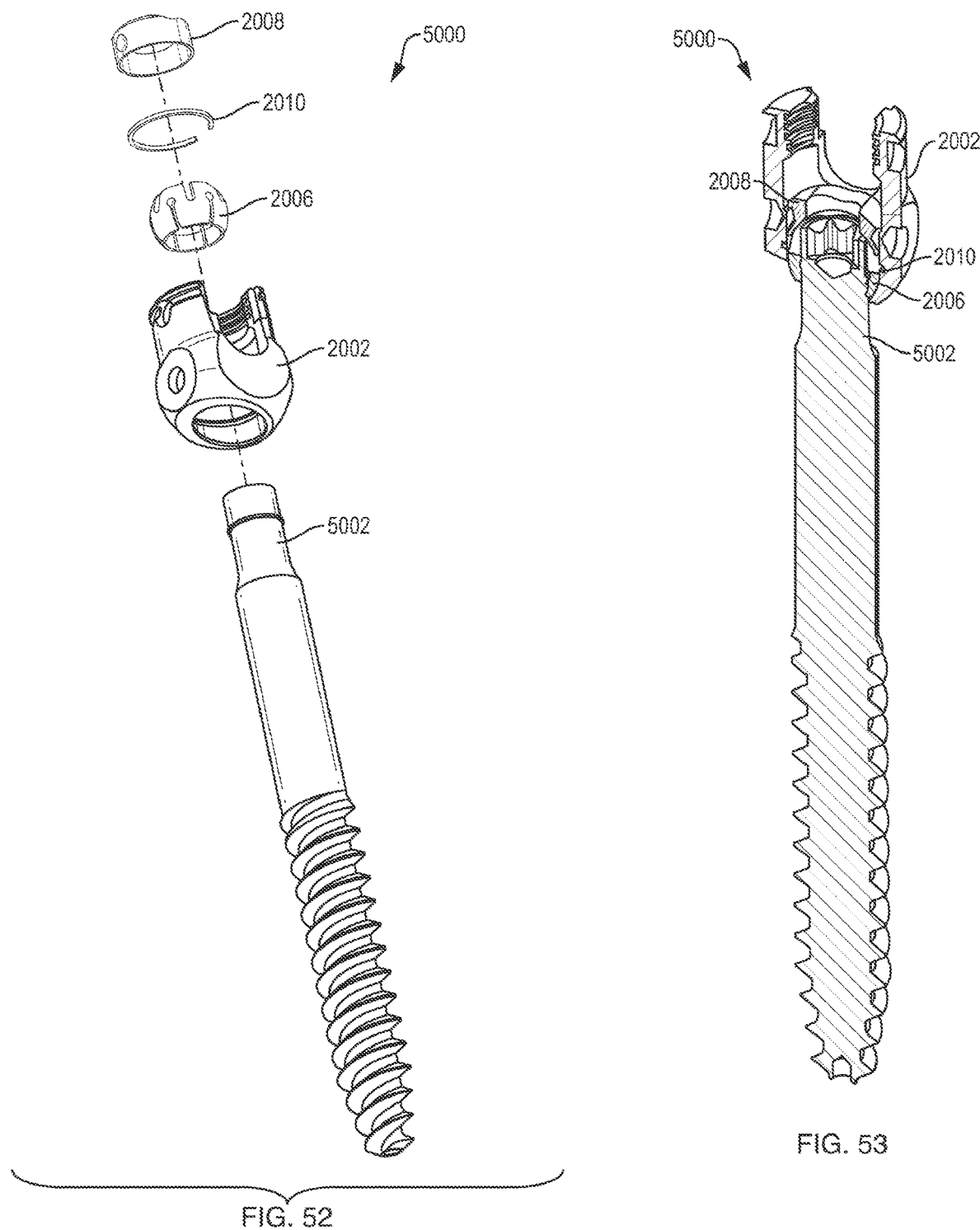
FIG. 52 is an exploded view of the bone anchor assembly of FIG. 50.
FIG. 53 is a perspective longitudinal cross-sectional view of the bone anchor assembly of FIG. 50.
Figure 54:
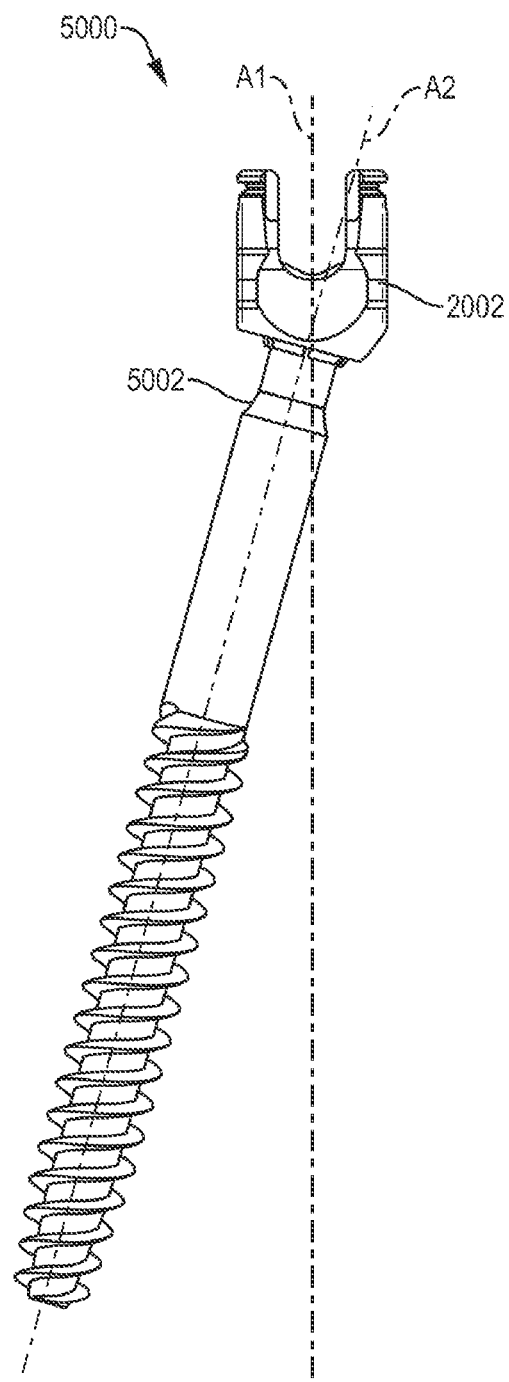
FIG. 54 is a front view of the bone anchor assembly of FIG. 50 in an angulated state.

FIGS. 50-54 illustrate different views of yet another embodiment of a large diameter favored angle bone anchor assembly 5000 according to the present disclosure. More particularly, FIGS. 50 and 51 provide opposing perspective views of a bone anchor assembly 5000. FIG. 52 provides an exploded view of the bone anchor assembly 5000. FIG. 53 provides a cross-sectional view of the bone anchor assembly 4600. FIG. 54 provides a front view of the bone anchor assembly 5000 in an angulated state.

In the embodiment of FIGS. 50-54, the receiver head 2002, locking sphere 2006, compression member 2008, and drag ring 2010 can be the same as those described above in connection with the embodiments of FIGS. 20 and 46, but a differently-configured bone anchor or shank 5002 can be provided. The bone anchor 5002 can include a first, distal threaded portion or section 5004 and a second portion or section 5006 without threads that is disposed between the first portion 5004 and the proximal portion 5007 of the bone anchor 5002. The second portion 5006 can have a smooth outer surface with a diameter that is less than a maximum major diameter of the threaded portion 5004, i.e., less than the major diameter near the proximal end 5009 of the first portion 5004 before the diameter begins to taper closer to a distal end 5011 of the bone anchor 5002. In some embodiments, the diameter of the second portion 5006 can be close to the maximum major diameter of the threaded portion 5004 to maximize the strength of the bone anchor 5002. In some embodiments, the diameter of the second portion 5006 can be between a maximum minor diameter and a maximum major diameter of the threaded portion 5004.

The second portion 5006 can have a variety of lengths according to a desired overall length of the bone anchor 5002. In some embodiments, the length of the second portion 5006 can be at least about 30% of a length of the first portion 5004, and in some embodiments the length of the second portion can be between about 30% and about 90% of the length of the first portion 5004.

The bone anchor 5002 can be useful in certain applications where a longer screw with maximum strength is desirable. One such application is in "SAI" trajectories, i.e., procedures where the bone anchor is introduced through the sacral alar such that its distal end arrives in the ilium. In such procedures, it can be desirable to provide the extended second portion 5006 without threads and with a maximum strength to resist forces exerted thereon. Accordingly, the unthreaded second portion 5006 can be provided that has a diameter just under that of the maximum major diameter of the threaded first portion 5004.

FIG. 54 illustrates the bone anchor assembly 5000 in an angulated state, where a proximal-distal axis A1 of the receiver member 2002 is obliquely angled relative to a proximal-distal axis A2 of the bone anchor 5002. This is in contrast to the positioning shown in FIGS. 50-53 where the axes A1 and A2 are aligned and coaxial with one another. As noted above, the "favored angle" configuration of the receiver member 2002 can allow a greater degree of angulation in one direction versus a second opposite direction. For example, a greater degree of angulation in the direction shown in FIG. 54, where a distal portion of axis A2 is disposed to the left of axis A1 in the plane of the figure, is possible in comparison to an opposite direction of angulation, where a distal portion of axis A2 would be disposed to the right of the axis A1 in the plane of the figure.

Figures 55, 56:
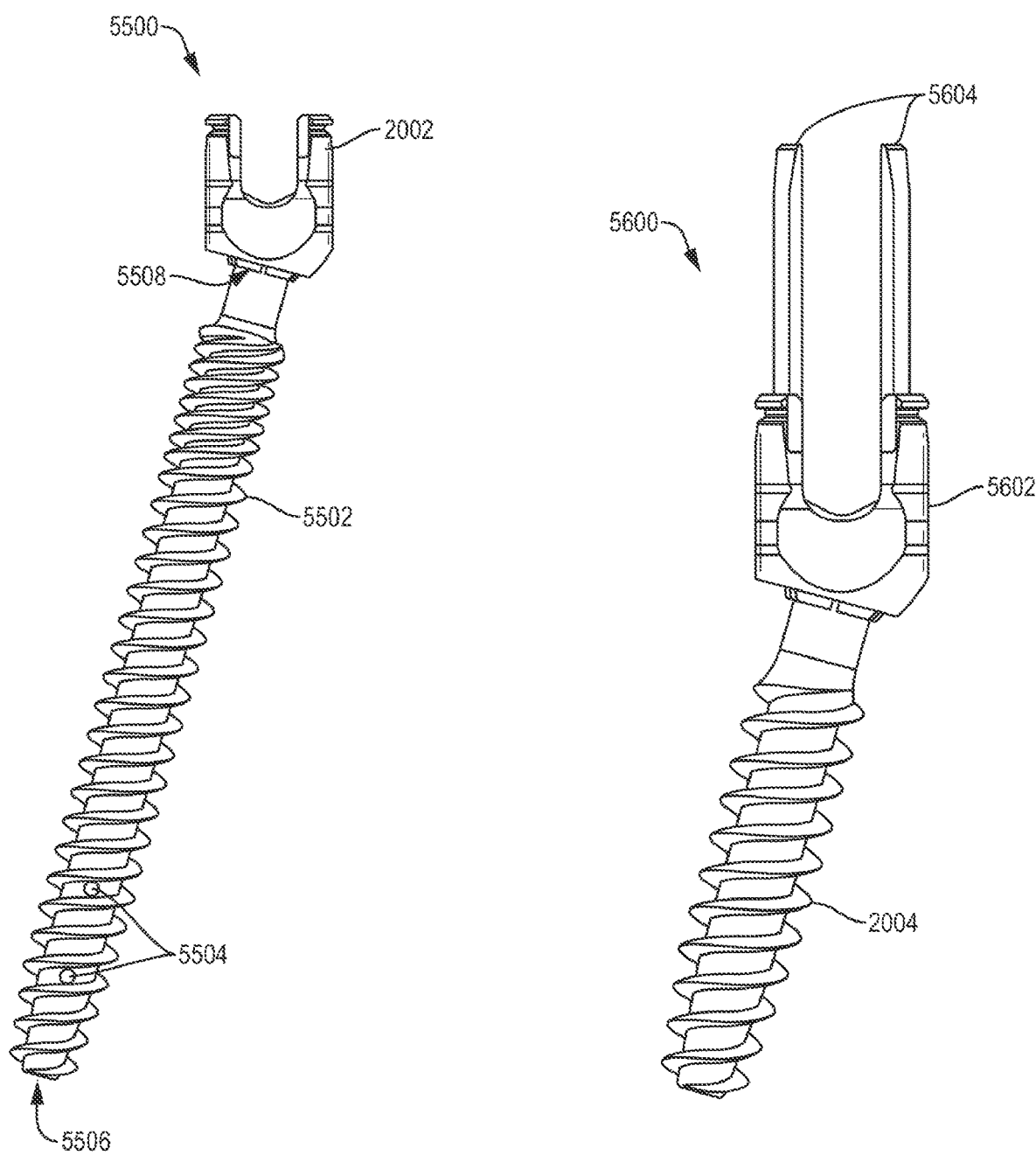
FIG. 55 is a front view of a bone anchor assembly, according to one embodiment.
FIG. 56 is a front view of a bone anchor assembly, according to one embodiment.

FIG. 55 illustrates still another embodiment of a large diameter favored angle bone anchor assembly 5500 according to the present disclosure. In this embodiment, the receiver member 2002, locking sphere 2006, compression member 2008, and drag ring 2010 can be the same as those described above in connection with the embodiments of FIGS. 20, 46, and 50, but a differently-configured bone anchor or shank 5502 can be provided. In particular, the bone anchor assembly 5500 can include a fenestrated bone anchor 5502. That is, the bone anchor 5502 can include a cannula or passage extending along its longitudinal axis from a proximal end toward a distal end thereof. In addition, the bone anchor 5502 can include one or more outlets 5504 formed along a length thereof that can intersect with the cannula or passage formed in the bone anchor. The one or more outlets 5504 can allow a flowable substance, e.g., a bone cement or other substance, to be introduced into the area surrounding the bone anchor by injecting it into the cannula or passage at the proximal end of the bone anchor. The one or more outlets 5504 can be disposed along any portion of the bone anchor 5502. In the illustrated embodiment, the outlets 5504 are shown disposed along a distal portion of the bone anchor 5502 with opposed outlets forming a through-bore in the bone anchor that intersects the central cannula or passage formed in the bone anchor. In some embodiments, the laterally-facing outlets 5504 can be omitted such that the bone anchor 5502 includes a single cannula extending from openings formed at its proximal end 5508 and its distal end 5506.

The thread form of the bone anchor 5502 is similar to the embodiment shown in FIG. 46, though the illustrated fenestration of a bone anchor can also be incorporated into any of the various bone anchor configurations disclosed herein. For example, it is within the scope of the present disclosure to provide a fenestrated screw shank having the form shown in the embodiment of any of FIG. 20 or FIG. 50 as well. This means the present disclosure encompasses any combination of solid, cannulated, and/or fenestrated bone anchors having so-called "dual lead" threads (as shown in the embodiment of FIG. 20), "cortical fix" threads (as shown in the embodiment of FIG. 46), and/or "partial" threads (as shown in the embodiment of FIG. 50).

FIG. 56 illustrates another embodiment of a large diameter favored angle bone anchor assembly 5600 according to the present disclosure. In this embodiment, the locking sphere 2006, compression member 2008, drag ring 2010, and bone anchor 2004 are the same as those described above in connection with the embodiment of FIG. 20, but a differently-configured receiver head 5602 is provided. In particular, the receiver member 5602 can include one or more extended tabs 5604 protruding from a proximal end of the receiver head to facilitate manipulation of the receiver head and introduction of components, such as a set screw or other instrument or component to help reduce and secure a rod in position relative to the receiver member 5602. The one or more tabs 5604 can be integrally formed with the receiver member 5602 or otherwise coupled thereto. In some embodiments, the one or more tabs can be configured to separate from the receiver member 5602 when desired, e.g., at the end of an implantation procedure after a rod is secured relative to the receiver member. This can be accomplished in some embodiments by a user breaking the tabs at a predetermined position or otherwise separating them from the remainder of the receiver member 5602.

As with the fenestration feature described above, utilization of extended tabs can be included with any of the various embodiments described herein. For example, one or more extended tabs can be included in the receiver members of the embodiments of any of FIGS. 46 and 50 as well.

FIGS. 57-66 illustrate additional embodiments of bone anchor assemblies according to the present disclosure. These embodiments utilize many of the above-described features. Similar to the embodiments explained above, the bone anchor assemblies of these embodiments can generally include a receiver member or head, a compression member or cap, and a shank. In certain embodiments, a drag feature can also be incorporated, such as by including a drag ring, spring clip, etc., disposed within the receiver member and around sphere proximal head of the shank to provide a drag force opposing polyaxial movement of the receiver member relative to the screw shank.

Figure 57:
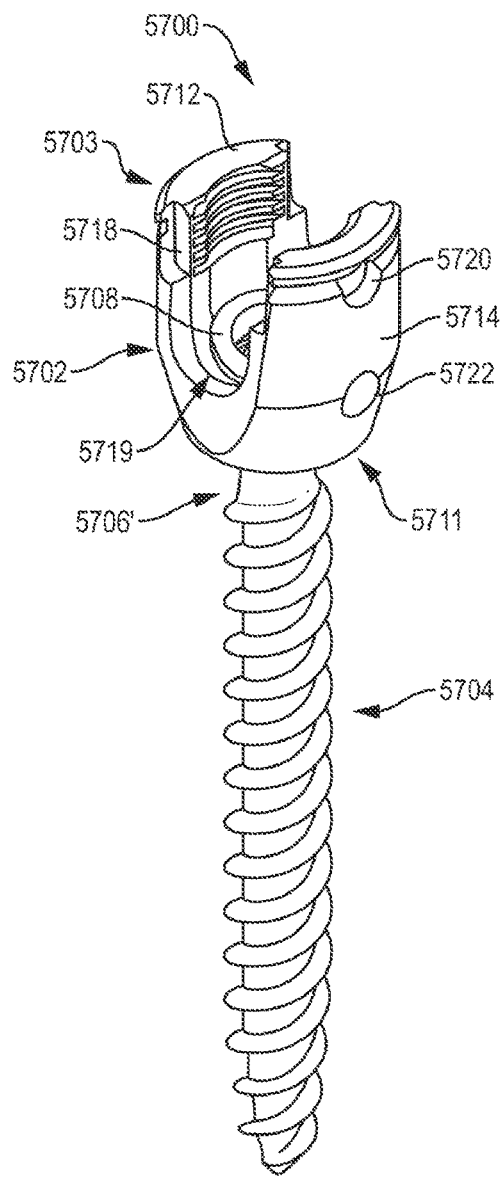
FIG. 57 is a perspective view of a bone anchor assembly, according to one embodiment.
Figure 58:
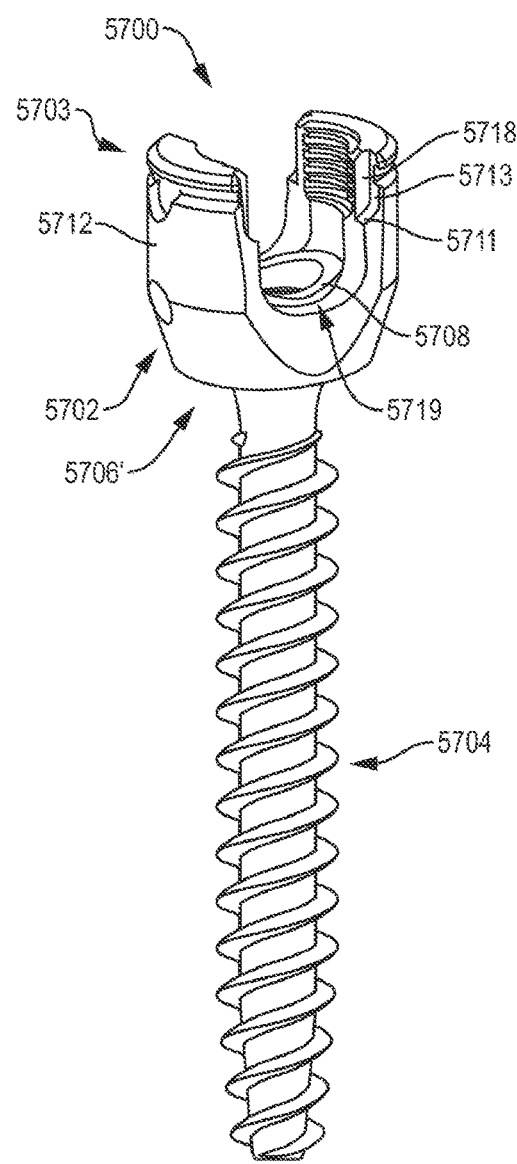
FIG. 58 is another perspective view of the bone anchor assembly of FIG. 57.
Figures 61, 62:
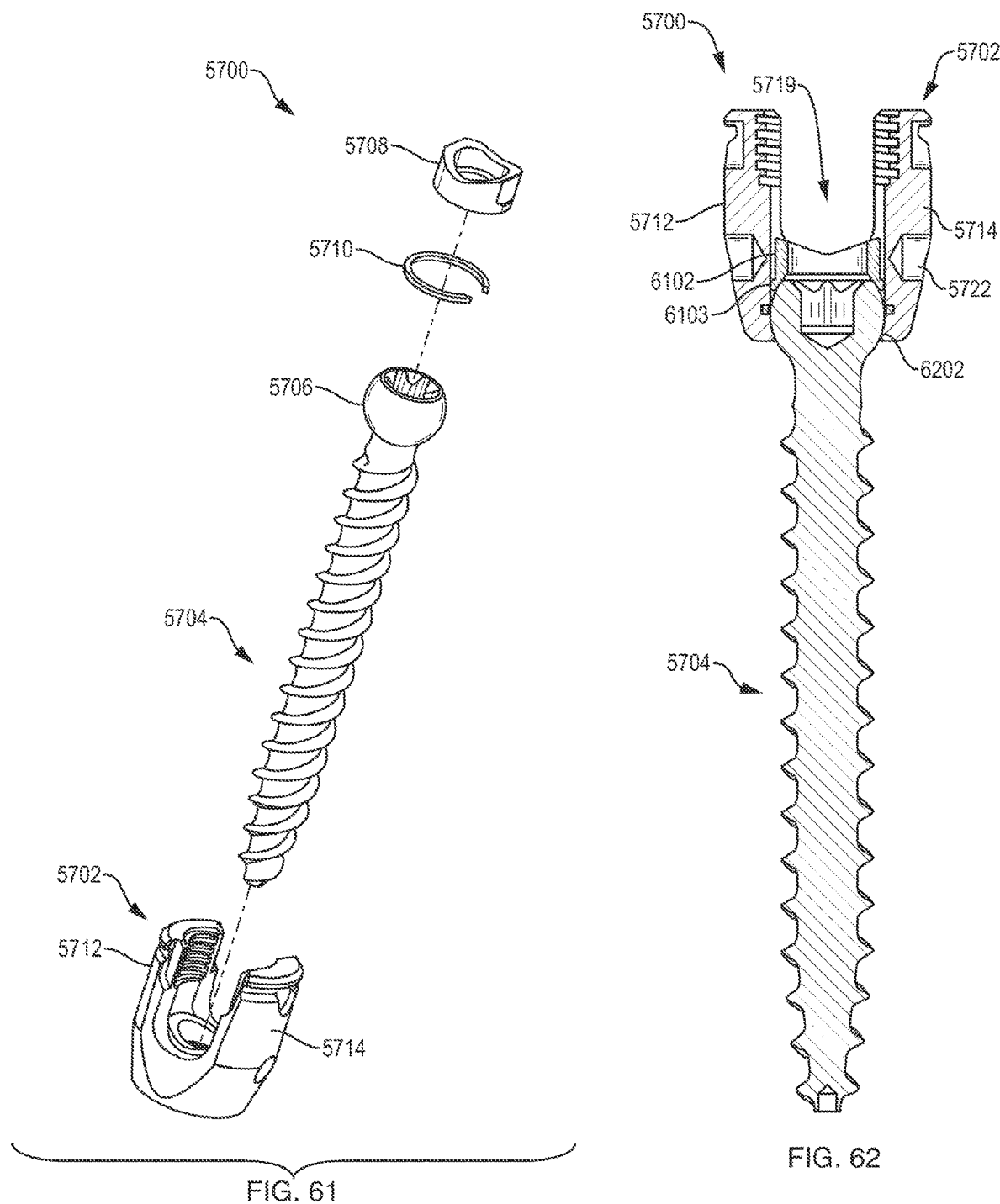
FIG. 61 is an exploded view of the bone anchor assembly of FIG. 57.
FIG. 62 is a front cross-sectional view of the bone anchor assembly of FIG. 57.

FIGS. 57-62 illustrate different views of one embodiment of a bone anchor assembly 5700 according to the present disclosure, and FIGS. 63-66 illustrate detail views of a compression cap of the assembly. More particularly, FIGS. 57 and 58 provide opposing perspective views of a bone anchor assembly 5700. FIGS. 59A, 59B, and 60 provide detail views of a proximal portion of the assembly, FIG. 61 provides an exploded view of the bone anchor assembly 5700, and FIG. 62 provides a cross-sectional view of the bone anchor assembly 5700.

Turning to FIG. 57, the receiver member 5702 of bone anchor assembly 5700 can include a proximal end 5703 defined by a pair of spaced apart arms 5712, 5714 forming a U-shaped recess 5719 (also referred to as a rod-receiving recess or slot) therebetween to receive a spinal fixation element (not shown), such as a spinal rod. A polyaxial seat 6202 can be formed in a distal end 5711 of the receiver member 5702 for polyaxially seating a proximal portion 5706 of the bone anchor/shank 5704. The bone anchor assembly 5700 can further include a compression member or cap 5708 and a drag ring 5710 disposed within the receiver member 5702, each of which can contact the proximal portion 5706 to exert friction forces thereon that can selectively resist and/or prevent any relative movement of the receiver member 5702 relative to the bone anchor 5704.

Similar to the receiver member 102, the receiver member 5702 can include at least one unilateral attachment feature 5718 that can enable a surgical instrument to couple to or engage with the receiver member 5702 in a manner that leaves the rod-receiving slot 5719 unobstructed, e.g., by allowing attachment of an instrument to the receiver member 5702 by engaging only one arm 5712 or 5714 of the receiver member 5702. In one embodiment, the receiver member 5702 can include a unilateral attachment feature 5718 on four proximal quadrants of the receiver member 5702. Similar to unilateral attachment feature 408, a unilateral attachment feature 5718 can be formed on opposing laterally-facing edges of each of the spaced apart arms 5712, 5714. A surgical instrument can attach to two adjacent unilateral features 5718 on one side of the receiver member 5702, leaving the rod-receiving slot 5719 open to receive a spinal fixation rod and/or set screw introduced distally from the proximal end 5703 of the receiver member 5702, as explained above.

Figure 59A:
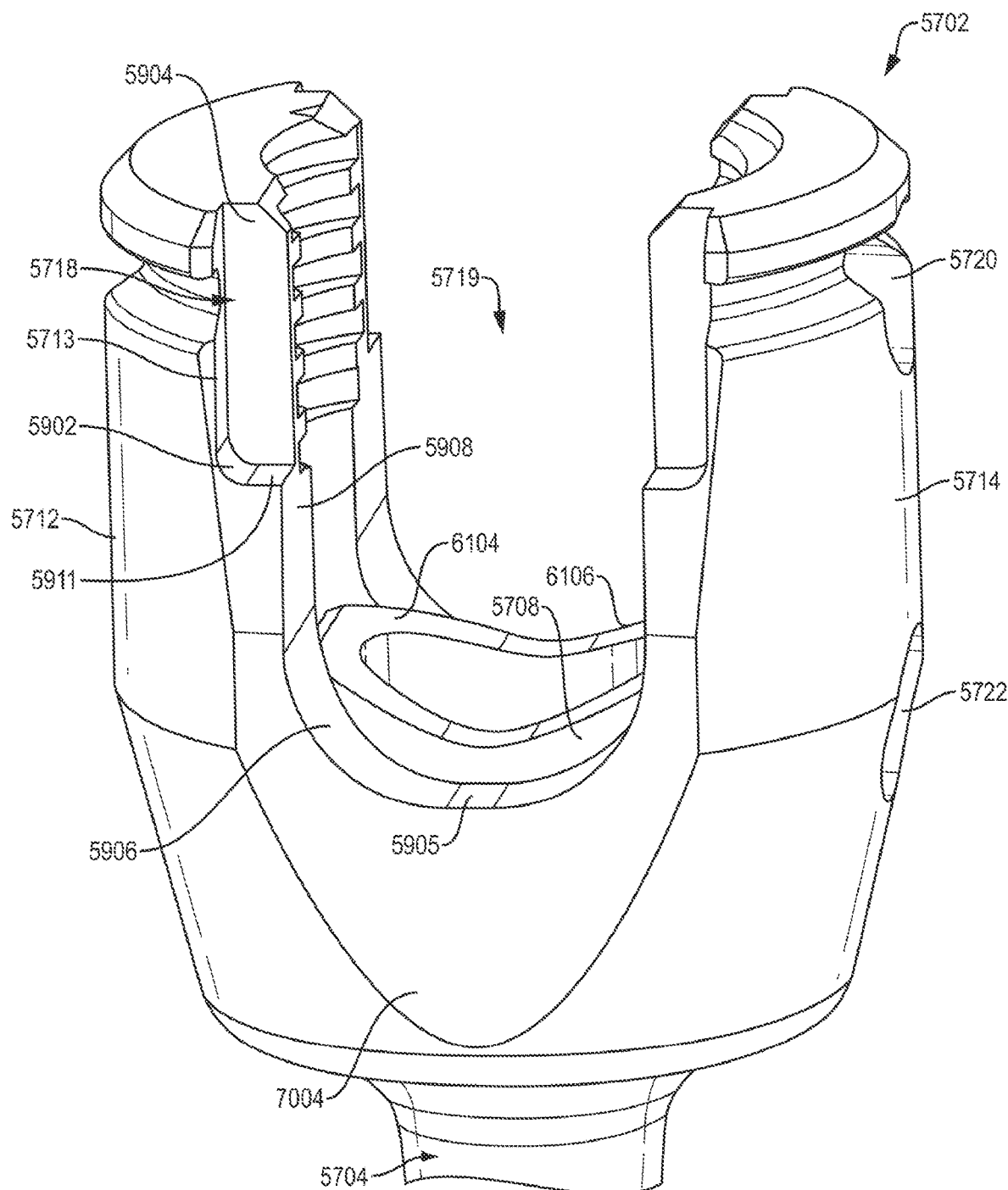
FIG. 59A is a detail perspective view of a proximal portion of the bone anchor assembly of FIG. 57.
Figure 59B:
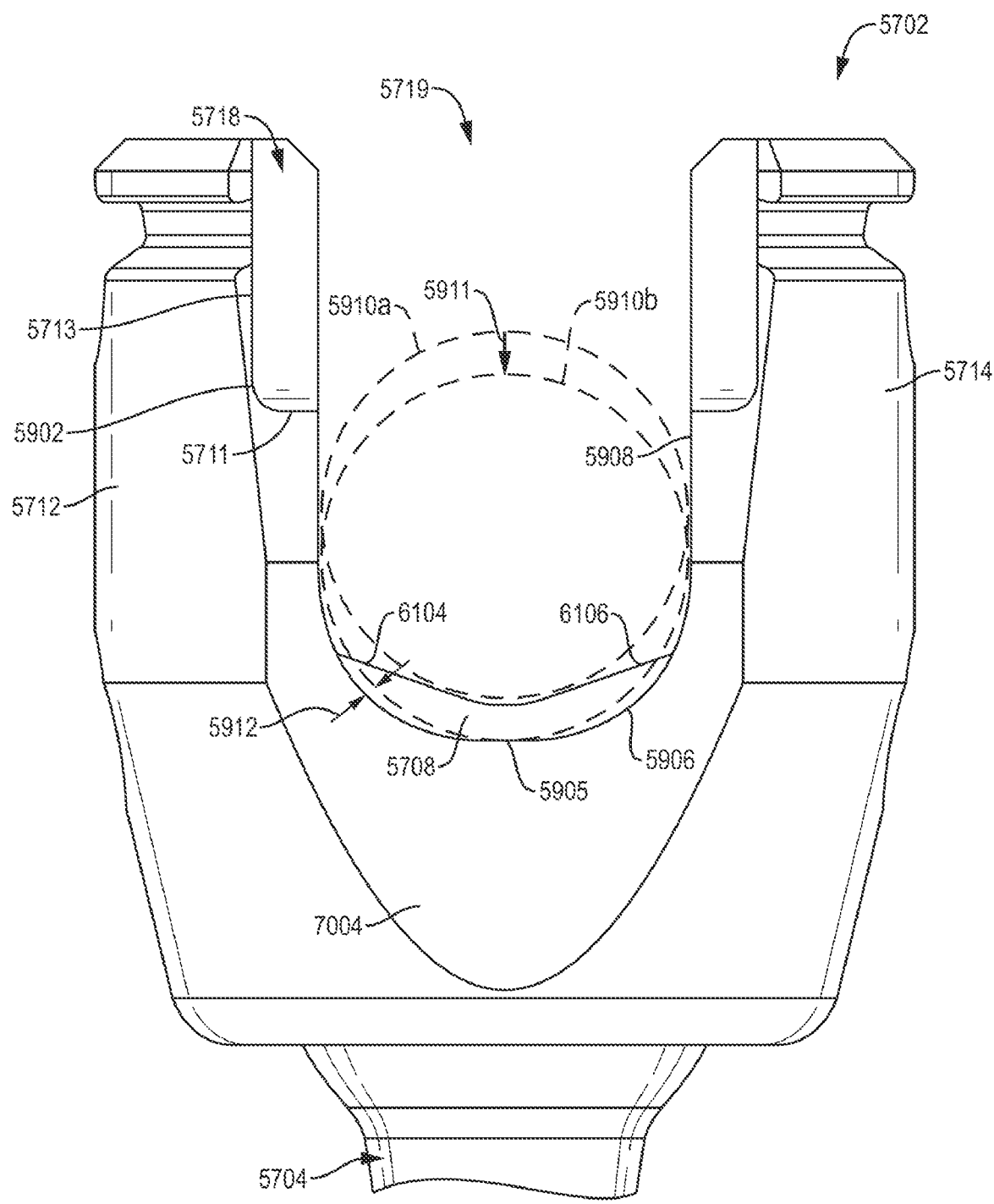
FIG. 59B is a detail front view of a proximal portion of the bone anchor assembly of FIG. 57.

As also shown in FIGS. 59A and 59B, each unilateral attachment feature 5718 can have a distal planar surface 5711 having approximately a 90 degree angle with a planar sidewall surface 5713, with a small radius concave surface 5902 connecting the two planar surfaces. The unilateral attachment feature 5718 can also include a medial planar surface 5904 disposed at approximately a 90 degree angle with the planar surfaces 5711 and 5713. Such a configuration can provide improved bracing options for an instrument coupling to the receiver member 5702 using the unilateral attachment feature 5718. This can allow an instrument to securely couple to the receiver member 5702, even using only a relatively small area for purchase.

FIGS. 59A and 59B also illustrate further features of the rod slot 5719. In particular, a horizontal planar center or bottom surface 5905 of the U-shaped cut-out that separates the arms 5712, 5714 of the receiver member 5702 is connected to a planar vertical surface 5908 of each arm by a curved surface 5906. Inclusion of the planar center surface 5905 can allow use of a smaller radius curved surface 5906, which can ensure that the curved surfaces 5906 do not interfere with a spinal rod as it presses on the compression cap 5708, even when the rod is a maximum size that can be accommodated, e.g., it takes up the entire width of the slot 5719 between the vertical surfaces 5908.

FIG. 59B illustrates an outline of a spinal fixation rod in a first position 5910a as it is reduced distally into the rod slot 5719 of the receiver member 5702. In the first position, the rod can contact the planar upper surfaces 6104, 6106 of the compression cap 5708. At a maximum size, it can also touch the vertical surfaces 5908 of each arm 5712, 5714. As the rod is further reduced, e.g., using an instrument like the rocker reducer instrument or set screw described above, it can move to a second position 5910b, as shown by arrow 5911. In doing so, it can urge the compression cap 5708 distally, thereby exerting a locking force onto the shank 5704. At the second position 5910b, the rod can reach a maximum distal position where it contacts the center planar surface 5905. As shown, the inclusion of the center planar surface 5905 allows the use of smaller radius curved surfaces 5906 to transition to the vertical surfaces 5908, which can ensure there is clearance 5912 between the curved surfaces 5906 and the rod even at the second position 5910b of maximum distal advancement relative to the receiver member 5702. If a larger radius were used, e.g., a single curved bottom surface connecting the vertical surfaces 5908, it is possible that the rod would impact the curved surface at lateral positions before reaching a desired position of maximum distal advancement, thereby reducing the locking force exerted on the compression cap 5708.

As noted above, FIG. 60 illustrates that the receiver member 5702 includes a first set of opposed sides, 6004, 6006, having a substantially straight cylindrical profile without any taper in diameter along a longitudinal axis of the receiver member 5702. A second set of opposed sides offset from the first sides 6004, 6006, can be planar and include a taper such that a distance between the second set of opposed sides decreases moving proximally along the longitudinal axis of the receiver member 5702. The first of the opposed sides 7004 (opposed side 7006 is hidden from view opposite side 7004) can be seen in FIGS. 59A and 59B, and their configuration is similar to that shown in FIG. 7.

Figure 63:
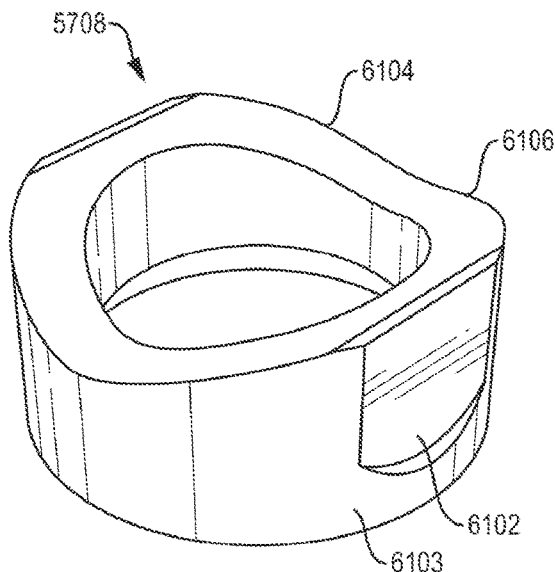
FIG. 63 is a perspective view of a compression member of the bone anchor assembly of FIG. 57.
Figure 64:
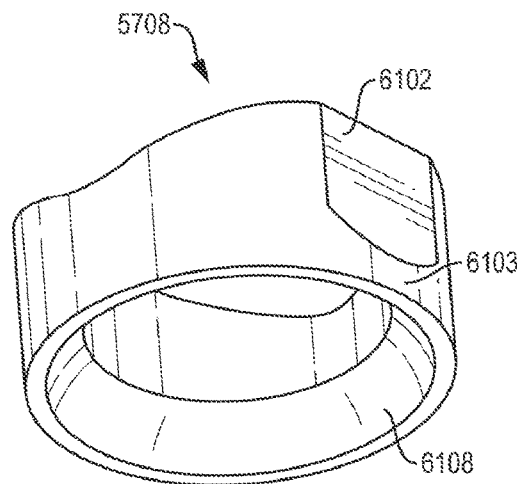
FIG. 64 is a perspective view of the compression member of FIG. 63.
Figure 65:
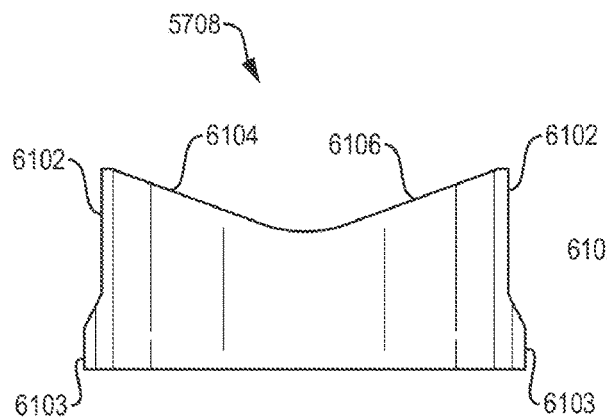
FIG. 65 is a front view of the compression member of FIG. 63.
Figure 66:
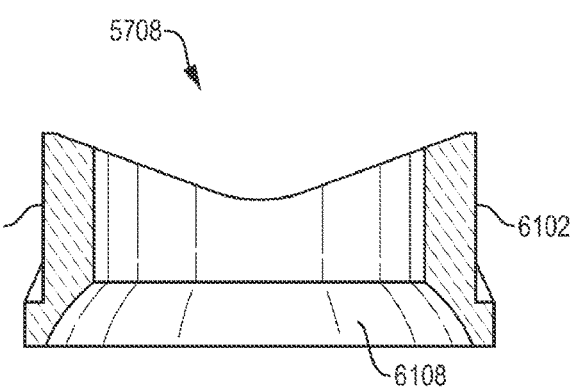
FIG. 66 is a front cross-sectional view of the compression member of FIG. 63.

FIGS. 63-66 illustrate a compression member or cap 5708 of the assembly 5700. FIGS. 63 and 64 are perspective views of one embodiment of a compression member 5708, FIG. 65 is a front view of the compression member 5708, and FIG. 66 is a front cross-sectional view of the compression member 5708. Similar to the compression cap 202, the outer surface of the compression cap 5708 can receive material from the receiver member 5702 that is displaced during a swage that can form the second rocker feature 5722. The configuration of the compression cap 5708 is different from the compression cap 202, however, in that it includes opposed flat surfaces 6102 rather than recesses 304. The opposed flat surfaces 6102 can simplify manufacturing and allow a larger surface area for contact. The opposed flat surfaces 6102 can be recessed relative to a maximum outer diameter of the compression cap 5708 and a protruding lip 6103 can be formed distal to the opposed flat surfaces. Accordingly, displaced material from the receiver member 5702 that is moved inward during a swage operation can abut the opposed flat surfaces 6102 and prevent the compression cap 5708 from being removed proximally out of the receiver member by interfering with the lip 6103. Distal advancement of the compression cap 5708 remains possible during, e.g., locking where a set screw is tightened onto a rod disposed in the slot 5719. The configuration of the opposed flat surfaces 6102 and the receiver member 5702 can be seen in the cross-sectional view of FIG. 62.

A proximal portion of the compression cap 5708, similar to cap 202, can form a seat for receiving a spinal rod. More particularly, two planar surfaces 6104, 6106 of the compression cap 5708 can be angularly offset from one another to form a substantially "V" shaped groove. The substantially flat planar surfaces 6104, 6106 can provide a seat to accommodate spinal rods of varying diameters. A bottom surface 6108 of the compression member 5708 can include a substantially spherical surface configured to contact the locking sphere 5706 and exert a friction force thereon when the compression member 5708 is advanced distally relative to the receiver member 5702 (e.g., by a user tightening a set screw into the threads formed in the proximal portion of the receiver member).

Various devices and methods disclosed herein can be used in minimally-invasive surgery and/or open surgery. While various devices and methods disclosed herein are generally described in the context of surgery on a human patient, the methods and devices disclosed herein can be used in any of a variety of surgical procedures with any human or animal subject, or in non-surgical procedures.

Various devices disclosed herein can be constructed from any of a variety of known materials. Example materials include those which are suitable for use in surgical applications, including metals such as stainless steel, titanium, nickel, cobalt-chromium, or alloys and combinations thereof, polymers such as PEEK, ceramics, carbon fiber, and so forth. Further, various methods of manufacturing can be utilized, including 3D printing or other additive manufacturing techniques, as well as more conventional manufacturing techniques, including molding, stamping, casting, machining, etc.

Various devices or components disclosed herein can be designed to be disposed of after a single use, or they can be designed to be used multiple times. In either case, however, various devices or components can be reconditioned for reuse after at least one use. Reconditioning can include any combination of the steps of disassembly, followed by cleaning or replacement of particular pieces, and subsequent reassembly. In particular, a device or component can be disassembled, and any number of the particular pieces or parts thereof can be selectively replaced or removed in any combination. Upon cleaning and/or replacement of particular parts, the device or component can be reassembled for subsequent use either at a reconditioning facility, or by a surgical team immediately prior to a surgical procedure. Reconditioning of a device or component can utilize a variety of techniques for disassembly, cleaning/replacement, and reassembly. Use of such techniques, and the resulting reconditioned device or component, are within the scope of the present disclosure.

Various devices or components described herein can be processed before use in a surgical procedure. For example, a new or used device or component can be obtained and, if necessary, cleaned. The device or component can be sterilized. In one sterilization technique, the device or component can be placed in a closed and sealed container, such as a plastic or TYVEK bag. The container and its contents can be placed in a field of radiation that can penetrate the container, such as gamma radiation, x-rays, or high-energy electrons. The radiation can kill bacteria on the device or component and in the container. The sterilized device or component can be stored in the sterile container. The sealed container can keep the device or component sterile until it is opened in the medical facility. Other forms of sterilization are also possible, including beta or other forms of radiation, ethylene oxide, steam, or a liquid bath (e.g., cold soak). Certain forms of sterilization may be better suited to use with different devices or components, or portions thereof, due to the materials utilized, the presence of electrical components, etc.

In this disclosure, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B," "one or more of A and B," and "A and/or B" are each intended to mean "A alone, B alone, or A and B together." A similar interpretation is also intended for lists including three or more items. For example, the phrases "at least one of A, B, and C," "one or more of A, B, and C," and "A, B, and/or C" are each intended to mean "A alone, B alone, C alone, A and B together, A and C together, B and C together, or A and B and C together." In addition, use of the term "based on," is intended to mean, "based at least in part on," such that an un-recited feature or element is also permissible.

Further features and advantages based on the above-described embodiments are possible and within the scope of the present disclosure. Accordingly, the disclosure is not to be limited by what has been particularly shown and described. All publications and references cited herein are expressly incorporated herein by reference in their entirety, except for any definitions, subject matter disclaimers or disavowals, and except to the extent that the incorporated material is inconsistent with the express disclosure herein, in which case the language in this disclosure controls.

Examples of the above-described embodiments can include the following:
1. A bone anchor assembly, comprising:
   a bone anchor having a proximal head portion and a distal threaded bone-engaging portion; and
   a receiver member having a proximal end defined by a pair of spaced apart arms forming a U-shaped recess therebetween, a distal end having a polyaxial seat formed therein for polyaxially seating the head portion of the bone anchor, a groove formed in an outer surface of each of the spaced apart arms at a proximal end thereof, a first recess formed in the outer surface of each arm with at least a portion of the first recess intersecting the groove, and a second recess formed in an outer surface of the receiver member at a position distal to the first recesses;
wherein the first recesses and the second recesses are configured to couple to a surgical instrument.

2. The assembly of claim 1, wherein at least a portion of the first recess in each arm extends proximally beyond the groove.

3. The assembly of claim 1 or 2, wherein each of the second recesses is longitudinally aligned with one of the first recesses.

4. The assembly of any of claims 1 to 3, wherein the first recesses are configured to pivotably couple to a surgical instrument.

5. The assembly of any of claims 1 to 4, wherein the pair of second recesses are configured to pivotably couple to a surgical instrument.

6. The assembly of any of claims 1 to 5, wherein the U-shaped recess is configured to receive a spinal fixation element of various sizes.

7. The assembly of any of claims 1 to 6, wherein each spaced apart arm has a laterally-facing recessed portion formed on opposite lateral edges of the arm, each of the lateral-facing recessed portions facing away from a central proximal-distal axis of the receiver member, wherein the lateral-facing recessed portions are configured to engage with a surgical instrument such that the U-shaped recess remains unobstructed.

8. The assembly of claim 7, wherein each of the lateral-facing recessed portions extend distally from the proximal end of the spaced apart arms.

9. The assembly of claim 7, wherein each lateral-facing recessed portion has a concave distal surface.

10. The assembly of claim 7, wherein each lateral-facing recessed portion has a first planar surface, a second planar surface substantially perpendicular to the first planar surface, and a curved surface therebetween.

11. The assembly of any of claims 1 to 10, wherein the proximal ends of the spaced apart arms lie along a common circular circumferential path.

12. The assembly of any of claims 1 to 11, wherein opposing laterally-facing sides of the receiver member taper inward towards the proximal end of the receiver member.

13. The assembly of any of claims 1 to 11, wherein a first pair of opposed sides of the receiver member has a first taper with respect to a first plane that contains a proximal-distal axis of the receiver member.

14. The assembly of claim 13, wherein a second pair of opposed sides of the receiver member has a second taper with respect to a second plane that contains the proximal-distal axis and is offset from the first plane.

15. The assembly of claim 14, wherein the first plane is perpendicular to the second plane.

16. The assembly of any of claims 1 to 15, further comprising a drag ring disposed within the receiver member, the drag ring configured to exert a friction force on the head portion of the bone anchor.

17. The assembly of any of claims 1 to 16, further comprising a compression member disposed within the receiver member, wherein a proximal portion of the compression member includes opposing planar surfaces that are angularly offset from one another forming a seat for receiving a spinal fixation element.

18. The assembly of claim 17, wherein material displaced in the formation of the second recesses is configured to restrict movement of the compression member relative to the receiver member.

19. The assembly of claim 18, wherein the displaced material is received within corresponding recesses formed in the compression member.

20. The assembly of any of claims 1 to 19, further comprising a pair of reduction tabs extending proximally from the pair of spaced apart arms.

21. The assembly of any of claims 1 to 20, further comprising a fixation element with external square threads configured to be received between the spaced apart arms of the receiver member.

22. The assembly of any of claims [0207] to 21, wherein the bone anchor includes a bore extending proximally from a distal tip of the bone engaging portion.

23. The assembly of claim 22, wherein the bore extends through an entire length of the bone anchor.

24. The assembly of claim 22, wherein the bore is a blind bore.

25. The assembly of any of claims 1 to 2423, wherein the distal bone-engaging portion further comprises external threads that extend distally along the bone-engaging portion to a distal tip thereof.

26. A bone anchor assembly, comprising:
a bone anchor having a proximal head portion and a distal threaded bone-engaging portion;
a receiver member having a proximal end defined by a pair of spaced apart arms forming a U-shaped recess configured to receive a spinal fixation element therebetween and a distal end having a polyaxial seat formed therein for polyaxially seating the head portion of the bone anchor;
wherein opposing laterally-facing sides of the receiver member taper inward towards the proximal end of the receiver member.

27. The assembly of claim 26, wherein a first pair of the opposing laterally-facing sides of the receiver member has a first taper with respect to a first plane that contains a proximal-distal axis of the receiver member.

28. The assembly of claim 27, wherein a second pair of the opposing laterally-facing sides of the receiver member has a second taper with respect to a second plane that contains the proximal-distal axis and is offset from the first plane.

29. The assembly of claim 28, wherein the first plane is perpendicular to the second plane.

30. The assembly of any of claims 26 to 29, wherein the receiver member further comprises a groove formed in an outer surface of each of the spaced apart arms at a proximal end thereof, a first recess formed in the outer surface of each arm with at least a portion of the first recess intersecting the groove, and a second recess formed in an outer surface of the receiver member at a position distal to the first recesses;
wherein the first recesses and the second recesses are configured to couple to a surgical instrument.

31. The assembly of claim 30, wherein at least a portion of the first recess in each arm extends proximally beyond the groove.

32. The assembly of claim 30 or 31, wherein each of the second recesses is longitudinally aligned with one of the first recesses.

33. The assembly of any of claims 30 to 32, wherein the first recesses are configured to pivotably couple to a surgical instrument.

34. The assembly of any of claims 30 to 33, wherein the pair of second recesses are configured to pivotably couple to a surgical instrument.

35. The assembly of any of claims 26 to 34, wherein the U-shaped recess is configured to receive a spinal fixation element of various sizes.
36. The assembly of any of claims 26 to 35, wherein each spaced apart arm has a laterally-facing recessed portion formed on opposite lateral edges of the arm, each of the lateral-facing recessed portions facing away from a central proximal-distal axis of the receiver member, wherein the lateral-facing recessed portions are configured to engage with a surgical instrument such that the U-shaped recess remains unobstructed.
37. The assembly of claim 36, wherein each of the lateral-facing recessed portions extend distally from the proximal end of the spaced apart arms.
38. The assembly of claim 36, wherein each lateral-facing recessed portion has a concave distal surface.
39. The assembly of claim 38, wherein each lateral-facing recessed portion has a first planar surface, a second planar surface substantially perpendicular to the first planar surface, and a curved surface therebetween.
40. The assembly of any of claims 26 to 39, wherein the proximal ends of the spaced apart arms lie along a common circular circumferential path.
41. The assembly of any of claims 26 to 40, further comprising a drag ring disposed within the receiver member, the drag ring configured to exert a friction force on the head portion of the bone anchor.
42. The assembly of any of claims 26 to 41, further comprising a compression member disposed within the receiver member, wherein a proximal portion of the compression member includes opposing planar surfaces that are angularly offset from one another forming a seat for receiving a spinal fixation element.
43. The assembly of claim 42, wherein material displaced in the formation of the second recesses is configured to restrict movement of the compression member relative to the receiver member.
44. The assembly of claim 43, wherein the displaced material is received within corresponding recesses formed in the compression member.
45. The assembly of any of claims 26 to 44, further comprising a pair of reduction tabs extending proximally from the pair of spaced apart arms.
46. The assembly of any of claims 30 to 45, further comprising a fixation element with external square threads configured to be received between the spaced apart arms of the receiver member.
47. The assembly of any of claims 30 to 46, wherein the bone anchor includes a bore extending proximally from a distal tip of the bone engaging portion.
48. The assembly of claim 47, wherein the bore extends through an entire length of the bone anchor.
49. The assembly of claim 47, wherein the bore is a blind bore.
50. The assembly of any of claims 30 to 49, wherein the distal bone-engaging portion further comprises external threads that extend distally along the bone-engaging portion to a distal tip thereof.
51. A bone anchor assembly, comprising:
    a bone anchor having a proximal head portion and a distal threaded bone-engaging portion;
    a receiver member having a proximal end defined by a pair of spaced apart arms forming a U-shaped recess configured to receive a spinal fixation element therebetween and a distal end having a polyaxial seat formed therein for polyaxially seating the head portion of the bone anchor;
    wherein proximal ends of the spaced apart arms lie along a common circular circumferential path.
52. The assembly of claim 51, wherein the receiver member further comprises a groove formed in an outer surface of each of the spaced apart arms at a proximal end thereof, a first recess formed in the outer surface of each arm with at least a portion of the first recess intersecting the groove, and a second recess formed in an outer surface of the receiver member at a position distal to the first recesses;
    wherein the first recesses and the second recesses are configured to couple to a surgical instrument.
53. The assembly of claim 52, wherein at least a portion of the first recess in each arm extends proximally beyond the groove.
54. The assembly of claim 52 or 53, wherein each of the second recesses is longitudinally aligned with one of the first recesses.
55. The assembly of any of claims 51 to 54, wherein the first recesses are configured to pivotably couple to a surgical instrument.
56. The assembly of any of claims 51 to 55, wherein the pair of second recesses are configured to pivotably couple to a surgical instrument.
57. The assembly of any of claims 51 to 56, wherein the U-shaped recess is configured to receive a spinal fixation element of various sizes.
58. The assembly of any of claims 51 to 57, wherein each spaced apart arm has a laterally-facing recessed portion formed on opposite lateral edges of the arm, each of the lateral-facing recessed portions facing away from a central proximal-distal axis of the receiver member, wherein the lateral-facing recessed portions are configured to engage with a surgical instrument such that the U-shaped recess remains unobstructed.
59. The assembly of claim 58, wherein each of the lateral-facing recessed portions extend distally from the proximal end of the spaced apart arms.
60. The assembly of claim 58, wherein each lateral-facing recessed portion has a concave distal surface.
61. The assembly of claim 60, wherein each lateral-facing recessed portion has a first planar surface, a second planar surface substantially perpendicular to the first planar surface, and a curved surface therebetween.
62. The assembly of any of claims 51 to 61, wherein opposing laterally-facing sides of the receiver member taper inward towards the proximal end of the receiver member.
63. The assembly of any of claims 51 to 61, wherein a first pair of opposed sides of the receiver member has a first taper with respect to a first plane that contains a proximal-distal axis of the receiver member.
64. The assembly of claim 63, wherein a second pair of opposed sides of the receiver member has a second taper with respect to a second plane that contains the proximal-distal axis and is offset from the first plane.
65. The assembly of claim 64, wherein the first plane is perpendicular to the second plane.
66. The assembly of any of claims 51 to 65, further comprising a drag ring disposed within the receiver member, the drag ring configured to exert a friction force on the head portion of the bone anchor.
67. The assembly of any of claims 51 to 66, further comprising a compression member disposed within the receiver member, wherein a proximal portion of the compression member includes opposing planar surfaces that are angularly offset from one another forming a seat for receiving a spinal fixation element.
68. The assembly of claim 67, wherein material displaced in the formation of the second recesses is configured to restrict movement of the compression member relative to the receiver member.
69. The assembly of claim 67, wherein the displaced material is received within corresponding recesses formed in the compression member.
70. The assembly of any of claims 51 to 69, further comprising a pair of reduction tabs extending proximally from the pair of spaced apart arms.
71. The assembly of any of claims 51 to 70, further comprising a fixation element with external square threads configured to be received between the spaced apart arms of the receiver member.
72. The assembly of any of claims 51 to 71, wherein the bone anchor includes a bore extending proximally from a distal tip of the bone engaging portion.
73. The assembly of claim 72, wherein the bore extends through an entire length of the bone anchor.
74. The assembly of claim 72, wherein the bore is a blind bore.
75. The assembly of any of claims 51 to 74, wherein the distal bone-engaging portion further comprises external threads that extend distally along the bone-engaging portion to a distal tip thereof.
76. A bone anchor assembly, comprising:
  a bone anchor having a proximal head portion, a distal bone-engaging portion with external threads that extend to a distal tip of bone anchor, and a bore centered within the distal bone-engaging portion extending proximally from the distal tip of the bone anchor; and
  a receiver member having a proximal end defined by a pair of spaced apart arms forming a U-shaped recess configured to receive a spinal fixation element therebetween and a distal end having a polyaxial seat formed therein for polyaxially seating the head portion of the bone anchor.
77. The assembly of claim 76, wherein the receiver member further comprises a groove formed in an outer surface of each of the spaced apart arms at a proximal end thereof, a first recess formed in the outer surface of each arm with at least a portion of the first recess intersecting the groove, and a second recess formed in an outer surface of the receiver member at a position distal to the first recesses;
  wherein the first recesses and the second recesses are configured to couple to a surgical instrument.
78. The assembly of claim 77, wherein at least a portion of the first recess in each arm extends proximally beyond the groove.
79. The assembly of claim 77 or 78, wherein each of the second recesses is longitudinally aligned with one of the first recesses.
80. The assembly of any of claims 77 to 79, wherein the first recesses are configured to pivotably couple to a surgical instrument.
81. The assembly of any of claims 77 to 80, wherein the pair of second recesses are configured to pivotably couple to a surgical instrument.
82. The assembly of any of claims 76 to 81, wherein the U-shaped recess is configured to receive a spinal fixation element of various sizes.
83. The assembly of any of claims 76 to 82, wherein each spaced apart arm has a laterally-facing recessed portion formed on opposite lateral edges of the arm, each of the lateral-facing recessed portions facing away from a central proximal-distal axis of the receiver member, wherein the lateral-facing recessed portions are configured to engage with a surgical instrument such that the U-shaped recess remains unobstructed.
84. The assembly of claim 83, wherein each of the lateral-facing recessed portions extend distally from the proximal end of the spaced apart arms.
85. The assembly of claim 83, wherein each lateral-facing recessed portion has a concave distal surface.
86. The assembly of any of claims 76 to 85, wherein the proximal ends of the spaced apart arms lie along a common circular circumferential path.
87. The assembly of any of claims 76 to 86, wherein opposing laterally-facing sides of the receiver member taper inward towards the proximal end of the receiver member.
88. The assembly of any of claims 76 to 86, wherein a first pair of opposed sides of the receiver member has a first taper with respect to a first plane that contains a proximal-distal axis of the receiver member.
89. The assembly of claim 88, wherein a second pair of opposed sides of the receiver member has a second taper with respect to a second plane that contains the proximal-distal axis and is offset from the first plane.
90. The assembly of claim 89, wherein the first plane is perpendicular to the second plane.
91. The assembly of any of claims 76 to 90, further comprising a drag ring disposed within the receiver member, the drag ring configured to exert a friction force on the head portion of the bone anchor.
92. The assembly of any of claims 76 to 91, further comprising a compression member disposed within the receiver member, wherein a proximal portion of the compression member includes opposing planar surfaces that are angularly offset from one another forming a seat for receiving a spinal fixation element.
93. The assembly of claim 92, wherein material displaced in the formation of the second recesses is configured to restrict movement of the compression member relative to the receiver member.
94. The assembly of claim 93, wherein the displaced material is received within corresponding recesses formed in the compression member.
95. The assembly of any of claims 76 to 94, further comprising a pair of reduction tabs extending proximally from the pair of spaced apart arms.
96. A bone anchor assembly, comprising:
  a bone anchor having a proximal head portion, a distal bone-engaging portion with external threads that extend to a distal tip of the bone anchor, and a bore centered within the distal bone-engaging portion extending proximally from the distal tip of the bone anchor; and
  a receiver member having a proximal end defined by a pair of spaced apart arms forming a U-shaped recess therebetween, a distal end having a polyaxial seat formed therein for polyaxially seating the head portion of the bone anchor, a groove formed in an outer surface of each of the spaced apart arms at a proximal end thereof, a first recess formed in the outer surface of each arm with at least a portion of the first recess intersecting the groove, and a second recess formed in an outer surface of the receiver member at a position distal to the first recesses;

a drag ring disposed within the receiver member, the drag ring configured to exert a friction force on the head portion of the bone anchor; and a compression member disposed within the receiver member, wherein a proximal portion of the compression member includes opposing planar surfaces that are angularly offset from one another forming a seat for receiving a spinal fixation element;

wherein the first recesses and the second recesses of the receiver member are configured to couple to a surgical instrument;

wherein each spaced apart arm has a laterally-facing recessed portion formed on opposite lateral edges of the arm, each of the lateral-facing recessed portions facing away from a central proximal-distal axis of the receiver member, wherein the lateral-facing recessed portions are configured to engage with a surgical instrument such that the U-shaped recess remains unobstructed;

wherein opposing laterally-facing sides of the receiver member taper inward towards the proximal end of the receiver member.

97. The assembly of claim 96, wherein the proximal ends of the spaced apart arms lie along a common circular circumferential path.

98. The assembly of any of claims 96 to 97, wherein the compression member is locked against removal from an interior of the receiver member.

99. A bone anchor assembly, comprising:
a bone anchor having a proximal portion and a distal threaded bone-engaging portion;
a locking sphere configured to couple to the proximal portion of the bone anchor;
a receiver member having a proximal end defined by a pair of spaced apart arms forming a U-shaped recess therebetween, and a distal end having a polyaxial seat formed therein for polyaxially seating the locking sphere;
a drag ring disposed within the receiver member and configured to exert a friction force on the locking sphere; and
a compression member disposed within the receiver member;
wherein a distal facing surface of the receiver member is obliquely angled relative to a central proximal-distal axis of the receiver member to provide a greater degree of angulation of the bone anchor relative to the receiver member in a first direction relative to a second, opposite direction.

100. The assembly of claim 99,
wherein the receiver member includes a groove formed in an outer surface of each of the spaced apart arms at a proximal end thereof;
wherein the receiver member includes a first recess formed in the outer surface of each arm with at least a portion of the first recess intersecting the groove, and a second recess formed in an outer surface of the receiver member at a position distal to the first recesses;
wherein the first and second recesses are configured to couple to a surgical instrument.

101. The assembly of claim 100, wherein at least a portion of the first recess in each arm extends proximally beyond the groove.

102. The assembly of claim 100 or 101, wherein the second recess is longitudinally aligned with one of the first recesses.

103. The assembly of any of claims 100 to 102, wherein the first recesses are configured to pivotably couple to a surgical instrument.

104. The assembly of any of claims 100 to 103, wherein the second recess is configured to pivotably couple to a surgical instrument.

105. The assembly of any of claims 99 to 104, wherein the U-shaped recess is configured to receive a spinal fixation element of various sizes.

106. The assembly of any of claims 99 to 105, wherein each spaced apart arm has a laterally-facing recessed portion formed on opposite lateral edges of the arm, each of the lateral-facing recessed portions facing away from the central proximal-distal axis of the receiver member, wherein the lateral-facing recessed portions are configured to engage with a surgical instrument such that the U-shaped recess remains unobstructed.

107. The assembly of claim 106, wherein each of the lateral-facing recessed portions extend distally from the proximal end of the spaced apart arms.

108. The assembly of claim 106, wherein each lateral-facing recessed portion has a concave distal surface.

109. The assembly of claim 108, wherein each lateral-facing recessed portion has a first planar surface, a second planar surface substantially perpendicular to the first planar surface, and a curved surface therebetween.

110. The assembly of any of claims 99 to 109, wherein the proximal ends of the spaced apart arms lie along a common circular circumferential path.

111. The assembly of any of claims 99 to 110, wherein opposing laterally-facing sides of the receiver member taper inward towards the proximal end of the receiver member.

112. The assembly of any of claims 99 to 111, wherein a first pair of opposed sides of the receiver member has a first taper with respect to a first plane that contains a proximal-distal axis of the receiver member.

113. The assembly of claim 112, wherein a second pair of opposed sides of the receiver member has a second taper with respect to a second plane that contains the proximal-distal axis and is offset from the first plane.

114. The assembly of claim 113, wherein the first plane is perpendicular to the second plane.

115. The assembly of any of claims 99 to 114, wherein a proximal portion of the compression member includes opposing planar surfaces that are angularly offset from one another forming a seat for receiving a spinal fixation element.

116. The assembly of claim 115, wherein material displaced in the formation of the second recess is configured to restrict movement of the compression member relative to the receiver member.

117. The assembly of claim 116, wherein the displaced material is received within a corresponding recess formed in the compression member.

118. The assembly of any of claims 99 to 117, further comprising a pair of reduction tabs extending proximally from the pair of spaced apart arms.

119. The assembly of any of claims 99 to 118, further comprising a fixation element with external square threads configured to be received between the spaced apart arms of the receiver member.

120. The assembly of any of claims 99 to 119, wherein the bone anchor includes a bore extending proximally from a distal tip of the bone engaging portion.

121. The assembly of claim 120, wherein the bore extends through an entire length of the bone anchor.

122. The assembly of claim 121, wherein the bone anchor includes at least one outlet formed in a lateral surface thereof that intersects with the bore.

123. The assembly of claim 120, wherein the bore is a blind bore.

124. The assembly of any of claims 99 to 123, wherein the distal bone-engaging portion further comprises external threads that extend distally along the bone-engaging portion to a distal tip thereof.

125. The assembly of any of claims 99 to 124, wherein the compression member is configured to exert a force on the locking sphere upon distal advancement of the compression member relative to the receiver member.

126. The assembly of any of claims 99 to 125, wherein the bone anchor includes threads of a first pitch formed along a first bone-engaging portion thereof and threads of a second pitch formed along a second bone-engaging portion that is proximal of the first bone engaging portion.

127. The assembly of claim 126, wherein the first pitch is greater than the second pitch.

128. The assembly of any of claims 99 to 127,
wherein the bone anchor includes threads formed on a first, distal portion thereof and a second portion without threads that is disposed between the first portion and the proximal portion of the bone anchor;
wherein a length of the second portion without threads is at least about 30% of a length of the first portion having threads formed thereon.

129. The assembly of claim 128, wherein the length of the second portion is between about 30% and about 90% of the length of the first portion.

What is claimed is:

1. A bone anchor assembly, comprising:
a bone anchor having a proximal head portion and a distal threaded bone-engaging portion;
a receiver member having a proximal end defined by a pair of spaced apart arms forming a U-shaped recess therebetween, a distal end having a polyaxial seat formed therein for polyaxially seating the head portion of the bone anchor, a groove formed in an outer surface of each of the spaced apart arms at a proximal end thereof, a first recess formed in the outer surface of each arm with at least a portion of the first recess intersecting the groove, and a second recess formed in an outer surface of the receiver member at a position distal to each of the first recesses; and
a compression member disposed within the receiver member, wherein a proximal portion of the compression member includes opposing planar surfaces that are angularly offset from one another to form a substantially "V" shaped groove, and a free end of a distal portion of the compression member is disposed proximal to a maximum diameter of the proximal head portion when the compression member is disposed around the proximal head portion;
wherein the first recesses and the second recesses are configured to couple to a surgical instrument.

2. A bone anchor assembly, comprising:
a bone anchor having a proximal head portion and a distal threaded bone-engaging portion;
a receiver member having a proximal end defined by a pair of spaced apart arms forming a U-shaped recess therebetween, a distal end having a polyaxial seat formed therein for polyaxially seating the head portion of the bone anchor, a groove formed in an outer surface of each of the spaced apart arms at a proximal end thereof, a first recess formed in the outer surface of each arm with at least a portion of the first recess intersecting the groove, and a second recess formed in an outer surface of the receiver member at a position distal to each of the first recesses; and
a compression member disposed within the receiver member, wherein a proximal portion of the compression member includes opposing planar surfaces that are angularly offset from one another forming a seat for receiving a spinal fixation element, the opposing planar surfaces being configured to contact the spinal fixation element when it is disposed in the seat, and a free end of a distal portion of the compression member is disposed proximal to a maximum diameter of the proximal head portion when the compression member is disposed around the proximal head portion;
wherein the first recesses and the second recesses are configured to couple to a surgical instrument.

3. The assembly of claim 2, wherein the compression member comprises opposed flat surfaces that align with the second recesses when the compression member is disposed within the receiver member.

4. The assembly of claim 3, wherein the opposed flat surfaces are recessed relative to a maximum outer diameter of the compression member such that a protruding lip is formed distal to the opposed flat surfaces.

5. The assembly of claim 3, wherein the compression member is defined by an uninterrupted sidewall that extends between the opposed flat surfaces.

6. A bone anchor assembly, comprising:
a bone anchor having a proximal head portion and a distal threaded bone-engaging portion;
a receiver member having a proximal end defined by a pair of spaced apart arms forming a U-shaped recess therebetween, a distal end having a polyaxial seat formed therein for polyaxially seating the head portion of the bone anchor, a groove formed in an outer surface of each of the spaced apart arms at a proximal end thereof that extends between opposite lateral edges of each of the spaced apart arms, a first recess formed in the outer surface of each arm with at least a portion of the first recess intersecting the groove, and a second recess formed in an outer surface of the receiver member at a position distal to each of the first recesses; and
a compression member disposed within the receiver member, wherein a proximal portion of the compression member includes opposing planar surfaces that are angularly offset from one another forming a seat for receiving a spinal fixation element, and a distal portion of the compression member includes a distal-facing rim having an uninterrupted circumference;
wherein the first recesses and the second recesses are configured to couple to a surgical instrument.

7. The assembly of claim 6, wherein at least a portion of the first recess in each arm extends proximally beyond the groove.

8. The assembly of claim 6, wherein each of the second recesses is longitudinally aligned with one of the first recesses.

9. The assembly of claim 6, wherein the first recesses are configured to pivotably couple to a surgical instrument.

10. The assembly of claim 6, wherein the pair of second recesses are configured to pivotably couple to a surgical instrument.

11. The assembly of claim 6, wherein the U-shaped recess is configured to receive a spinal fixation element of various sizes.

12. The assembly of claim 6, wherein each spaced apart arm has a laterally-facing recessed portion formed on the opposite lateral edges of the arm, each of the lateral-facing recessed portions facing away from a central proximal-distal axis of the receiver member, wherein the lateral-facing recessed portions are configured to engage with a surgical instrument such that the U-shaped recess remains unobstructed.

13. The assembly of claim 12, wherein each of the lateral-facing recessed portions extend distally from the proximal end of the spaced apart arms.

14. The assembly of claim 12, wherein each lateral-facing recessed portion has a concave distal surface.

15. The assembly of claim 12, wherein each lateral-facing recessed portion has a first planar surface, a second planar surface substantially perpendicular to the first planar surface, and a curved surface therebetween.

16. The assembly of claim 6, wherein the proximal ends of the spaced apart arms lie along a common circular circumferential path.

17. The assembly of claim 6, wherein opposing laterally-facing sides of the receiver member taper inward towards the proximal end of the receiver member.

18. The assembly of claim 6, wherein a first pair of opposed sides of the receiver member has a first taper with respect to a first plane that contains a proximal-distal axis of the receiver member.

19. The assembly of claim 18, wherein a second pair of opposed sides of the receiver member has a second taper with respect to a second plane that contains the proximal-distal axis and is offset from the first plane.

20. The assembly of claim 19, wherein the first plane is perpendicular to the second plane.

21. The assembly of claim 6, further comprising a drag ring disposed within the receiver member, the drag ring configured to exert a friction force on the head portion of the bone anchor.

22. The assembly of claim 6, wherein movement of the compression member is restricted relative to the receiver member.

23. The assembly of claim 22, wherein the displaced material is received within corresponding recesses formed in the compression member.

24. The assembly of claim 6, further comprising a pair of reduction tabs extending proximally from the pair of spaced apart arms.

25. The assembly of claim 6, further comprising a fixation element with external square threads configured to be received between the spaced apart arms of the receiver member.

26. The assembly of claim 6, wherein the bone anchor includes a bore extending proximally from a distal tip of the bone engaging portion.

27. The assembly of claim 26, wherein the bore extends through an entire length of the bone anchor.

28. The assembly of claim 26, wherein the bore is a blind bore.

29. The assembly of claim 6, wherein the distal bone-engaging portion further comprises external threads that extend distally along the bone-engaging portion to a distal tip thereof.

30. The assembly of claim 6, further comprising a drag ring disposed around the proximal head portion such that a distal end of the drag ring is proximal to a distal end of the receiver member when the bone anchor is disposed within the receiver member.

31. The assembly of claim 6, wherein a second portion of the first recess in each arm extends distal to a distal-most end of the groove.

32. The assembly of claim 6, wherein the opposing planar surfaces are configured to be contacted by the spinal fixation element when it is disposed in the seat.

33. The assembly of claim 6, wherein the distal-facing rim lies in a plane that is perpendicular to a central longitudinal axis of the bone anchor.

* * * * *